US006468738B1

(12) United States Patent
Kang et al.

(10) Patent No.: US 6,468,738 B1
(45) Date of Patent: Oct. 22, 2002

(54) HETERODIMERIC RECEPTOR LIBRARIES USING PHAGEMIDS

(75) Inventors: Angray Kang, Carlsbad; Carlos Barbas; Richard A. Lerner, both of La Jolla, all of CA (US)

(73) Assignee: The Scripps Research Institute, La Jolla, CA (US)

( * ) Notice: Subject to any disclaimer, the term of this patent is extended or adjusted under 35 U.S.C. 154(b) by 101 days.

(21) Appl. No.: 09/729,597

(22) Filed: Dec. 4, 2000

Related U.S. Application Data

(60) Division of application No. 08/907,739, filed on Aug. 8, 1997, now Pat. No. 6,235,469, which is a division of application No. 08/133,011, filed on Jun. 8, 1994, now Pat. No. 5,658,727, which is a continuation-in-part of application No. 07/826,623, filed on Jan. 27, 1992, now abandoned, which is a continuation-in-part of application No. 07/683,602, filed on Apr. 10, 1991, now abandoned.

(51) Int. Cl.$^7$ ................................................ C12Q 1/68
(52) U.S. Cl. .............................. 435/5; 435/6; 435/7.2; 435/235.1; 435/441
(58) Field of Search ....................... 435/5, 6, 7.2, 235.1, 435/441

(56) References Cited

U.S. PATENT DOCUMENTS

| | | | |
|---|---|---|---|
| 5,223,409 | A | 6/1993 | Ladner et al. |
| 5,403,848 | A | 4/1995 | Ladner |
| 5,427,908 | A | 6/1995 | Dower |
| 6,172,197 | B1 | 1/2001 | McCafferty et al. |
| 6,204,023 | B1 | 3/2001 | Robinson et al. |

FOREIGN PATENT DOCUMENTS

| | | |
|---|---|---|
| EP | 0 368 684 | 5/1990 |
| WO | 8806630 | 9/1988 |
| WO | WO 92/01047 | 1/1992 |
| WO | WO 92/06204 | 4/1992 |

OTHER PUBLICATIONS

Siest, et al., Application of gene transfer technologies to the production of enzyme reference materials; example of gamma–glutamyltransferase, 1993, *Clin. Chem.*, 39:1573–1589.
Lane, et al., Epitope mapping using bacteriophage peptide libraries, 1993, *Curr. Opin. Immunol.*, 5:268–271.
Gram, et al., In vitro selection and affinity maturation of antibodies from a native combinatorial immunoglobulin library, 1992, *Proc. Natl. Acad. Sci.*, 89:3576–3580.
Burton, et al., A large array of human monoclonal antibodies to type 1 human immunodeficiency virus from combinatorial libraries of asymptomatic seropositive individuals, 1991, *Proc. Natl. Acad. Sci.*, 88:10134–10137.
Barbas, et al., Assembly of combinatorial antibody libraries on phage surfaces: the gene III site, 1991, *Proc. Natl. Acad. Sci.*, 88:7978–7982.

Kretzschmar, Titus and Geiser, Martin, "Evaluation of Antibodies Fused to Minor Coat Protein III and Major Coat Protein VIII of Bacteriophage M13", *Gene*, 155: 61–65 (1995).
Peters, et al., "Membrane Insertion Defects Caused by Positive Charges in the Early Mature Region of Protein pIII of Filamentous PHage fd Can Be Corrected by prlA Suppressors", *J. of Bacter.*, 176(14): 4296–4305 (1994).
Barbas et al., *Methods: A Companion to Methods in Enzymology*, 2:119–124 (1991).
Huse et al., *Science*, 246:1275–1281 (1989).
Kang et al., *Proc. Natl. Acad. Sci., USA*, 88:4363–4366 (1991).
McCafferty et al., *Nature*, 348:552–554 (1990).
Persson et al., *Proc. Natl. Acad. Sci., USA*, 88:2432–2436 (1991).
Bass et al., *Proteins: Structure, Function and Genetics*, 8:309–314 (1990).
Bird et al., *Science*, 242:423–426 (1988).
Boss et al., *Nucl. Acids Res.*, 12:3791–3806 (1984).
Cabilly et al., *Proc. Natl. Acad. Sci., USA*, 81:3273–3277 (1984).
Caton et al., *Proc. Natl. Acad. Sci., USA*, 87:6450–6454 (1990).
Cwirla et al., *Proc. Natl. Acad. Sci., USA*, 87:6378–6382 (1990).
Il'ichev et al., *Molekulyarnaya Biologiya*, 24:530–535 (1990).
Larrick et al., *Bio/Technology*, 7:934–938 (1989).
Model et al., "The Bacteriophages", ed: R. Calendar, Plenum Publishing Corp., 2:375–456 (1988).
Mullinax et al., *Proc. Natl. Acad. Sci., USA*, 87:8095–8099 (1990).
Orlandi et al., *Proc. Natl. Acad. Sci., USA*, 86:3833–3837 (1989).
Parmely, et al., *Gene*, 73:305–318 (1988).
Pluckthun, *Nature*, 347:497–498 (1990).
Rasched et al., *Microbiol. Rev.*, 50:401–427 (1986).
Sastry et al., *Proc. Natl. Acad. Sci., USA*, 86:572S–5732 (1989).
Scott et al., *Science*, 249:386–390 (1990).
Short et al., *Nuc. Acids Res.*, 16:7583–7600 (1988).
Skerra et al., *Science*, 240:1038–1041 (1988).
Skerra et al., *Bio/Technology*, 9:273–278 (1991).
Smith, G., *Science*, 228:1315–1317 (1985).
Takeda et al., *Nature*, 314:452–454 (1985).
Ward et al., *Nature*, 341:544–546 (1989).
Gussow, et al., *Cold Spring Harbor Symposia on Quantitative Biology*, vol. LIV, p. 265–272 (1989).

*Primary Examiner*—James Ketter
(74) *Attorney, Agent, or Firm*—Emily Holmes; Thomas Fitting

(57) ABSTRACT

Filamentous phage comprising a matrix of cpvIII proteins encapsulating a genome encoding first and second polypeptides of an antogenously assembling receptor, such as an antibody, and a receptor comprised of the first and second polypeptides surface-integrated into the matrix via a filamentous phage coat protein membrane anchor domain fused to at least one of the polypeptides.

15 Claims, 14 Drawing Sheets

SHINE-DALGARNO MET

GGCCGCAAATTCTATTTCAAGGAGACAGTCATAATG
CGTTTAAGATAAAGTTCCTCTGTCAGTATTAC

LEADER SEQUENCE

AAATACCTATTGCCTACGGCAGCCGCT
TTTATGGATAACGGATGCCGTCGGCGA

LEADER SEQUENCE

GGATTGTTATTACTCGCTGCCCAACCAG
CCTAACAATAATGAGCGACGGGTTGGTC

LINKER                    LINKER

| NCOI | $V_H$ BACKBONE | XHOI | SPEI |

CCATGGCCCAGGTGAAACTGCTCGAGATTTCTAGACTAGT
GGTACCGGGTCCACTTTGACGAGCTCTAAAGATCTGATCA

STOP    LINKER

TyrProTyrAspValProAspTyrAlaSer
TACCCGTACGACGTTCCGGACTACGGTTCTTAATAGAATTCG
ATGGGCATGCTGCAAGGCCTGATGCCAAGAATTATCTTAAGCAGCT

FIG. 3

ECOR I          SHINE-DALGARNO    MET

TGAATTCTAAACTAGTCGCCAAGGAGACAGTCATAATGAAAT
TCGAACTTAAGATTTGATCAGCGGTTCCTCTGTCAGTATTACTTTA

LEADER SEQUENCE

ACCTATTGCCTACGGGCAGCCGCTGGATTGTTATTACTCGCTGCCCAACCAG
TGGATAACGGATGCCCGTCGGCGACCTAACAATAATGAGCGACGGGTTGGTC

NCO I  SAC I        XBA I       Not I

CCATGGCCGAGCTCGTCAGTTCTAGAGTTAAGGCCG
GGTACCGGCTCGAGCAGTCAAGATCTCAATTCGGCCCGGCAGCT

| Clone | HCDR3 Sequence | | | | | | | | | | | | | | | | $K_d[F1]$ M | $K_d[F1\text{-}BSA1^*]$ M | SEQ ID NO |
|---|---|---|---|---|---|---|---|---|---|---|---|---|---|---|---|---|---|---|---|
| 7E | G | D | F | W | T | G | Y | S | D | Y | K | Y | A | M | D | V | $<10^{-5}$ | $<10^{-5}$ | 130 |
| F32 | G | G | N | R | M | R | G | L | R | S | R | P | V | M | D | L | $6.0 \times 10^{-7}$ | $1 \times 10^{-7}$ | 131 |
| F34 | G | G | N | R | M | R | G | L | R | S | R | P | V | M | D | L | | | 132 |
| F37 | G | G | N | R | M | R | G | L | R | S | R | P | V | M | D | L | | | 133 |
| F1 | G | V | N | L | F | R | V | N | S | R | P | H | L | M | D | M | $1.4 \times 10^{-7}$ | $2 \times 10^{-8}$ | 134 |
| F7 | G | V | N | L | F | R | V | N | S | R | P | H | L | M | D | M | | | 135 |
| F9 | G | V | N | L | F | R | V | N | S | R | P | H | L | M | D | M | | | 136 |
| F22 | G | V | N | L | F | R | V | N | S | R | P | H | L | M | D | M | | | 137 |
| F25 | G | V | N | L | F | R | V | N | S | R | P | H | L | M | D | M | | | 138 |
| F39 | G | V | N | L | F | R | V | N | S | R | P | H | L | M | D | M | | | 139 |
| F31 | G | G | P | V | S | R | A | L | R | Y | A | G | W | D | L | | $1.3 \times 10^{-6}$ | $3 \times 10^{-8}$ | 140 |
| FBSA-8 | V | A | S | Q | P | R | K | A | P | P | M | F | W | D | P | | $1.5 \times 10^{-6}$ | $5 \times 10^{-8}$ | 141 |
| FBSA-11 | L | L | A | P | L | R | Y | S | L | T | G | G | Y | A | G | L | | $1 \times 10^{-7}$ | 142 |
| FBSA-13 | G | R | G | P | R | R | Y | K | H | G | G | R | A | R | S | Q | | $8 \times 10^{-8}$ | 143 |
| FBSA-20 | S | H | R | G | P | W | S | P | Y | G | G | L | P | A | Y | Q | | $1 \times 10^{-7}$ | 144 |
| FBSA-30 | A | R | T | K | P | R | Q | G | S | R | P | R | Y | V | L | R | $1.6 \times 10^{-6}$ | | 145 |
| FBSA-48 | R | K | P | R | Q | G | S | R | P | R | Y | V | A | L | F | | | | 146 |
| FBSA-55 | L | T | R | W | S | T | L | P | F | P | S | T | L | L | P | L | | | 147 |

STARTING CLONE: 7E
FLUORESCEIN ELUTED CLONES: F32–F31
ACID ELUTED CLONES: FBSA-8 – FBSA-55

| Clone | Light Chain CDR3 Corresponding to Kabat Positions 92-96 | SEQ ID NO |
|---|---|---|
| Starting Clone | | |
| 7E | Gly Ser Ser Leu Trp | 148 |
| Fluorescein Eluted Clones | | |
| p2 | Thr Arg Pro Gly Val | 149 |
| p21 | Thr Arg Pro Gly Val | 149 |
| p23 | Thr Arg Pro Gly Val | 149 |
| p28 | Thr Arg Pro Gly Val | 149 |
| p19 | Thr Arg Pro Gly Val | 149 |
| p15 | Ser Phe Lys Asn Trp | 150 |
| p11 | Gly Tyr Arg Lys Trp | 151 |

SEQUENCE LISTING (1) GENERAL INFORMATION:

(iii) NUMBER OF SEQUENCES: 161

(2) INFORMATION FOR SEQ ID NO: 1:

(i) SEQUENCE CHARACTERISTICS:
      (A) LENGTH: 173 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

```
GGCCGCAAAT TCTATTTCAA GGAGACAGTC ATAATGAAAT ACCTATTGCC TACGGCAGCC        60

GCTGGATTGT TATTACTCGC TGCCCAACCA GCCATGGCCC AGGTGAAACT GCTCGAGATT       120

TCTAGACTAG TTACCCGTAC GACGTTCCGG ACTACGGTTC TTAATAGAAT TCG              173
```

(2) INFORMATION FOR SEQ ID NO: 2:

(i) SEQUENCE CHARACTERISTICS:
      (A) LENGTH: 173 base pairs
      (B) TYPE: nucleic acid
      (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

```
TCGACGAATT CTATTAAGAA CCGTAGTCCG AACGTCGTA CGGGTAACTA GTCTAGAAAT      60

CTCGAGCAGT TTCACCTGGG CCATGGCTGG TTGGGCAGCG AGTAATAACA ATCCAGCGGC    120

TGCCGTAGGC AATAGGTATT TCATTATGAC TGTCTCCTTG AAATAGAATT TGC           173
```

(2) INFORMATION FOR SEQ ID NO: 3:

(i) SEQUENCE CHARACTERISTICS:
       (A) LENGTH: 131 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

```
TGAATTCTAA ACTAGTCGCC AAGGAGACAG TCATAATGAA ATACCTATTG CCTACGGCAG     60

CCGCTGGATT GTTATTACTC GCTGCCCAAC CAGCCATGGC CGAGCTCGTC AGTTCTAGAG    120

TTAAGCGGCC G                                                         131
```

(2) INFORMATION FOR SEQ ID NO: 4:

(i) SEQUENCE CHARACTERISTICS:
       (A) LENGTH: 139 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

```
TCGACGGCCG CTTAACTCTA GAACTGACGA GCTCGGCCAT GGCTGGTTGG GCAGCGAGTA     60

ATAACAATCC AGCGGCTGCC GTAGGCAATA GGTATTTCAT TATGACTGTC TCCTTGGCGA    120

CTAGTTTAGA ATTCAAGCT                                                 139
```

(2) INFORMATION FOR SEQ ID NO: 5:

(i) SEQUENCE CHARACTERISTICS:
       (A) LENGTH: 21 amino acids
       (B) TYPE: amino acid
       (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 5:

Met Lys Tyr Leu Leu Pro Thr Ala Ala Ala Gly Leu Leu Leu Leu Ala

```
            1               5              10              15
Ala Gln Pro Ala Met
            20

(2) INFORMATION FOR SEQ ID NO: 6:

(i) SEQUENCE CHARACTERISTICS:
        (A) LENGTH: 25 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
         (A) ORGANISM: Erwinia carotovora (xi) SEQUENCE DESCRIPTION: SEQ ID NO: 6:

Met Lys Tyr Leu Leu Pro Thr Ala Ala Gly Leu Leu Leu Ala
1               5                  10                  15
Ala Gln Pro Ala Gln Pro Ala Met Ala
            20              25

(2) INFORMATION FOR SEQ ID NO: 7:

(i) SEQUENCE CHARACTERISTICS:
        (A) LENGTH: 22 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
         (A) ORGANISM: Erwinia carotovora (xi) SEQUENCE DESCRIPTION: SEQ ID NO: 7:

Met Lys Ser Leu Ile Thr Pro Ile Ala Ala Gly Leu Leu Ala Phe
1               5                  10                  15
Ser Gln Tyr Ser Leu Ala
            20

(2) INFORMATION FOR SEQ ID NO: 8:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 8:

Met Lys Ile Lys Thr Gly Ala Arg Ile Leu Ala Leu Ser Ala Leu Thr
1               5                  10                  15
Thr Met Met Phe Ser Ala Ser Ala Leu Ala Lys Ile
            20              25

(2) INFORMATION FOR SEQ ID NO: 9:

(i) SEQUENCE CHARACTERISTICS:
```

(A) LENGTH: 24 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 9:

Met Met Lys Arg Asn Ile Leu Ala Val Ile Val Pro Ala Leu Leu Val
1               5                   10                  15

Ala Gly Thr Ala Asn Ala Ala Glu
            20

(2) INFORMATION FOR SEQ ID NO: 10:

(i) SEQUENCE CHARACTERISTICS:
            (A) LENGTH: 23 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 10:

Met Lys Gln Ser Thr Ile Ala Leu Ala Leu Leu Pro Leu Leu Phe Thr
1               5                   10                  15

Pro Val Thr Lys Ala Arg Thr
            20

(2) INFORMATION FOR SEQ ID NO: 11:

(i) SEQUENCE CHARACTERISTICS:
            (A) LENGTH: 25 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 11:

Met Ser Ile Gln His Phe Arg Val Ala Leu Ile Pro Phe Phe Ala Ala
1               5                   10                  15

Phe Cys Leu Pro Val Phe Ala His Pro
            20                  25

(2) INFORMATION FOR SEQ ID NO: 12:

(i) SEQUENCE CHARACTERISTICS:
            (A) LENGTH: 27 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 12:

Met Met Ile Thr Leu Arg Lys Leu Pro Leu Ala Val Ala Val Ala Ala
1               5                   10                  15

Gly Val Met Ser Ala Gln Ala Met Ala Val Asp
            20                  25

(2) INFORMATION FOR SEQ ID NO: 13:

(i) SEQUENCE CHARACTERISTICS:
    (A) LENGTH: 22 amino acids
    (B) TYPE: amino acid
    (D) TOPOLOGY: unknown (ii) MOLECULE TYPE: peptide (iii) HYPOTHETICAL: NO (xi) SEQUENCE DESCRIPTION: SEQ ID NO: 13:

Met Lys Ala Thr Lys Leu Val Leu Gly Ala Val Ile Leu Gly Ser Thr
1               5                   10                  15

Leu Leu Ala Gly Cys Ser
            20

(2) INFORMATION FOR SEQ ID NO: 14:

(i) SEQUENCE CHARACTERISTICS:
        (A) LENGTH: 23 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 14:

Met Lys Lys Ser Leu Val Leu Lys Ala Ser Val Ala Val Ala Thr Leu
1               5                   10                  15

Val Pro Met Leu Ser Phe Ala
            20

(2) INFORMATION FOR SEQ ID NO: 15:

(i) SEQUENCE CHARACTERISTICS:
        (A) LENGTH: 18 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 15:

Met Lys Lys Leu Leu Phe Ala Ile Pro Leu Val Val Pro Phe Tyr Ser
1               5                   10                  15

His Ser (2) INFORMATION FOR SEQ ID NO: 16:

(i) SEQUENCE CHARACTERISTICS:
        (A) LENGTH: 211 amino acids
        (B) TYPE: amino acid
        (D) TOPOLOGY: unknown (ii) MOLECULE TYPE: protein (iii) HYPOTHETICAL: NO (v) FRAGMENT TYPE: internal (xi) SEQUENCE DESCRIPTION: SEQ ID NO: 16:

Pro Phe Val Cys Glu Tyr Gln Gly Gln Gly Gln Ser Ser Asp Leu Pro
1               5                   10                  15

Gln Pro Pro Val Asn Ala Gly Gly Gly Ser Gly Gly Ser Gly Gly
            20                  25                  30

Gly Ser Glu Gly Gly Gly Ser Glu Gly Gly Gly Ser Glu Gly Gly Gly

```
                35                  40                  45
Ser Glu Gly Gly Ser Gly Gly Ser Gly Ser Gly Asp Phe Asp
 50                  55                  60

Tyr Glu Lys Met Ala Asn Ala Asn Lys Gly Ala Met Thr Glu Asn Ala
 65                  70                  75                  80

Asp Glu Asn Ala Leu Gln Ser Asp Ala Lys Gly Lys Leu Asp Ser Val
                 85                  90                  95

Ala Thr Asp Tyr Gly Ala Ala Ile Asp Gly Phe Ile Gly Asp Val Ser
                100                 105                 110

Gly Leu Ala Asn Gly Asn Gly Ala Thr Gly Asp Phe Ala Gly Ser Asn
                115                 120                 125

Ser Gln Met Ala Gln Val Gly Asp Gly Asp Asn Ser Pro Leu Met Asn
                130                 135                 140

Asn Phe Arg Gln Tyr Leu Pro Ser Leu Pro Gln Ser Val Glu Cys Arg
145                 150                 155                 160

Pro Phe Val Phe Ser Ala Gly Lys Pro Tyr Glu Phe Ser Ile Asp Cys
                165                 170                 175

Asp Lys Ile Asn Leu Phe Arg Gly Val Phe Ala Phe Leu Leu Tyr Val
                180                 185                 190

Ala Thr Phe Met Tyr Val Phe Ser Thr Phe Ala Asn Ile Leu Arg Asn
                195                 200                 205

Lys Glu Ser
    210
```

(2) INFORMATION FOR SEQ ID NO: 17:

(i) SEQUENCE CHARACTERISTICS:
        (A) LENGTH: 50 amino acids
        (B) TYPE: amino acid
        (D) TOPOLOGY: unknown (ii) MOLECULE TYPE: protein (iii) HYPOTHETICAL: NO (xi) SEQUENCE DESCRIPTION: SEQ ID NO: 17:

```
Ala Glu Gly Asp Asp Pro Ala Lys Ala Ala Phe Asn Ser Leu Gln Ala
 1               5                  10                  15

Ser Ala Thr Glu Tyr Ile Gly Tyr Ala Trp Ala Met Val Val Val Ile
                20                  25                  30

Val Gly Ala Thr Ile Gly Ile Lys Leu Phe Lys Lys Phe Thr Ser Lys
                35                  40                  45

Ala Ser
 50
```

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 18:

AAUCUUGGAG GCUUUUUUAU GGUUCGUUCU        30

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 19:

UAACUAAGGA UGAAAUGCAU GUCUAAGACA     30

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 20:

UCCUAGGAGG UUUGACCUAU GCGAGCUUUU     30

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 21:

AUGUACUAAG GAGGUUGUAU GGAACAACGC     30

(2) INFORMATION FOR SEQ ID NO: 22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 22:

GGCCGCAAAT TCTATTTCAA GGAGACAGTC AT     32

(2) INFORMATION FOR SEQ ID NO: 23:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 23:

AATGAAATAC CTATTGCCTA CGGCAGCCGC TGGATT                                  36

(2) INFORMATION FOR SEQ ID NO: 24:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 24:

GTTATTACTC GCTGCCCAAC CAGCCATGGC CC                                      32

(2) INFORMATION FOR SEQ ID NO: 25:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 25:

CAGTTTCACC TGGGCCATGG CTGGTTGGG                                          29

(2) INFORMATION FOR SEQ ID NO: 26:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 26:

CAGCGAGTAA TAACAATCCA GCGGCTGCCG TAGGCAATAG                              40

(2) INFORMATION FOR SEQ ID NO: 27:

(i) SEQUENCE CHARACTERISTICS:
            (A) LENGTH: 38 base pairs

```
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 27:

GTATTTCATT ATGACTGTCT CCTTGAAATA GAATTTGC                              38

(2) INFORMATION FOR SEQ ID NO: 28:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 28:

AGGTGAAACT GCTCGAGATT TCTAGACTAG TTACCCGTAC                            40

(2) INFORMATION FOR SEQ ID NO: 29:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 29:

CGGAACGTCG TACGGGTAAC TAGTCTAGAA ATCTCGAG                              38

(2) INFORMATION FOR SEQ ID NO: 30:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 30:

GACGTTCCGG ACTACGGTTC TTAATAGAAT TCG                                   33

(2) INFORMATION FOR SEQ ID NO: 31:

(i) SEQUENCE CHARACTERISTICS:
            (A) LENGTH: 28 base pairs
            (B) TYPE: nucleic acid
            (C) STRANDEDNESS: single
            (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 31:

TCGACGAATT CTATTAAGAA CCGTAGTC                                          28

(2) INFORMATION FOR SEQ ID NO: 32:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 32:

TGAATTCTAA ACTAGTCGCC AAGGAGACAG TCAT                                   34

(2) INFORMATION FOR SEQ ID NO: 33:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 33:

AATGAAATAC CTATTGCCTA CGGCAGCCGC TGGATT                                 36

(2) INFORMATION FOR SEQ ID NO: 34:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 34:

GTTATTACTC GCTGCCCAAC CAGCCATGGC C                                      31

(2) INFORMATION FOR SEQ ID NO: 35:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 35:

GAGCTCGTCA GTTCTAGAGT TAAGCGGCCG                          30

(2) INFORMATION FOR SEQ ID NO: 36:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 36:

GTATTTCATT ATGACTGTCT CCTTGGCGAC TAGTTTAGAA TTCAAGCT        48

(2) INFORMATION FOR SEQ ID NO: 37:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 37:

CAGCGAGTAA TAACAATCCA GCGGCTGCCG TAGGCAATAG                40

(2) INFORMATION FOR SEQ ID NO: 38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 38:

TGACGAGCTC GGCCATGGCT GGTTGGG                              27

(2) INFORMATION FOR SEQ ID NO: 39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 39:

TCGACGGCCG CTTAACTCTA GAAC                                    24

(2) INFORMATION FOR SEQ ID NO: 40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 40:

AGGTSMARCT KCTCGAGTCW GG                                      22

(2) INFORMATION FOR SEQ ID NO: 41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 41:

AGGTCCAGCT GCTCGAGTCT GG                                      22

(2) INFORMATION FOR SEQ ID NO: 42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 42:

AGGTCCAGCT GCTCGAGTCA GG                                      22

(2) INFORMATION FOR SEQ ID NO: 43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 43:

```
AGGTCCAGCT TCTCGAGTCT GG                                              22
```

(2) INFORMATION FOR SEQ ID NO: 44:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 44:

```
AGGTCCAGCT TCTCGAGTCA GG                                              22
```

(2) INFORMATION FOR SEQ ID NO: 45:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 45:

```
AGGTCCAACT GCTCGAGTCT GG                                              22
```

(2) INFORMATION FOR SEQ ID NO: 46:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 46:

```
AGGTCCAACT GCTCGAGTCA GG                                              22
```

(2) INFORMATION FOR SEQ ID NO: 47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 47:

```
AGGTCCAACT TCTCGAGTCT GG                                              22
```

```
(2) INFORMATION FOR SEQ ID NO: 48:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 48:

AGGTCCAACT TCTCGAGTCA GG                                              22

(2) INFORMATION FOR SEQ ID NO: 49:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (D) OTHER INFORMATION:
            /note= "N is the modified base I or inosine."

(xi) SEQUENCE DESCRIPTION: SEQ ID NO: 49:

AGGTNNANCT NCTCGAGTCW GG                                              22

(2) INFORMATION FOR SEQ ID NO: 50:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 50:

GCCCAAGGAT GTGCTCACC                                                  19

(2) INFORMATION FOR SEQ ID NO: 51:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 51:

CTATTAGAAT TCAACGGTAA CAGTGGTGCC TTGGCCCCA                             39
```

(2) INFORMATION FOR SEQ ID NO: 52:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 52:

CTATTAACTA GTAACGGTAA CAGTGGTGCC TTGCCCCA          38

(2) INFORMATION FOR SEQ ID NO: 53:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 53:

CTCAGTATGG TGGTTGTGC          19

(2) INFORMATION FOR SEQ ID NO: 54:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 54:

GCTACTAGTT TTGATTTCCA CCTTGG          26

(2) INFORMATION FOR SEQ ID NO: 55:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 55:

CAGCCATGGC CGACATCCAG ATG          23

(2) INFORMATION FOR SEQ ID NO: 56:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 56:

AATTTTACTA GTCACCTTGG TGCTGCTGGC                                           30

(2) INFORMATION FOR SEQ ID NO: 57:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 57:

TATGCAACTA GTACAACCAC AATCCCTGGG CACAATTTT                                 39

(2) INFORMATION FOR SEQ ID NO: 58:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 58:

AGGCTTACTA GTACAATCCC TGGGCACAAT                                           30

(2) INFORMATION FOR SEQ ID NO: 59:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 59:

CCAGTTCCGA GCTCGTTGTG ACTCAGGAAT CT                                        32

(2) INFORMATION FOR SEQ ID NO: 60:

(i) SEQUENCE CHARACTERISTICS:
        (A) LENGTH: 32 base pairs
        (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 60:

CCAGTTCCGA GCTCGTGTTG ACGCAGCCGC CC                              32

(2) INFORMATION FOR SEQ ID NO: 61:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 61:

CCAGTTCCGA GCTCGTGCTC ACCCAGTCTC CA                              32

(2) INFORMATION FOR SEQ ID NO: 62:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 62:

CCAGTTCCGA GCTCCAGATG ACCCAGTCTC CA                              32

(2) INFORMATION FOR SEQ ID NO: 63:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 63:

CCAGATGTGA GCTCGTGATG ACCCAGACTC CA                              32

(2) INFORMATION FOR SEQ ID NO: 64:

(i) SEQUENCE CHARACTERISTICS:
        (A) LENGTH: 32 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 64:

CCAGATGTGA GCTCGTCATG ACCCAGTCTC CA                32

(2) INFORMATION FOR SEQ ID NO: 65:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 65:

CCAGATGTGA GCTCTTGATG ACCCAAACTC AA                32

(2) INFORMATION FOR SEQ ID NO: 66:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 66:

CCAGATGTGA GCTCGTGATA ACCCAGGATG AA                32

(2) INFORMATION FOR SEQ ID NO: 67:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 67:

GCAGCATTCT AGAGTTTCAG CTCCAGCTTG CC                32

(2) INFORMATION FOR SEQ ID NO: 68:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 68:

CCGCCGTCTA GAACACTCAT TCCTGTTGAA GCT                                33

(2) INFORMATION FOR SEQ ID NO: 69:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 69:

CCGCCGTCTA GAACATTCTG CAGGAGACAG ACT                                33

(2) INFORMATION FOR SEQ ID NO: 70:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 70:

CCAGTTCCGA GCTCGTGATG ACACAGTCTC CA                                 32

(2) INFORMATION FOR SEQ ID NO: 71:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 71:

GCGCCGTCTA GAATTAACAC TCATTCCTGT TGAA                               34

(2) INFORMATION FOR SEQ ID NO: 72:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 72:

CTATTAACTA GTAACGGTAA CAGTGGTGCC TTGCCCCA                                  38

(2) INFORMATION FOR SEQ ID NO: 73:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 73:

AGGCTTACTA GTACAATCCC TGGGCACAAT                                           30

(2) INFORMATION FOR SEQ ID NO: 74:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 74:

GCCGCTCTAG AACACTCATT CCTGTTGAA                                            29

(2) INFORMATION FOR SEQ ID NO: 75:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 75:

AGGTNNANCT NCTCGAGTCT GC                                                   22

(2) INFORMATION FOR SEQ ID NO: 76:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 76:

AGGTNNANCT NCTCGAGTCA GC                                                   22

(2) INFORMATION FOR SEQ ID NO: 77:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 77:

GTGCCAGATG TGAGCTCGTG ATGACCCAGT CTCCA                                      35

(2) INFORMATION FOR SEQ ID NO: 78:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 78:

TCCTTCTAGA TTACTAACAC TCTCCCCTGT TGAA                                       34

(2) INFORMATION FOR SEQ ID NO: 79:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 79:

GCATTCTAGA CTATTATGAA CATTCTGTAG GGGC                                       34

(2) INFORMATION FOR SEQ ID NO: 80:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 80:

CTGCACAGGG TCCTGGGCCG AGCTCGTGGT GACTCAG                                  37

(2) INFORMATION FOR SEQ ID NO: 81:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 81:

AGNTGCANNT GCTCGAGTCT GG                                              22

(2) INFORMATION FOR SEQ ID NO: 82:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 82:

GTGGGCATGT GTGAGTTGTG TCACTAGTTG GGGTTTTGAG CTC                       43

(2) INFORMATION FOR SEQ ID NO: 83:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 83:

AGCATCACTA GTACAAGATT TGGGCTC                                         27

(2) INFORMATION FOR SEQ ID NO: 84:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 84:

AGGTGCAGCT GCTCGAGTCT GG                                              22

(2) INFORMATION FOR SEQ ID NO: 85:

(i) SEQUENCE CHARACTERISTICS:
        (A) LENGTH: 22 base pairs
```

(B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 85:

AGGTGCAGCT GCTCGAGTCG GG                                            22

(2) INFORMATION FOR SEQ ID NO: 86:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 86:

AGGTGCAACT GCTCGAGTCT GG                                            22

(2) INFORMATION FOR SEQ ID NO: 87:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 87:

AGGTGCAACT GCTCGAGTCG GG                                            22

(2) INFORMATION FOR SEQ ID NO: 88:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 88:

TCCTTCTAGA TTACTAACAC TCTCCCCTGT TGAA                               34

(2) INFORMATION FOR SEQ ID NO: 89:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 89:

CTGCACAGGG TCCTGGGCCG AGCTCGTGGT GACTCAG                                     37

(2) INFORMATION FOR SEQ ID NO: 90:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 90:

GCATTCTAGA CTATTAACAT TCTGTAGGGG C                                           31

(2) INFORMATION FOR SEQ ID NO: 91:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 91:

ACCCAAGGAC ACCCTCATG                                                         19

(2) INFORMATION FOR SEQ ID NO: 92:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 92:

CTCAGTATGG TGGTTGTGC                                                         19

(2) INFORMATION FOR SEQ ID NO: 93:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 93:

GTCTCACTAG TCTCCACCAA GGGCCCATCG GTC                                      33

(2) INFORMATION FOR SEQ ID NO: 94:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 94:

ATATACTAGT GAGACAGTGA CCAGGGTTCC TTGGCCCCA                                39

(2) INFORMATION FOR SEQ ID NO: 95:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 95:

ACGTCTAGAT TCCACCTTGG TCCC                                                24

(2) INFORMATION FOR SEQ ID NO: 96:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 96:

GCATACTAGT CTATTAACAT TCTGTAGGGG C                                        31

(2) INFORMATION FOR SEQ ID NO: 97:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 97:

CCGGAATTCT TATCATTTAC CCGGAGA                                               27

(2) INFORMATION FOR SEQ ID NO: 98:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 98:

TCTGCACTAG TTGGAATGGG CACATGCAG                                             29

(2) INFORMATION FOR SEQ ID NO: 99:

(i) SEQUENCE CHARACTERISTICS:
        (A) LENGTH: 798 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 99:

GGCCGCAAAT TCTATTTCAA GGAGACAGTC ATAATGAAAT ACCTATTGCC TACGGCAGCC            60

GCTGGATTGT TATTACTCGC TGCCCAACCA GCCATGGCCC AGGTGAAACT GCTCGAGTCA           120

GGACCTGGCC TCGTGAAACC TTCTCAGTCT CTGTCTCTCA CCTGCTCTGT CACTGACTAC           180

TCCATCACCA GTGCTTATTA CTGGAACTGG ATCCGGCAGT TCCAGGAAA CAAACTGGAA            240

TGGATGGGCT ACATAAGCTA CGACGGTGTC AATAAGTATG ATCCATCTCT CAAGAATCGA           300

ATCTCCATCA CTCGTGACAC ATCTAACAAT CAGTTTTTCC AGAAGTTGAT TTCTGTGACT           360

TCTGAGGACA CAGGAACATA TGACTGTTCA AGAGGGACTA GGGCCTCTGC TATGGACTAC           420

TGGGGTCAAG GAATTTCAGT CACCGTCTCC TCAGCCAAAA CGACACCCCC ATCTGTCTAT           480

CCACTGGCCC CTGGATCTGC TGCCCAAACT AACTCCATGG TGACCCTGGG ATGCCTGGTC           540

AAGGGCTATT TCCCTGAGCC AGTGACAGTG ACCTGGAACT CTGGATCCCT GTCCAGCGGT           600

GTGCACACCT TCCCAGCTGT CCTGCAGTCT GACCTCTACA CTCTGAGCAG CTCAGTGACT           660

GTCCCCTCCA GCCCTCGGCC CAGCGAGACC GTCACCTGCA ACGTTGCCCA CCCGGCCAGC           720

AGCACCAAGG TGGACAAGAA AATTGTGCCC AGGGATTGTA CTAGTTACCC GTACGACGTT           780

CCGGACTACG GTTCTTAA                                                        798

(2) INFORMATION FOR SEQ ID NO: 100:

(i) SEQUENCE CHARACTERISTICS:
        (A) LENGTH: 194 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 100:

| | |
|---|---|
| TGAATTCTAA ACTAGTCGCC AAGGAGACAG TCATAATGAA ATACCTATTG CCTACGGCAG | 60 |
| CCGCTGGATT GTTACTCGCT GCCCAACCAG CCATGGCCGA GCTCCAGATG ACCCAGTCTC | 120 |
| CAGCCTCCCT ATCTGCATCT GTGGGAGAAA CTGTCACCAT CACATGTCGA TCAAGTGAGA | 180 |
| ATATTACAAT TACT | 194 |

(2) INFORMATION FOR SEQ ID NO: 101:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 101:

| | |
|---|---|
| CTGATGCTGC ACCAACTGTA TCCATCTTCC CACCATCCAG TGAGCAGTTA ACATCTGGAG | 60 |
| GTGCCTCAGT CGTGTGCTTC TTGAACAACT TCTACCCCAA AGACTACAAT GTCAAGGGGA | 120 |
| AGATTGATGG CAGTGAACGA CAAAATGGCG TCCTGAACAG TTGGACTGAT CAGGACAGCA | 180 |
| AAGACAGCAC CTACAGCATG AGCAGCACCC TCACGTTGAC CAAGGACGAG TATGAACGAC | 240 |
| ATAACAGCTA TACCTGTGAT GCCACTCACA AGACATCAAC TTCACCCATT GTCAAGAGCT | 300 |
| TCAACAGGAA TGAGTGTTAA TTCTAGACGG CGC | 333 |

(2) INFORMATION FOR SEQ ID NO: 102:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 102:

| | |
|---|---|
| GCTGAGGGTG ACGATCCCGC AAAAGCGGCC TTTAACTCCC TGCAAGCCTC AGCGACCGAA | 60 |
| TATATCGGTT ATGCGTGGGC GATGGTTGTT GTCATTGTCG GCGCAACTAT CGGTATCAAG | 120 |
| CTGTTTAAGA AATTCACCTC GAAAGCAAGC | 150 |

(2) INFORMATION FOR SEQ ID NO: 103:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 103:

GTGCCCAGGG ATTGTACTAG TGCTGAGGGT GACGAT                36

(2) INFORMATION FOR SEQ ID NO: 104:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 104:

ACTCGAATTC TATCAGCTTG CTTTCGAGGT GAA                    33

(2) INFORMATION FOR SEQ ID NO: 105:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 105:

AGGTCCAGCT TCTCGAGTCT GG                                22

(2) INFORMATION FOR SEQ ID NO: 106:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 106:

GTCACCCTCA GCACTAGTAC AATCCCTGGG CAC                    33

(2) INFORMATION FOR SEQ ID NO: 107:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 107:

GAGACGACTA GTGGTGGCGG TGGCTCTCCA TTCGTTTGTG AATATCAA                          48

(2) INFORMATION FOR SEQ ID NO: 108:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 108:

TTACTAGCTA GCATAATAAC GGAATACCCA AAAGAACTGG                                   40

(2) INFORMATION FOR SEQ ID NO: 109:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 109:

TATGCTAGCT AGTAACACGA CAGGTTTCCC GACTGG                                       36

(2) INFORMATION FOR SEQ ID NO: 110:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 110:

ACCGAGCTCG AATTCGTAAT CATGGTC                                                 27

(2) INFORMATION FOR SEQ ID NO: 111:

(i) SEQUENCE CHARACTERISTICS:
        (A) LENGTH: 186 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 111:

GTGCCCAGGG ATTGTACTAG TGCTGAGGGT GACGATCCCG CAAAAGCGGC CTTTAACTCC             60

```
CTGCAAGCCT CAGCGACCGA ATATATCGGT TATGCGTGGG CGATGGTTGT TGTCATTGTC         120

GGCGCAACTA TCGGTATCAA GCTGTTTAAG AAATTCACCT CGAAAGCAAG CTGATAGAAT         180

TCGAGT                                                                   186
```

(2) INFORMATION FOR SEQ ID NO: 112:

(i) SEQUENCE CHARACTERISTICS:
        (A) LENGTH: 666 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 112:

```
CCATTCGTTT GTGAATATCA AGGCCAAGGC CAATCGTCTG ACCTGCCTCA ACCTCCTGTC          60

AATGCTGGCG GCGGCTCTGG TGGTGGTTCT GGTGGCGGCT CTGAGGGTGG TGGCTCTGAG         120

GGTGGCGGTT CTGAGGGTGG CGGCTCTGAG GGAGGCGGTT CCGGTGGTGG CTCTGGTTCC         180

GGTGATTTTG ATTATGAAAA GATGGCAAAC GCTAATAAGG GGGCTATGAC CGAAAATGCC         240

GATGAAAACG CGCTACAGTC TGACGCTAAA GGCAAACTTG ATTCTGTCGC TACTGATTAC         300

GGTGCTGCTA TCGATGGTTT CATTGGTGAC GTTTCCGGCC TTGCTAATGG TAATGGTGCT         360

ACTGGTGATT TTGCTGGCTC TAATTCCCAA ATGGCTCAAG TCGGTGACGG TGATAATTCA         420

CCTTTAATGA ATAATTTCCG TCAATATTTA CCTTCCCTCC CTCAATCGGT TGAATGTCGC         480

CCTTTTGTCT TTAGCGCTGG TAAACCATAT GAATTTTCTA TTGATTGTGA CAAAATAAAC         540

TTATTCGGTG TCTTTGCGTT TCTTTTATAT GTTGCCACCT TTATGTATGT ATTTTCTACG         600

TTTGCTAACA TACTGCGTAA TAAGGAGTCT TAATCATGCC AGTTCTTTTG GGTATTCCGT         660

TATTAT                                                                   666
```

(2) INFORMATION FOR SEQ ID NO: 113:

(i) SEQUENCE CHARACTERISTICS:
        (A) LENGTH: 708 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 113:

```
GAGACGACTA GTGGTGGCGG TGGCTCTCCA TTCGTTTGTG AATATCAAGG CCAAGGCCAA          60

TCGTCTGACC TGCCTCAACC TCCTGTCAAT GCTGGCGGCG GCTCTGGTGG TGGTTCTGGT         120

GGCGGCTCTG AGGGTGGTGG CTCTGAGGGT GGCGGTTCTG AGGGTGGCGG CTCTGAGGGA         180

GGCGGTTCCG GTGGTGGCTC TGGTTCCGGT GATTTTGATT ATGAAAAGAT GGCAAACGCT         240

AATAAGGGGG CTATGACCGA AAATGCCGAT GAAAACGCGC TACAGTCTGA CGCTAAAGGC         300

AAACTTGATT CTGTCGCTAC TGATTACGGT GCTGCTATCG ATGGTTTCAT TGGTGACGTT         360

TCCGGCCTTG CTAATGGTAA TGGTGCTACT GGTGATTTTG CTGGCTCTAA TTCCCAAATG         420
```

```
GCTCAAGTCG GTGACGGTGA TAATTCACCT TTAATGAATA ATTTCCGTCA ATATTTACCT      480

TCCCTCCCTC AATCGGTTGA ATGTCGCCCT TTTGTCTTTA GCGCTGGTAA ACCATATGAA      540

TTTTCTATTG ATTGTGACAA AATAAACTTA TTCCGTGGTG TCTTTGCGTT TCTTTTATAT      600

GTTGCCACCT TTATGTATGT ATTTTCTACG TTTGCTAACA TACTGCGTAA TAAGGAGTCT      660

TAATCATGCC AGTTCTTTTG GGTATTCCGT TATTATGCTA GCTAGTAA                   708

(2) INFORMATION FOR SEQ ID NO: 114:

(i) SEQUENCE CHARACTERISTICS:
        (A) LENGTH: 201 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 114:

TATGCTAGCT AGTAACACGA CAGGTTTCCC GACTGGAAAG CGGGCAGTGA GCGCAACGCA       60

ATTAATGTGA GTTAGCTCAC TCATTAGGCA CCCCAGGCTT TACACTTTAT GCTTCCGGCT      120

CGTATGTTGT GTGGAATTGT GAGCGGATAA CAATTTCACA CAGGAAACAG CTATGACCAT      180

GATTACGAAT TCGAGCTCGG T                                                201

(2) INFORMATION FOR SEQ ID NO: 115:

(i) SEQUENCE CHARACTERISTICS:
        (A) LENGTH: 830 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 115:

AGGTCCAGCT TCTCGAGTCT GGACCTGGCC TCGTGAAACC TTCTCAGTCT CTGTCTCTCA       60

CCTGCTCTGT CACTGACTAC TCCATCACCA GTGCTTATTA CTGGAACTGG ATCCGGCAGT      120

TTCCAGGAAA CAAACTGGAA TGGATGGGCT ACATAAGCTA CGACGGTGTC AATAAGTATG      180

ATCCATCTCT CAAGAATCGA ATCTCCATCA CTCGTGACAC ATCTAACAAT CAGTTTTTCC      240

AGAAGTTGAT TTCTGTGACT TCTGAGGACA CAGGAACATA TGACTGTTCA AGAGGGACTA      300

GGGCCTCTGC TATGGACTAC TGGGGTCAAG GAATTTCAGT CACCGTCTCC TCAGCCAAAA      360

CGACACCCCC ATCTGTCTAT CCACTGGCCC CTGGATCTGC TGCCCAAACT AACTCCATGG      420

TGACCCTGGG ATGCCTGGTC AAGGGCTATT TCCCTGAGCC AGTGACAGTG ACCTGGAACT      480

CTGGATCCCT GTCCAGCGGT GTGCACACCT TCCCAGCTGT CCTGCAGTCT GACCTCTACA      540

CTCTGAGCAG CTCAGTGACT GTCCCCTCCA GCCCTCGGCC CAGCGAGACC GTCACCTGCA      600

ACGTTGCCCA CCCGGCCAGC AGCACCAAGG TGGACAAGAA AATTGTGCCC AGGGATTGTA      660

CTAGTGCTGA GGGTGACGAT CCCGCAAAAG CGGCCTTTAA CTCCCTGCAA GCCTCAGCGA      720

CCGAATATAT CGGTTATGCG TGGGCGATGG TTGTTGTCAT TGTCGGCGCA ACTATCGGTA      780

TCAAGCTGTT TAAGAAATTC ACCTCGAAAG CAAGCTGATA GAATTCGAGT                 830
```

(2) INFORMATION FOR SEQ ID NO: 116:

(i) SEQUENCE CHARACTERISTICS:
        (A) LENGTH: 260 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 116:

```
ATGAAATACC TATTGCCTAC GGCAGCCGCT GGATTGTTAT TACTCGCTGC CCAACCAGCC      60

ATGGCCCAGG TGAAACTGCT CGAGATTTCT AGACTAGTGC TGAGGGTGAC GATCCCGCAA     120

AAGCGGCCTT TAACTCCCTG CAAGCCTCAG CGACCGAATA TATCGGTTAT GCGTGGGCGA     180

TGGTTGTTGT CATTGTCGGC GCAACTATCG GTATCAAGCT GTTTAAGAAA TTCACCTCGA     240

AAGCAAGCTG ATAGAATTCG                                                 260
```

(2) INFORMATION FOR SEQ ID NO: 117:

(i) SEQUENCE CHARACTERISTICS:
        (A) LENGTH: 461 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 117:

```
GTACGCGCCC TGTAGCGGCG CATTAAGCGC GGCGGGTGTG GTGGTTACGC GCAGCGTGAC      60

CGCTACACTT GCCAGCGCCC TAGCGCCCGC TCCTTTTGCT TTCTTCCCTT CCTTTCTCGC     120

CACGTTCGCC GGCTTTCCCC GTCAAGCTCT AAATCGGGGG CTCCCTTTAG GGTTCCGATT     180

TAGTGCTTTA CGGCACCTCG ACCCCAAAAA ACTTGATTAG GGTGATGGTT CACGTAGTGG     240

GCCATCGCCC TGATAGACGG TTTTTCGCCC TTTGACGTTG GAGTCCACGT TCTTTAATAG     300

TGGACTCTTG TTCCAAACTG AACAACACT  CAACCCTATC TCGGTCTATT CTTTTGATTT     360

ATAAGGGATT TTGCCGATTT CGGCCTATTG GTTAAAAAAT GAGCTGATTT AACAAAAATT     420

TAACGCGAAT TTTAACAAAA TATTAACGTT TACAATTTAA A                         461
```

(2) INFORMATION FOR SEQ ID NO: 118:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 118:

```
GCAATAAACC CTCACTAAAG GG                                               22
```

(2) INFORMATION FOR SEQ ID NO: 119:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 119:

TCTCGCACAA TAATACACGG C                                        21

(2) INFORMATION FOR SEQ ID NO: 120:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 120:

GTGTATTATT GTGCGAGANN SNNSNNSNNS NNSNNSNNSN NSNNSNNSNN SNNSNNSNNS    60

NNSNNSTGGG GCCAAGGGAC CACG                                        84

(2) INFORMATION FOR SEQ ID NO: 121:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 121:

GCATGTACTA GTTTTGTCAC AAGATTTGGG                                30

(2) INFORMATION FOR SEQ ID NO: 122:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 122:

TGGGGCCAAG GGACCACG                                                    18

(2) INFORMATION FOR SEQ ID NO: 123:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 123:

GTGTATTATT GTGCGAGA                                                  18

(2) INFORMATION FOR SEQ ID NO: 124:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: repeat_region
        (B) LOCATION: 19..21
        (D) OTHER INFORMATION: /rpt_type= "tandem"
            /note= "NNB can be repeated from 3 to about 24
            times."

(xi) SEQUENCE DESCRIPTION: SEQ ID NO: 124:

GTGTATTATT GTGCGAGANN BTGGGGCCAA GGGACCACG                        39

(2) INFORMATION FOR SEQ ID NO: 125:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 125:

AGCTGTTGAA TTCGTGAAAT TGTTATCCGC T                                 31

(2) INFORMATION FOR SEQ ID NO: 126:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 126:

GAATTCTAAA CTAGCTAGTC G                                         21

(2) INFORMATION FOR SEQ ID NO: 127:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 127:

ATACTGCTGA CAGTAATACA C                                         21

(2) INFORMATION FOR SEQ ID NO: 128:

(i) SEQUENCE CHARACTERISTICS:
       (A) LENGTH: 51 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 128:

TATTACTGTC AGCAGTATNN KNNKNNKNNK NNKACTTTCG GCGGAGGGAC C         51

(2) INFORMATION FOR SEQ ID NO: 129:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 129:

AATACGACTC ACTATAGGGC G                                         21

(2) INFORMATION FOR SEQ ID NO: 130:

(i) SEQUENCE CHARACTERISTICS:
       (A) LENGTH: 16 amino acids
       (B) TYPE: amino acid
       (D) TOPOLOGY: linear (ii) MOLECULE TYPE: protein (v) FRAGMENT TYPE: internal (xi) SEQUENCE DESCRIPTION: SEQ ID NO: 130:

Gly Asp Phe Trp Thr Gly Tyr Ser Asp Tyr Lys Tyr Ala Met Asp Val
1               5                  10                  15

(2) INFORMATION FOR SEQ ID NO: 131:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 131:

Gly Asn Arg Met Arg Gly Leu Arg Ser Arg Pro Val Met Met Asp Leu
1               5                   10                  15

(2) INFORMATION FOR SEQ ID NO: 132:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 132:

Gly Asn Arg Met Arg Gly Leu Arg Ser Arg Pro Val Met Met Asp Leu
1               5                   10                  15

(2) INFORMATION FOR SEQ ID NO: 133:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 133:

Gly Asn Arg Met Arg Gly Leu Arg Ser Arg Pro Val Met Met Asp Leu
1               5                   10                  15

(2) INFORMATION FOR SEQ ID NO: 134:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 134:

Gly Val Asn Leu Phe Arg Val Arg Asn Ser Arg Pro His Leu Asp Met
1               5                   10                  15

(2) INFORMATION FOR SEQ ID NO: 135:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 135:

Gly Val Asn Leu Phe Arg Val Arg Asn Ser Arg Pro His Leu Asp Met
1               5                   10                  15

(2) INFORMATION FOR SEQ ID NO: 136:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 136:

Gly Val Asn Leu Phe Arg Val Arg Asn Ser Arg Pro His Leu Asp Met
1               5                   10                  15

(2) INFORMATION FOR SEQ ID NO: 137:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 137:

Gly Val Asn Leu Phe Arg Val Arg Asn Ser Arg Pro His Leu Asp Met
1               5                   10                  15

(2) INFORMATION FOR SEQ ID NO: 138:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 138:

Gly Val Asn Leu Phe Arg Val Arg Asn Ser Arg Pro His Leu Asp Met
1               5                   10                  15

(2) INFORMATION FOR SEQ ID NO: 139:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 139:

Gly Val Asn Leu Phe Arg Val Arg Asn Ser Arg Pro His Leu Asp Met
1               5                   10                  15

(2) INFORMATION FOR SEQ ID NO: 140:

(i) SEQUENCE CHARACTERISTICS:
        (A) LENGTH: 16 amino acids
        (B) TYPE: amino acid

```
            (D) TOPOLOGY: linear (ii) MOLECULE TYPE: protein (v) FRAGMENT TYPE: internal (xi) SEQUENCE DESCRIPTION: SEQ ID NO: 140:

Gly Gly Pro Val Ser Arg Ala Leu Arg Arg Tyr Ala Gly Trp Asp Leu
1               5                  10                  15

(2) INFORMATION FOR SEQ ID NO: 141:

(i) SEQUENCE CHARACTERISTICS:
            (A) LENGTH: 16 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO: 141:

Val Ala Ser Gln Val Pro Gln Arg Ala Lys Arg Pro Met Phe Trp Asp
1               5                  10                  15

(2) INFORMATION FOR SEQ ID NO: 142:

(i) SEQUENCE CHARACTERISTICS:
            (A) LENGTH: 16 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO: 142:

Phe Leu Ala Phe Arg Leu Tyr Arg Lys Pro Leu Pro Arg Ala Gly Leu
1               5                  10                  15

(2) INFORMATION FOR SEQ ID NO: 143:

(i) SEQUENCE CHARACTERISTICS:
            (A) LENGTH: 16 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO: 143:

Gly Leu Pro His Gly Arg Gly Trp Ser Phe Thr Arg Gln Ala Pro Ser
1               5                  10                  15

(2) INFORMATION FOR SEQ ID NO: 144:

(i) SEQUENCE CHARACTERISTICS:
            (A) LENGTH: 16 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO: 144:

Leu Arg Gly Trp Pro Leu Ser Pro Tyr Gln Gly Tyr Arg Arg Ser Gln
1               5                  10                  15
```

(2) INFORMATION FOR SEQ ID NO: 145:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 145:

```
Ser His Asn Ser Trp Pro Arg Tyr Arg Thr Gly Val Gly Tyr Ser Arg
1               5                   10                  15
```

(2) INFORMATION FOR SEQ ID NO: 146:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 146:

```
Leu Arg Thr Leu Gln Arg Ser Gln Gly Arg Phe Ala Phe Arg Asn Ala
1               5                   10                  15
```

(2) INFORMATION FOR SEQ ID NO: 147:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 147:

```
Ser Ala Arg Lys Pro Phe Arg Trp Ser Thr Pro Phe Pro Ser Thr Leu
1               5                   10                  15
```

(2) INFORMATION FOR SEQ ID NO: 148:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 148:

```
Gly Ser Ser Leu Trp
1               5
```

(2) INFORMATION FOR SEQ ID NO: 149:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 149:

Thr Arg Pro Gly Val
1               5

(2) INFORMATION FOR SEQ ID NO: 150:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 150:

Ser Phe Lys Asn Trp
1               5

(2) INFORMATION FOR SEQ ID NO: 151:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 151:

Gly Tyr Arg Lys Trp
1               5

(2) INFORMATION FOR SEQ ID NO: 152:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 152:

ATTGGGACTA GTTTCTGCGA CAGCTGGAAT                                           30

(2) INFORMATION FOR SEQ ID NO: 153:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 153:

GCGCCGTCTA GAATTAACAC TCATTCCTGT TGAA                                      34

(2) INFORMATION FOR SEQ ID NO: 154:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 154:

```
TCGAGAAAGT CTCTAGAGGT AAATCTTCTG GTTCTGGTTC CGAATCTAAA TCTACTGAGC      60

TCAAAGTCA                                                              69
```

(2) INFORMATION FOR SEQ ID NO: 155:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 155:

```
CTAGTGACTT TGAGCTCAGT AGATTTAGAT TCGGAACCAG AACCAGAAGA TTTACCTCTA      60

GAGACTTTC                                                              69
```

(2) INFORMATION FOR SEQ ID NO: 156:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 156:

```
ATTTGGGAAG GACTGTCTAG ATGMRGAGAC                                       30
```

(2) INFORMATION FOR SEQ ID NO: 157:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 157:

```
GAGGACTAGT TACAGTTGGT GCAGCATCAG                                       30
```

(2) INFORMATION FOR SEQ ID NO: 158:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 158:

CTAGTTAACT GAGTAAG                                                17

(2) INFORMATION FOR SEQ ID NO: 159:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 159:

AATTCTTACT CAGTTAA                                                17

(2) INFORMATION FOR SEQ ID NO: 160:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 160:

AACAGCTATG ACCATG                                                 16

(2) INFORMATION FOR SEQ ID NO: 161:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 161:

GACAGGAGGT TGAGGCAGGT                                             20

HETERODIMERIC RECEPTOR LIBRARIES USING PHAGEMIDS

This application is a divisional application of Ser. No. 08/907,739, filed Aug. 8, 1997, now U.S. Pat. No. 6,235,469 which is a divisional application of Ser. No. 08/133,011, filed Jun. 8, 1994, now U.S. Pat. No. 5,658,727, which is a continuation-in-part aplication of Ser. No. 07/826,623, filed Jan. 27, 1992, now abandoned, which is a continuation-in-part of Ser. No. 07/683,602, filed Apr. 10, 1991, now abandoned, whose disclosures are incorporated herein by reference.

This invention was made with United States government support under Grant No. CA 27489 awarded by the National Institutes of Health. The United States Government may have certain rights in the invention.

TECHNICAL FIELD

The present invention relates to cloning vectors and methods for producing a library of DNA molecules capable of expressing a fusion polypeptide on the surface of a filamentous phage particle.

BACKGROUND

Filamentous bacteriophages are a group of related viruses that infect bacteria. They are termed filamentous because they are long and thin particles comprised of an elongated capsule that envelopes the deoxyribonucleic acid (DNA) that forms the bacteriophage genome. The F pili filamentous bacteriophage (Ff phage) infect only gram-negative bacteria by specifically adsorbing to the tip of F pili, and include fd, f1 and M13.

The mature capsule of Ff phage is comprised of a coat of five phage-encoded gene products: cpVIII, the major coat protein product of gene VIII that forms the bulk of the capsule; and four minor coat proteins, cpIII and cpIV at one end of the capsule and cpVII and cpIX at the other end of the capsule. The length of the capsule is formed by 2500 to 3000 copies of cpVIII in an ordered helix array that forms the characteristic filament structure. About five copies each of the minor coat proteins are present at the ends of the capsule. The gene III-encoded protein (cpIII) is typically present in 4 to 6 copies at one end of the capsule and serves as the receptor for binding of the phage to its bacterial host in the initial phase of infection. For detailed reviews of Ff phage structure, see Rasched et al., Microbiol. Rev., 50:401–427 (1986); and Model et al., in "The Bacteriophages, Volume 2", R. Calendar, Ed., Plenum Press, pp. 375–456 (1988).

The assembly of a Ff phage particle involves highly complex mechanics. No phage particles are assembled within a host cell; rather, they are assembled during extrusion of the viral genome through the host cell's membrane. Prior to extrusion, the major coat protein cpVIII and the minor coat protein cpIII are synthesized and transported to the host cell's membrane. Both cpVIII and cpIII are anchored in the host cell membrane prior to their incorporation into the mature particle. In addition, the viral genome is produced and coated with cpV protein. During the extrusion process, cpV-coated genomic DNA is stripped of the cpV coat and simultaneously re-coated with the mature coat proteins. The assembly mechanisms that control transferral of these proteins from the membrane to the particle is not presently known.

Both cpIII and cpVIII proteins include two domains that provide signals for assembly of the mature phage particle. The first domain is a secretion signal that directs the newly synthesized protein to the host cell membrane. The secretion signal is located at the amino terminus of the polypeptide and targets the polypeptide at least to the cell membrane. The second domain is a membrane anchor domain that provides signals for association with the host cell membrane and for association with the phage particle during assembly. This second signal for both cpVIII and cpIII comprises at least a hydrophobic region for spanning the membrane.

cpVIII has been extensively studied as a model membrane protein because it can integrate into lipid bilayers such as the cell membrane in an asymmetric orientation with the acidic amino terminus toward the outside and the basic carboxy terminus toward the inside of the membrane. The mature protein is about 50 amino acid residues in length of which 11 residues provide the carboxy terminus, 19 residues provide the hydrophobic transmembrane region, and the remaining residues comprise the amino terminus. Considerable research has been done on the secretion signal region of cpVIII to advance the study of membrane protein synthesis and targeting to membranes. However, little is known about the changes that are tolerated in the structure of the cpVIII membrane anchor region that would allow for assembly of phage particles.

Manipulation of the sequence of cpIII shows that the C-terminal 23 amino acid residue stretch of hydrophobic amino acids normally responsible for a membrane anchor function can be altered in a variety of ways and retain the capacity to associate with membranes. However, those anchor-modified cpIII proteins lost their ability to genetically complement gene III mutants indicating that the requirements of a membrane anchor for functional assembly have not been elucidated.

Ff phage-based expression vectors have been described in which the entire cpIII amino acid residue sequence was modified by insertion of short polypeptide "epitopes" [Parmely et al., Gene, 73:305–318 (1988); and Cwirla et al., Proc. Natl. Acad. Sci. USA, 87:6378–6382 (1990)] or an amino acid residue sequence defining a single chain antibody domain. McCafferty et al., Science, 348:552–554 (1990). These hybrid proteins were synthesized and assembled onto phage particles in amounts of about 5 copies per particle, a density at which normal cpIII is usually found. However, these expressed fusion proteins include the entire cpIII amino acid residue sequence and do not suggest fusion proteins that utilize only the carboxy terminal membrane anchor domain of cpIII.

In addition, no expression system has been described in which a phage coat protein has been engineered to allow assembly of a heterodimeric molecule that is functional and capable of incorporation into the coat of a phage particle.

BRIEF SUMMARY OF THE INVENTION

A new surface-integration technology has been discovered for expressing a heterodimeric recombinant gene product on the surface of a filamentous phage containing the recombinant gene. The invention uses a filamentous phage coat protein membrane anchor domain as a means for linking gene-product and gene during the assembly stage of filamentous phage replication.

That is, during filamentous phage replication, coat proteins assemble into a matrix which encapsulates the phage genome. It has now been discovered that (1) phage assembly is not disrupted when recombinant filamentous phage coat proteins are present, (2) recombinant filamentous phage coat proteins can be integrated into the assembling matrix, and (3) integration into the matrix can be directed to occur in a surface-accessible orientation.

The present invention can be advantageously applied to the production of heterodimeric receptors of predetermined specificity, i.e., it can be used to produce antibodies, T-cell receptors and the like that bind a preselected ligand.

Thus, the present invention provides for linking the functions of heterodimeric receptor recognition and filamentous phage replication in a method for isolating a heterodimeric receptor and the gene that encodes receptor. The method produces a filamentous phage comprised of a matrix of gene VIII-encoded proteins that encapsulate a recombinant genome. The recombinant genome contains genes encoding the heterodimeric receptor polypeptides. The heterodimeric receptor is surface-integrated into the encapsulating matrix via a filamentous phage coat protein's membrane anchor domain that is fused by a peptide bond during translation to one of the heterodimeric receptor polypeptides. The heterodimeric receptor polypeptides and the genes which encode the polypeptides are physically linked during the assembly stage of the phage replication cycle. Specifically binding the receptor-coated phage to a solid-support advantageously provides a means for isolating a recombinant genome that encodes a desired heterodimeric receptor from a diverse library of recombinant genomes.

In one embodiment, the present invention contemplates an antibody molecule comprising heavy- and light-chain polypeptides, said heavy-chain polypeptide comprising a $V_H$-domain flanked by an amino-terminal prokaryotic secretion signal domain and a carboxy-terminal filamentous phage membrane anchor domain, said light chain polypeptide comprising a $V_L$-domain fused to an amino-terminal prokaryotic secretion signal domain.

In another embodiment, the present invention contemplates a vector for expressing a fusion polypeptide, said vector comprising upstream and downstream translatable DNA sequences operatively linked via a sequence of nucleotides adapted for directional ligation of an insert DNA, said upstream sequence encoding a prokaryotic secretion signal, said downstream sequence encoding a filamentous phage membrane anchor, said translatable DNA sequences operatively linked to a set of DNA expression signals for expression of said translatable DNA sequences as portions of said fusion polypeptide.

BRIEF DESCRIPTION OF THE DRAWINGS

In the drawings forming a portion of this disclosure:

FIGS. 2B-1 and 2B-2 are diagrammatic sketches of a human light (Kappa) chain (Panel 1). Numbering is from the N-terminus on the left to the C-terminus on the right. Note the intrachain disulfide bond (S—S) spanning about the same number of amino acid residues in the $V_L$ and $C_L$ domains. Panel 2 shows the locations of the complementarity-determining regions (CDR) in the $V_L$ domain. Segments outside the CDR are the framework segments (FR).

FIG. 3 illustrates the sequence of the double-stranded synthetic DNA inserted into Lambda Zap to produce a Lambda Hc2 expression vector. The preparation of the double-stranded synthetic DNA insert is described in Example 1a(ii). The various features required for this vector to express the $V_H$-coding DNA homologs include the Shine-Dalgarno ribosome binding site, a leader sequence to direct the expressed protein to the periplasm as described by Mouva et al., J. Biol. Chem., 255:27, 1980, and various restriction enzyme sites used to operatively link the $V_H$ homologs to the expression vector. The $V_H$ expression vector sequence also contains a short nucleic acid sequence that codes for amino acids typically found in variable regions heavy chain ($V_H$ backbone). This $V_H$ backbone is just upstream and in the proper reading as the $V_H$ DNA homologs that are operatively linked into the Xho I and Spe I cloning sites. The sequences of the top and bottom strands of the double-stranded synthetic DNA insert are listed respectively as SEQ ID NO 1 and SEQ ID NO 2. The synthetic DNA insert is directionally ligated into Lambda Zap II digested with the restriction enzymes Not 1 and Xho I to form Lambda Hc2 expression vector.

FIG. 5 illustrates the sequence of the double-stranded synthetic DNA inserted into Lambda Zap to produce a Lambda Lc2 expression vector. The various features required for this vector to express the $V_L$-coding DNA homologs are described in FIG. 3. The $V_L$-coding DNA homologs are operatively linked into the Lc2 sequence at the Sac I and Xho I restriction sites. The sequences of the top and bottom strands of the double-stranded synthetic DNA insert are listed respectively as SEQ ID NO 3 and SEQ ID NO 4. The synthetic DNA insert is directionally ligated into Lambda Zap II digested with the restriction enzymes Sac I and Not I to form Lambda Lc2 expression vector.

Figure 8:
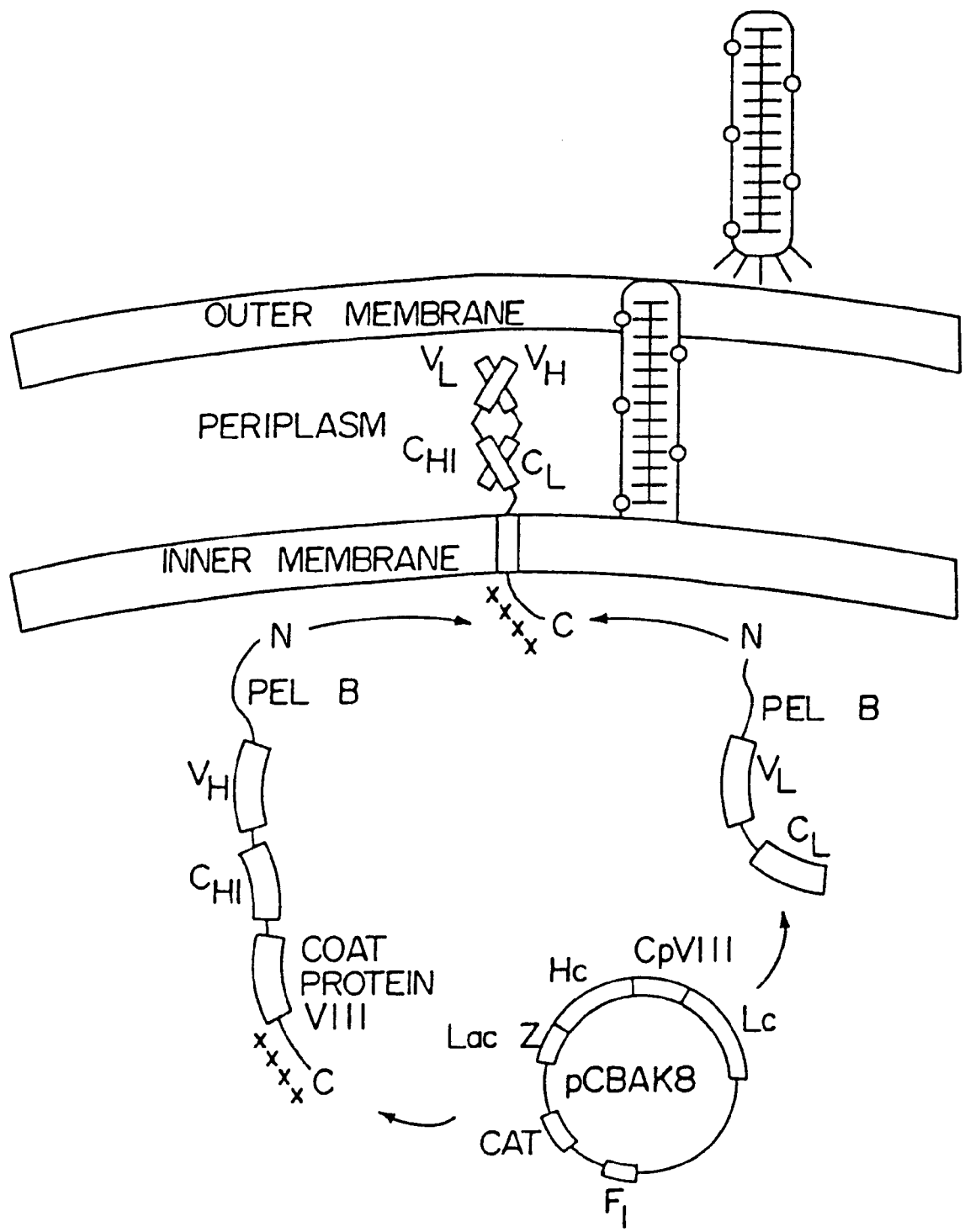
Figures 1, 2, 9A:
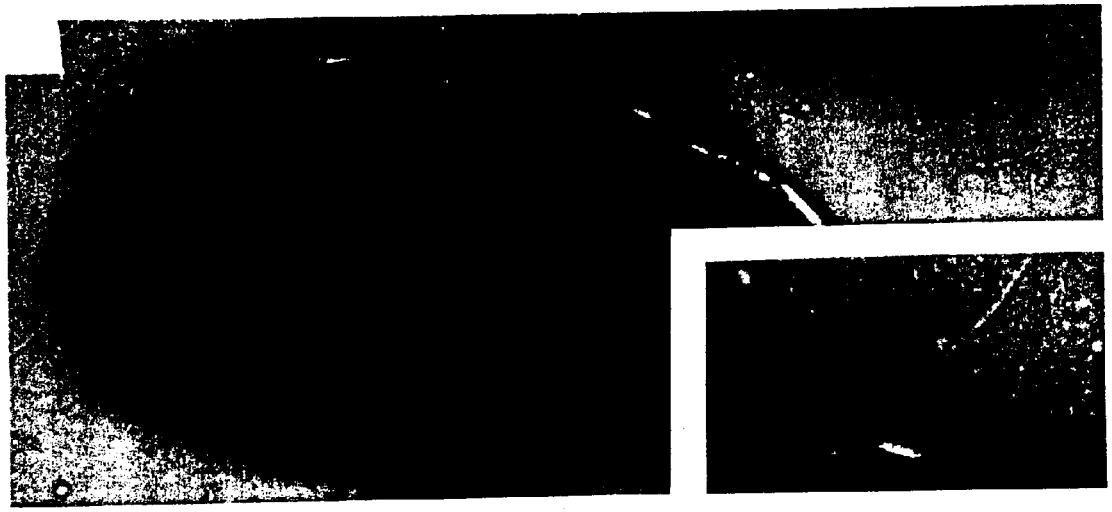
Figures 1, 2, 9B:
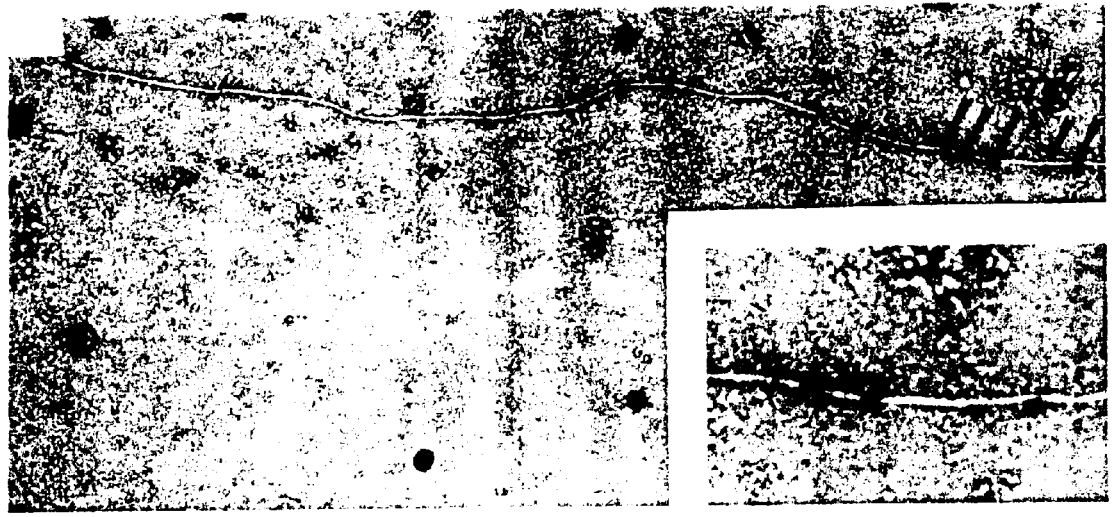

FIG. 8 illustrates a schematic diagram of the composition of pCBAK8-2b phagemid vector, the pathway for Fab assembly and incorporation in phage coat. The vector carries the chloramphenicol acetyl transferase (CAT) marker gene in addition to the nucleotide residue sequences encoding the Fd-cpVIII fusion polypeptide and the kappa chain. The f1 phage origin of replication facilitates the generation of single stranded phagemid. The isopropyl thiogalactopyranoside (IPTG) induced expression of a dicistronic message encoding the Fd-cpVIII fusion ($V_H$, $C_{H1}$, cpVIII) and the light chain ($V_L$, $C_L$) leads to the formation of heavy and light chains. Each chain is delivered to the periplasmic space by the pelB target sequence, which is subsequently cleaved. The heavy chain is anchored in the membrane by cpVIII fusion while the light chain is secreted into the periplasm. The heavy chain in the presence of light chain assembles to form Fab molecules. The Fabs are incorporated into phage particles via cpVIII (black dots).

FIGS. 9A-1, 9A-2, 9B-1 and 9B-2 illustrates the electron micrographic localization of 5–7 nm colloidal gold particles coated with NPN-BSA conjugate along the surface of filamentous phage, and from phage emerging from a bacterial cell. Panel 9A shows filamentous phage emerging from the surface of the bacterial cell specifically labelled with the colloidal gold particles coated with BSA-NPN antigen. Panel 9B shows a portion of a mature filamentous phage on the length of which is exhibited the labelling of antigen binding sites.

Figure 10:
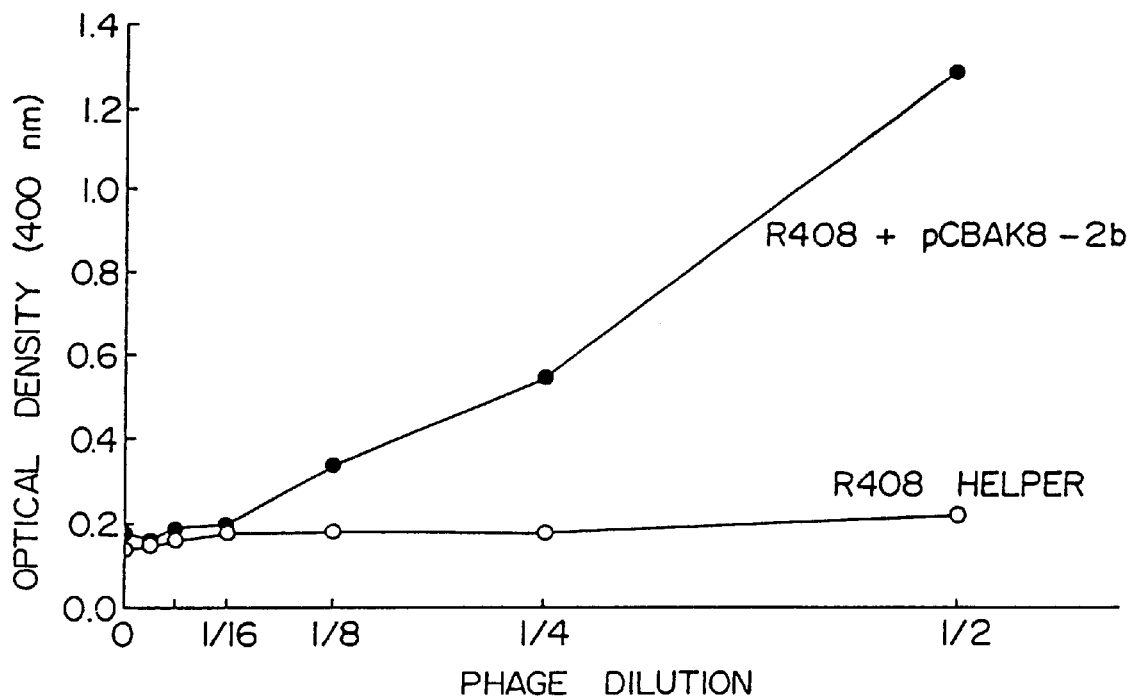

FIG. 10 illustrates the results of a two-site ELISA for assaying for the presence and function of Fab antibody attached to the surface of bacteriophage particles as described in Example 4b. For expression of Fab antibody on phage surfaces, XL1-Blue cells were transformed with the phagemid expression vector, pCBAK8-2b. The inducer, isopropyl thiogalactopyranoside (IPTG), was admixed with the bacterial suspension at a final concentration of 1 mM for one hour. Helper phage was then admixed with the bacterial suspension to initiate the generation of copies of the sense strand of the phagemid DNA. After a two hour maintenance period, bacterial supernatants containing bacteriophage particles were collected for assaying in ELISA.

Specific titratable binding of NPN-Fab-expressing bacteriophage particles to NPN-coated plates was exhibited. No binding was detected with helper phage alone.

Figure 11:
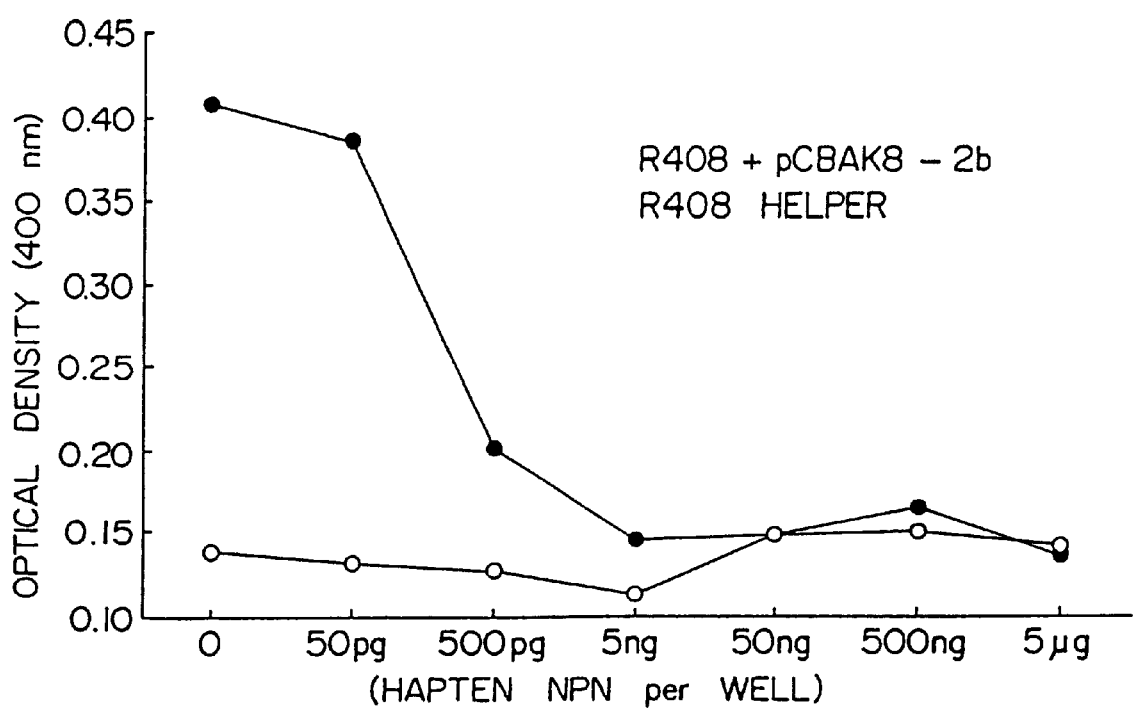

FIG. 11 illustrates the inhibition of NPN-Fab expressing bacteriophage to NPN antigen-coated plates with the addition of increasing amounts of free hapten. The assays were performed as described in FIG. 10. Complete inhibition of binding was observed with 5 ng of added free NPN hapten.

Figure 12:
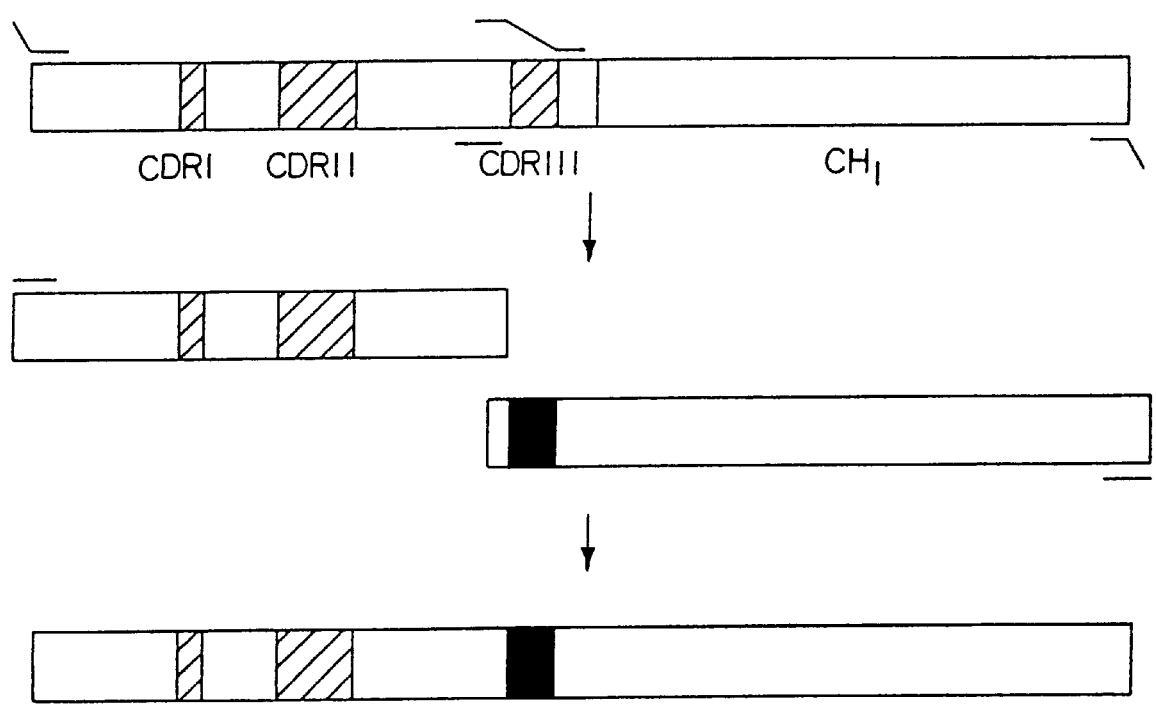

FIG. 12 illustrates schematically the process of mutagenizing the CDR3 region of a heavy chain fragment resulting in an alteration of binding specificity. The oligonucleotide primers are indicated by black bars. The process is described in Example 6.

FIG. 13 illustrates the amino acid sequences and corresponding SEQ ID NO of the heavy chain of the CDR3 region of the starting and selected clones, and the affinities of the clones for free fluorescein and Fl-BSA. The asterisk indicates the approximate Kd as determined by competitive ELISA.

FIG. 14 illustrates the amino acid sequences and corresponding SEQ ID NO of the light chain of the CDR3 region of the starting and selected clones, and the affinities of the clones for free fluorescein and Fl-BSA. The asterisk indicates the approximate Kd as determined by competitive ELISA.

DETAILED DESCRIPTION OF THE INVENTION

A. Definitions

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in J. Biol. Chem., 243:3552–59 (1969) and adopted at 37 C.F.R. 1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrasine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b) (4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5' -terminus to 3' -terminus.

Base Pair (bp): A partnership of adenine (A) with thymine (T), or of cytosine (C) with guanine (G) in a double stranded DNA molecule. In RNA, uracil (U) is substituted for thymine.

Nucleic Acid: A polymer of nucleotides, either single or double stranded.

Polynucleotide: a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Gene: A nucleic acid whose nucleotide sequence codes for an RNA or polypeptide. A gene can be either RNA or DNA.

Duplex DNA: a double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Complementary Bases: Nucleotides that normally pair up when DNA or RNA adopts a double stranded configuration.

Complementary Nucleotide Sequence: A sequence of his nucleotides in a single-stranded molecule of DNA or RNA that is sufficiently complementary to that on another single strand to specifically hybridize to it with consequent hydrogen bonding.

Conserved: A nucleotide sequence is conserved with respect to a preselected (reference) sequence if it nonrandomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that can be competitively inhibited.

Nucleotide Analoq: A purine or pyrimidine nucleotide that differs structurally from A, T, G, C, or U, but is sufficiently similar to substitute for the normal nucleotide in a nucleic acid molecule.

DNA Homolog: Is a nucleic acid having a preselected conserved nucleotide sequence and a sequence coding for a receptor capable of binding a preselected ligand.

Recombinant DNA (rDNA) molecule: a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) from mRNAs too produced using reverse transcriptase.

Receptor: A receptor is a molecule, such as a protein, glycoprotein and the like, that can specifically (nonrandomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Fusion Polypeptide: A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Cistron: Sequence of nucleotides in a DNA molecule coding for an amino acid residue sequence and including upstream and downstream DNA expression control elements.

Stop Codon: Any of three codons that do not code for an amino acid, but instead cause termination of protein synthesis. They are UAG, UAA and UGA and are also referred to as a nonsense or termination codon.

Leader Polypeptide: A short length of amino acid sequence at the amino end of a polypeptide, which carries or directs the polypeptide through the inner membrane and so ensures its eventual secretion into the periplasmic space and perhaps beyond. The leader is sequence peptide is commonly removed before the polypeptide becomes active.

Reading Frame: Particular sequence of contiguous nucleotide triplets (codons) employed in translation. The reading frame depends on the location of the translation initiation codon.

B. Filamentous Phage

The present invention contemplates a filamentous phage comprising a matrix of proteins encapsulating a genome encoding first and second polypeptides capable of forming a heterodimeric receptor. The phage further contains a heterodimeric receptor comprised of the first and second polypeptides surface-integrated into the matrix via a filamentous phage membrane anchor domain fused to at least one of the first or second polypeptides. The heterodimeric receptor has the capacity to bind ligand and therefor is referred to as a ligand-binding heterodimeric receptor.

The heterodimeric receptor in a preferred embodiment is an epitope-binding complex. That is, a complex of first and second polypeptides capable of binding an epitope. Preferably, the first and second polypeptides are antibody heavy chain and light chain polypeptides.

The first and second polypeptides are capable of autogenous assembly into a functional epitope-binding complex (heterodimeric receptor), which is then expressed on the outer surface of the phage in a manner accessible to ligand, i.e., they are surface-integrated into the phage. Thus, an epitope-binding complex is typically present on the surface of a phage of this invention. Typically, the epitope-binding complex is comprised of a linking polypeptide that contains a filamentous phage membrane anchor domain, such as a polypeptide described in Section C, and a non-linking polypeptide(s). Preferred are phage having a cpIII or cpVIII membrane anchor domain fused to a polypeptide of the heterodimeric complex as described further herein.

Because the receptor is linked to the phage in a surface accessible manner, the phage can be advantageously used as a solid-phase affinity sorbent. In preferred embodiments, the phage are linked, preferably removably linked, to a solid (aqueous insoluble) matrix such as agarose, cellulose, synthetic reins, polysaccharides and the like. For example, transformants shedding the phage can be applied to and retained in a column and maintained under conditions that support shedding of the phage. An aqueous composition containing a ligand that binds to the receptor expressed by the phage is then passed through the column at a predetermined rate and under receptor-binding conditions to form a solid-phase receptor-ligand complex. The column is then washed to remove unbound material, leaving the ligand bound to the solid-phase phage. The ligand can then be removed and recovered by washing the column with a buffer that promotes dissociation of the receptor-ligand complex.

Alternatively, purified phage can be admixed with a aqueous solution containing the ligand to be affinity purified. The receptor/ligand binding reaction admixture thus formed is maintained for a time period and under binding conditions sufficient for a phage-linked receptor-ligand complex to form. The phage-bound ligand (ligand-bearing phage) are then separated and recovered from the unbound materials, such as by centrifugation, electrophoresis, precipitation, and the like.

Phage of this invention can be labeled when used in a diagnostic method of this invention. Preferred labels include radioactively labeled nucleic acids incorporated into the phage genome, or radioactively labeled amino acids incorporated into protein components of the phage particle. Preparation of labeled phage can be routinely prepared by growing phage as described herein, but including radiolabeled nucleotides or radiolabeled amino acids in the culture medium for incorporation into nucleic acids or polypeptides of the phage, respectively. Exemplary labels are $^3$H-thymidine or $^{35}$S-methionine. Other isotopic labels and other nucleotide or amino acid precursors are readily available to one skilled in the art. The labeled phage preferably contains sufficient label to be detectable in a ligand binding assay of this invention, i.e., the phage is detectably labeled.

C. DNA Expression Vectors

A vector of the present invention is a recombinant DNA (rDNA) molecule adapted for receiving and expressing translatable DNA sequences in the form of a fusion polypeptide containing a filamentous phage membrane anchor domain and a prokaryotic secretion signal domain. The vector comprises a cassette that includes upstream and downstream translatable DNA sequences operatively linked via a sequence of nucleotides adapted for directional ligation to an insert DNA. The upstream translatable sequence encodes the secretion signal as defined herein. The downstream translatable sequence encodes the filamentous phage membrane anchor as defined herein. The cassette preferably includes DNA expression control sequences for expressing the fusion polypeptide that is produced when an insert is translatable. DNA sequence (insert DNA) is directionally inserted into the cassette via the sequence of nucleotides adapted for directional ligation. The filamentous phage membrane anchor is preferably a domain of the cpIII or cpVIII coat protein capable of binding the matrix of a filamentous phage particle, thereby incorporating the fusion polypeptide onto the phage surface.

An expression vector is characterized as being capable of expressing, in a compatible host, a structural gene product such as a fusion polypeptide of the present invention.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked.

As used herein with regard to DNA sequences or segments, the phrase "operatively linked" means the sequences or segments have been covalently joined, preferably by conventional phosphodiester bonds, into one strand of DNA, whether in single or double stranded form.

The choice of vector to which a cassette of this invention is operatively linked depends directly, as is well known in the art, on the functional properties desired, e.g., vector replication and protein expression, and the host cell to be transformed, these being limitations inherent in the art of constructing recombinant DNA molecules.

In preferred embodiments, the vector utilized includes a prokaryotic replicon i.e., a DNA sequence having the ability to direct autonomous replication and maintenance of the recombinant DNA molecule extra chromosomally in a prokaryotic host cell, such as a bacterial host cell, transformed therewith. Such replicons are well known in the art. In addition, those embodiments that include a prokaryotic replicon also include a gene whose expression confers a selective advantage, such as drug resistance, to a bacterial host transformed therewith. Typical bacterial drug resistance genes are those that confer resistance to ampicillin or tetracycline. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

A sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

A translatable DNA sequence is a linear series of nucleotides that provide an uninterrupted series of at least 8 codons that encode a polypeptide in one reading frame.

An upstream translatable DNA sequence encodes a prokaryotic secretion signal. The secretion signal is a leader peptide domain of protein that targets the protein to the periplasmic membrane of gram negative bacteria.

A preferred secretion signal is a pelB secretion signal. The predicted amino acid residue sequences of the secretion signal domain from two pelB gene product variants from *Erwinia carotova* are shown in Table 1 as described by Lei, et al., *Nature*, 331:543–546 (1988).

A particularly preferred pelB secretion signal is also shown in Table 1.

The leader sequence of the pelB protein has previously been used as a secretion signal for fusion proteins. Better et al., *Science*, 240:1041–1043 (1988); Sastry et al., *Proc. Natl. Acad. Sci. USA*, 86:5728–5732 (1989); and Mullinax et al., *Proc. Natl. Acad. Sci. USA*, 87:8095–8099 (1990).

Amino acid residue sequences for other secretion signal polypeptide domains from *E. coli* useful in this invention are also listed in Table 1. Oliver, In Neidhard, F. C. (ed.), *Escherichia coli* and *Salmonella Typhimurium*, American Society for Microbiology, Washington, D.C., 1:56–69 (1987).

A translatable DNA sequence encoding the pelB secretion signal having the amino acid residue sequence shown in SEQ. ID. NO. 5 is a preferred DNA sequence for inclusion in a DNA expression vector of this invention.

A downstream translatable DNA sequence encodes a filamentous phage membrane anchor. Preferred membrane anchors are obtainable from filamentous phage M13, f1, fd, and the like equivalent filamentous phage. Preferred membrane anchor domains are found in the coat proteins encoded by gene III and gene VIII. Thus, a downstream translatable DNA sequence encodes an amino acid residue sequence that corresponds, and preferably is identical, to the membrane anchor domain of either a filamentous phage gene III or gene VIII coat polypeptide.

The membrane anchor domain of a filamentous phage coat protein is a portion of the carboxy terminal region of the coat protein and includes a region of hydrophobic amino acid residues for spanning a lipid bilayer membrane, and a region of charged amino acid

TABLE 1

Leader Sequences

| SEQ ID NO | Type | Amino Acid Residue Sequence |
|---|---|---|
| (5) | PelB[1] | MetLysTyrLeuLeuProThrAlaAlaAlaGlyLeuLeu LeuLeuAlaAlaGlnProAlaMet |
| (6) | pelB[2] | MetLysTyrLeuLeuProThrAlaAlaAlaGlyLeuLeu LeuLeuAlaAlaGlnProAlaGlnProAlaMetAla |
| (7) | pelB[3] | MetLysSerLeuIleThrProIleAlaAlaGlyLeuLeu LeuAlaPheSerGlnTyrSerLeuAla |
| (8) | MalE[4] | MetLysIleLysThrGlyAlaArgIleLeuAlaLeuSer AlaLeuThrThrMetMetPheSerAlaSerAlaLeuAla LysIle |
| (9) | OmpF[4] | MetMetLysArgAsnIleLeuAlaValIleValProAla LeuLeuValAlaGlyThrAlaAsnAlaGlu |
| (10) | PhoA[4] | MetLysGlnSerThrIleAlaLeuAlaLeuLeuProLeu LeuPheThrProValThrLysAlaArgThr |
| (11) | Bla[4] | MetSerIleGlnHisPheArgValAlaLeuIleProPhe PheAlaAlaPheCysLeuProValPheAlaHisPro |
| (12) | LamB[4] | MetMetIleThrLeuArgLysLeuProLeuAlaValAla ValAlaAlaGlyValMetSerAlaGlnAlaMetAlaVal Asp |
| (13) | Lpp[4] | MetLysAlaThrLysLeuValLeuGlyAlaValIleLeu GlySerThrLeuLeuAlaGlyCysSer |
| (14) | cpVIII[5] | MetLysLysSerLeuValLeuLysAlaSerValAlaVal AlaThrLeuValProMetLeuSerPheAla |
| (15) | cpIII[6] | MetLysLysLeuLeuPheAlaIleProLeuValValPro PheTyrSerHisSer |

[1]pelB used in this invention
[2]pelB from *Erwinia carotovora* gene
[3]pelB from *Erwinia carotovora* EC 16 gene
[4]leader sequences from *E. coli*
[5]leader sequence for cpVIII
[6]leader sequence for cpIII residues normally found at the cytoplasmic face of the membrane and extending away from the membrane.

In the phage f1, gene VIII coat protein's membrane spanning region comprises residue Trp-26 through Lys-40, and the cytoplasmic region comprises the carboxy-terminal 11 residues from 41 to 52. Ohkawa et al., *J. Biol. Chem.*, 256:9951–9958 (1981). An exemplary membrane anchor would consist of residues 26 to 40 of cpVIII.

Thus, the amino acid residue sequence of a preferred membrane anchor domain is derived from the M13 filamentous phage gene III coat protein (also designated cpIII). A preferred cpIII-derived membrane anchor has a sequence shown in SEQ ID NO. 16 from residue 1 to residue 211. Gene III coat protein is present on a mature filamentous phage at one end of the phage particle with typically about 4 to 6 copies of the coat protein.

The amino acid residue sequence of another preferred membrane anchor domain is derived from the M13 filamentous phage gene VIII coat protein (also designated cpVIII). A preferred cpVIII-derived membrane anchor has a sequence shown in SEQ ID NO. 17 from residue 1 to residue 50. Gene VIII coat protein is present on a mature filamentous phage over the majority of the phage particle with typically about 2500 to 3000 copies of the coat protein.

For detailed descriptions of the structure of filamentous phage particles, their coat proteins and particle assembly, see the reviews by Rached et al., *Microbiol. Rev.*, 50:401–427 (1986); and Model et al., in "The Bacteriophages: Vol. 2", R. Calendar, ed. Plenum Publishing co., pp. 375–456, (1988).

A cassette in a DNA expression vector of this invention is the region of the vector that forms, upon insertion of a translatable DNA sequence (insert DNA), a sequence of nucleotides capable of expressing, in an appropriate host, a fusion polypeptide of this invention. The expression-competent sequence of nucleotides is referred to as a cistron. Thus, the cassette comprises DNA expression control elements operatively linked to the upstream and downstream translatable DNA sequences. A cistron is formed when a translatable DNA sequence is directionally inserted (directionally ligated) between the upstream and downstream sequences via the sequence of nucleotides adapted for that purpose. The resulting three translatable DNA sequences, namely the upstream, the inserted and the downstream sequences, are all operatively linked in the same reading frame.

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3–9 nucleotides long located 3–11 nucleotides upstream from the initiation codon [Shine et al., *Nature*, 254:34 (1975)]. The sequence, AGGAGGU, which is called the Shine-Dalgarno (SD) sequence, is complementary to the 3' end of *E. coli* 16S mRNA. Binding of the ribosome to mRNA and the sequence at the 3' end of the mRNA can be affected by several factors:

(i) The degree of complementarity between the SD sequence and 3' end of the 16S tRNA.

(ii) The spacing and possibly the DNA sequence lying between the SD sequence and the AUG [Roberts et al., *Proc. Natl. Acad. Sci. USA*, 76:760 (1979a); Roberts et al., *Proc. Natl. Acad. Sci. USA*, 76:5596 (1979b); Guarente et al., *Science*, 209:1428 (1980); and Guarente et al., *Cell*, 20:543 (1980).] Optimization is achieved by measuring the level of expression of genes in plasmids in which this spacing is systematically altered. Comparison of different mRNAs shows that there are statistically preferred sequences from positions −20 to +13 (where the A of the AUG is position 0) [Gold et al., *Annu. Rev. Microbiol.*, 35:365 (1981)]. Leader sequences have been shown to influence translation dramatically (Roberts et al., 1979 a, b supra).

(iii) The nucleotide sequence following the AUG, which affects ribosome binding [Taniguchi et al., *J. Mol. Biol.*, 118:533 (1978)].

Useful ribosome binding sites are shown in Table 2 below.

TABLE 2

Ribosome Binding Sites*

| | SEQ. ID. NO. | |
|---|---|---|
| 1. | (18) | 5' AAUCUU<u>GGAGG</u>CUUUUUU<u>AUG</u>GUUCGUUCU |
| 2. | (19) | 5' UAAC<u>UAAGG</u>AUGAAAUGC<u>AUG</u>UCUAAGACA |
| 3. | (20) | 5' UCCU<u>AGGAGG</u>UUUGACCU<u>AUG</u>CGAGCUUUU |
| 4. | (21) | 5' AUGUAC<u>UAAGGAGG</u>UUGU<u>AUG</u>GAACAACGC |

*Sequences of initiation regions for protein synthesis in four phage mRNA molecules are underlined.
AUG = initiation codon (double underlined)
1. = Phage φX174 gene-A protein
2. = Phage Qβ replicase
3. = Phage R17 gene-A protein
4. = Phage lambda gene-cro protein The 3' control sequences define at least one termination (stop) codon in frame with and operatively linked to the downstream translatable DNA sequence.

Thus, a DNA expression vector of this invention provides a system for cloning translatable DNA sequences into the cassette portion of the vector to produce a cistron capable of expressing a fusion polypeptide of this invention.

In preferred embodiments, a DNA expression vector provides a system for independently cloning (inserting) two translatable DNA sequences into two separate cassettes present in the vector, to form two separate cistrons for expressing both polypeptides of a heterodimeric receptor, or the ligand binding portions of the polypeptides that comprise a heterodimeric receptor. The DNA expression vector for expressing two cistrons is referred to as a dicistronic expression vector.

Thus, a preferred DNA expression vector of this invention comprises, in addition to the cassette previously described in detail, a second cassette for expressing a second fusion polypeptide. The second cassette includes a second translatable DNA sequence that encodes a secretion signal, as defined herein before, operatively linked at its 3' terminus via a sequence of nucleotides adapted for directional ligation to a downstream DNA sequence of the vector that typically defines at least one stop codon in the reading frame of the cassette. The second translatable DNA sequence is operatively linked at its 5' terminus to DNA expression control sequences forming the 5' elements defined above. The second cassette is capable, upon insertion of a translatable DNA sequence (insert DNA), of expressing the second fusion polypeptide comprising a fusion of the secretion signal with a polypeptide coded by the insert DNA.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication. See, for example, Rasched et al., *Microbiol. Rev.*, 50:401–427 (1986); and Horiuchi, *J. Mol. Biol.*, 188:215–223 (1986).

A preferred filamentous phage origin of replication for use in the present invention is a M13, f1 or fd phage origin of replication. Particularly preferred is a filamentous phage origin of replication having a sequence shown in SEQ ID NO. 117 and described by Short et al., *Nucl. Acids Res.*, 16:7583–7600 (1988). Preferred DNA expression vectors are the dicistronic expression vectors pCOMB8, pCKAB8, pCOM2-8, pCOMB3, pCKAB3, pCOMB2-3 and pCOMB2-3' described in Example 1.

Insofar as a vector of this invention may be manipulated to contain an insert DNA, thereby having the capacity to express a fusion polypeptide, one embodiment contemplates the previously described vectors containing an insert DNA. Particularly preferred vectors containing antibody genes are described in the Examples.

D. Polypeptides

In another embodiment, the present invention contemplates a polypeptide comprising an insert domain flanked by an amino-terminal secretion signal domain and a carboxy-terminal filamentous phage coat protein membrane anchor domain.

The polypeptide is a fusion polypeptide having a receptor domain comprised of an amino acid residue sequence that defines the ligand (epitope) binding domain of a receptor protein positioned between a prokaryotic secretion signal domain and a filamentous phage membrane anchor domain. That is, the insert domain in the fusion polypeptide is the ligand-binding domain of a receptor and is also referred to as a ligand-binding receptor polypeptide.

Insofar as the polypeptide has a receptor domain, it is also referred to herein as a receptor. In other preferred embodiments the secretion signal domain is a pelB secretion signal as described herein. In addition, it is preferred that the membrane anchor domain be derived from the filamentous phage cpIII or cpVIII proteins as described herein.

In preferred embodiments, the receptor protein is a polypeptide chain of a ligand-binding heterodimeric receptor. More preferably the heterodimeric receptor is an epitope-binding complex.

Preferred heterodimeric receptors include immunoglobulins, major histocompatibility antigens of class I or II, lymphocyte receptors, integrins and the like heterodimeric receptors. Immunoglobulins (antibody-molecules) can be in the form of Fab or Fv fragments, or other portions of an antibody molecule that contain regions of the variable domain of the heavy and light chains.

In one embodiment, a polypeptide of this invention has an amino acid residue sequence that can be represented by the formula, shown in the direction of amino- to carboxy terminus:

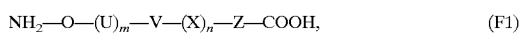

$$NH_2—O—(U)_m—V—(X)_n—Z—COOH, \quad (F1)$$

where O represents an amino acid residue sequence defining a secretion signal, U represents a first spacer polypeptide, V represents an amino acid residue sequence defining a receptor domain (a ligand-binding receptor polypeptide), X represents a second spacer polypeptide, and Z represents an amino acid residue sequence defining a filamentous phage coat protein membrane anchor, with the proviso that m is the integer 0 or 1 such that when m is O, U is not present, and when m is 1, U is present, and n is 0 or 1 such that when n is O, X is not present and when n is 1, X is present.

In the formula (F1), the secretion signal and the filamentous phage coat protein membrane anchor are as defined herein above. Thus, a preferred polypeptide comprises an antibody variable chain domain-derived polypeptide operatively linked at its amino-terminus to the secretion signal and operatively linked at its carboxy-terminus to the membrane anchor.

A preferred polypeptide of this embodiment consists essentially of an antibody heavy chain polypeptide as the variable domain. In this regard "consists essentially of" means that the polypeptide does not contain an antibody light chain polypeptide, or portion thereof. Particularly preferred is a polypeptide according to formula (F1) where Z defines the cpIII or cpVIII membrane anchor as described herein. In another preferred embodiment the secretion signal is the pelB secretion signal.

As used herein with regard to polypeptides, the phrase "operatively linked" means that polypeptide fragments, or protein domains represented by polypeptides, have been covalently joined into a single polypeptide polymer, preferably by conventional amide bonds between the adjacent amino acids being linked in the polypeptide.

In one embodiment, V is an amino acid residue sequence that defines the ligand binding domain of a chain of a heterodimeric receptor molecule, and preferably is an immunoglobulin variable region polypeptide. In a particularly preferred polypeptide V is a $V_H$ or $V_L$ polypeptide. Most preferred is a polypeptide where V is an immunoglobulin $V_H$ polypeptide (antibody heavy chain polypeptide), and m and n are both zero.

In another embodiment, U or X can define a proteolytic cleavage site, such as the sequence of amino acids found in a precursor protein, such as prothrombin, factor X and the like, that defines the site of cleavage of the polypeptide. A fusion polypeptide having a cleavage site provides a means to purify the polypeptide away from the phage particle to which it is attached.

The polypeptide spacers U and X can each have any sequence of amino acid residues of from about 1 to 6 amino acid residues in length. Typically the spacer residues are present in a polypeptide to accommodate the continuous reading frame that is required when a polypeptide is produced by the methods disclosed herein using a DNA expression vector of this invention.

A receptor of the present invention assumes a conformation having a binding site specific for, as evidenced by its ability to be competitively inhibited, a preselected or predetermined ligand such as an antigen, hapten, enzymatic substrate and the like. In one embodiment, a receptor of this invention is a ligand binding polypeptide that forms an antigen binding site which specifically binds to a preselected antigen to form a complex having a sufficiently strong binding between the antigen and the binding site for the complex to be isolated. When the receptor is an antigen binding polypeptide its affinity or avidity is generally greater than $10^5$ $M^{-1}$ more usually greater than $10^6$ and preferably greater than $10^8$ $M^{-1}$.

In another embodiment, a receptor of the subject invention binds a substrate and catalyzes the formation of a product from the substrate. While the topology of the ligand binding site of a catalytic receptor is probably more important for its preselected activity than its affinity (association constant or pKa) for the substrate, the subject catalytic receptors have an association constant for the preselected substrate generally greater than $10^3$ $M^{-1}$, more usually greater than $10^5$ $M^{-1}$ or $10^6$ $M^{-1}$ and preferably greater than $10^7$ $M^{-1}$.

Preferably the receptor produced by the subject invention is heterodimeric and is therefore normally comprised of two different polypeptide chains, which together assume a conformation having a binding affinity, or association constant for the preselected ligand that is different, preferably higher, than the affinity or association constant of either of the polypeptides alone, i.e., as monomers. The heterodimeric receptor is referred to as a ligand-binding heterodimeric receptor to connote its ability to bind ligand.

Thus, a preferred embodiment contemplates a ligand-binding heterodimeric receptor comprising first and second polypeptides. The first polypeptide is flanked by an amino-terminal prokaryotic secretion signal domain and a carboxy-terminal filamentous phage membrane anchor domain. The second polypeptide is fused to an amino-terminal prokaryotic secretion signal domain. A particularly preferred ligand-binding heterodimeric receptor utilizes a prokaryotic secretion signal as described herein. Additionally, a preferred ligand-binding heterodimeric receptor contains a membrane anchor-derived from cpIII or cpVIII as described herein.

A ligand-binding heterodimeric receptor is referred to as an epitope-binding complex to connote that the complex has a capacity to bind an epitope present on a ligand, and to connote that the heterodimeric receptor is formed by the association (complexation) of two polypeptides as described herein.

One or both of the different polypeptide chains is preferably derived from the variable region of the light and heavy chains of an immunoglobulin. Typically, polypeptides comprising the light ($V_L$) and heavy ($V_H$) variable regions are employed together for binding the preselected ligand.

Thus, one embodiment contemplates a ligand-binding heterodimeric receptor in which the first polypeptide is an antibody heavy chain polypeptide and the second polypeptide is a light chain polypeptide. An alternative embodiment contemplates a ligand-binding heterodimeric receptor in which the first polypeptide is an antibody light chain polypeptide and the second is an antibody heavy chain polypeptide.

A receptor produced by the subject invention can be active in monomeric as well as multimeric forms, either homomeric or heteromeric, preferably heterodimeric. For example, $V_H$ and $V_L$ ligand binding polypeptide produced by the present invention can be advantageously combined in the heterodimer to modulate the activity of either or to produce an activity unique to the heterodimer.

Where the individual ligand polypeptides are referred to as $V_H$ and $V_L$, the heterodimer can be referred to as a Fv. However, it should be understood that a $V_H$ may contain in addition to the $V_H$, substantially all or a portion of the heavy chain constant region. Similarly, a $V_L$ may contain, in addition to the $V_L$, substantially all or a portion of the light chain constant region. A heterodimer comprised of a $V_H$ containing a portion of the heavy chain constant region and a $V_L$ containing substantially all of the light chain constant region is termed a Fab fragment. The production of Fab can be advantageous in some situations because the additional constant region sequences contained in a Fab as compared to a Fv can stabilize the $V_H$ and $V_L$ interaction. Such stabilization can cause the Fab to have higher affinity for antigen. In addition the Fab is more commonly used in the art and thus there are more commercial antibodies available to specifically recognize a Fab in screening procedures.

The individual $V_H$ and $V_L$ polypeptides can be produced in lengths equal to or substantially equal to their naturally occurring lengths. However, in preferred embodiments, the $V_H$ and $V_L$ polypeptides will generally have fewer than 125 amino acid residues, more usually fewer than about 120 amino acid residues, while normally having greater than 60 amino acid residues, usually greater than about 95 amino acid residues, more usually greater than about 100 amino acid residues. Preferably, the $V_H$ will be from about 110 to about 230 amino acid residues in length while $V_L$ will be from about 95 to about 214 amino acid residues in length. $V_H$ and $V_L$ chains sufficiently long to form Fabs are preferred.

The amino acid residue sequences will vary widely, depending upon the particular idiotype involved. Usually, there will be at least two cysteines separated by from about 60 to 75 amino acid residues and joined by a disulfide bond. The polypeptides produced by the subject invention will normally be substantial copies of idiotypes of the variable regions of the heavy and/or light chains of immunoglobulins, but in some situations a polypeptide may contain random mutations in amino acid residue sequences in order to advantageously improve the desired activity.

In some situations, it is desirable to provide for covalent cross linking of the $V_H$ and $V_L$ polypeptides, which can be accomplished by providing cysteine resides at the carboxyl termini. The polypeptide will normally be prepared free of the immunoglobulin constant regions, however a small portion of the J region may be included as a result of the advantageous selection of DNA synthesis primers. The D region will normally be included in the transcript of the $V_H$.

Typically the C terminus region of the $V_H$ and $V_L$ polypeptides will have a greater variety of sequences than the N terminus and, based on the present strategy, can be further modified to permit a variation of the normally occurring $V_H$ and $V_L$ chains. A synthetic polynucleotide can be employed to vary one or more amino acid in a hypervariable region.

E. Methods for Producing a Library
1. General Rationale

In one embodiment the present invention provides a system for the simultaneous cloning and screening of preselected ligand-binding specificities from gene repertoires using a single vector system. This system provides linkage of cloning and screening methodologies and has two requirements. First, that expression of the polypeptide chains of a heterodimeric receptor in an in vitro expression host such as *E. coli* requires coexpression of the two polypeptide chains in order that a functional heterodimeric receptor can assemble to produce a receptor that binds ligand. Second, that screening of isolated members of the library for a preselected ligand-binding capacity requires a means to correlate (a linkage) the binding capacity of an expressed receptor molecule with a convenient means to isolate the gene that encodes the member from the library.

Linkage of expression and screening is accomplished by the combination of targeting of a fusion polypeptide into the periplasm of a bacterial cell to allow assembly of a functional receptor, and the targeting of a fusion polypeptide onto the coat of a filamentous phage particle during phage assembly to allow for convenient screening of the library member of interest. Periplasmic targeting is provided by the presence of a secretion signal domain in a fusion polypeptide of this invention. Targeting to a phage particle is provided by the presence of a filamentous phage coat protein membrane anchor domain (i.e., a cpIII- or cpVIII-derived membrane anchor domain) in a fusion polypeptide of this invention.

The present invention describes in one embodiment a method for producing a library of DNA molecules, each DNA molecule comprising a cistron for expressing a fusion polypeptide on the surface of a filamentous phage particle. The method comprises the steps of (a) forming a ligation admixture by combining in a ligation buffer (i) a repertoire of polypeptide encoding genes and (ii) a plurality of DNA expression vectors in linear form adapted to form a fusion polypeptide expressing cistron, and (b) subjecting the admixture to ligation conditions for a time period sufficient for the repertoire of genes to become operatively linked (ligated) to the plurality of vectors to form the library.

In this embodiment, the repertoire of polypeptide encoding genes are in the form of double-stranded (ds) DNA and each member of the repertoire has cohesive termini adapted for directional ligation. In addition, the plurality of DNA expression vectors are each linear DNA molecules having upstream and downstream cohesive termini that are (a) adapted for directionally receiving the polypeptide genes in a common reading frame, and (b) operatively linked to respective upstream and downstream translatable DNA sequences. The upstream translatable DNA sequence encodes a secretion signal, preferably a pelb secretion signal, and the downstream translatable DNA sequence encodes a filamentous phage coat protein membrane anchor as described herein for a polypeptide of this invention. The translatable DNA sequences are also operatively linked to respective upstream and downstream DNA expression control sequences as defined for a DNA expression vector described herein.

The library so produced can be utilized for expression and screening of the fusion polypeptides encoded by the resulting library of cistrons represented in the library by the expression and screening methods described herein.

2. Production of Gene Repertoires

A gene repertoire is a collection of different genes, preferably polypeptide-encoding genes (polypeptide genes), and may be isolated from natural sources or can be generated artificially. Preferred gene repertoires are comprised of conserved genes. Particularly preferred gene repertoires comprise either or both genes that code for the members of a dimeric receptor molecule.

A gene repertoire useful in practicing the present invention contains at least $10^3$, preferably at least $10^4$, more preferably at least $10^5$, and most preferably at least $10^7$ different genes. Methods for evaluating the diversity of a repertoire of genes is well known to one skilled in the art.

Thus, in one embodiment, the present invention contemplates a method of isolating a pair of genes coding for a dimeric receptor having a preselected activity from a repertoire of conserved genes. Additionally, expressing the cloned pair of genes and isolating the resulting expressed dimeric receptor protein is also described. Preferably, the receptor will be a heterodimeric polypeptide capable of binding ligand, such as an antibody molecule or immunologically active portion thereof, a cellular receptor, or a cellular adhesion protein coded for by one of the members of a family of conserved genes, i.e., genes containing a conserved nucleotide sequence of at least about 10 nucleotides in length.

Exemplary conserved gene families encoding different polypeptide chains of a dimeric receptor are those coding for immunoglobulins, major histocompatibility complex antigens of class I or II, lymphocyte receptors, integrins and the like.

A gene can be identified as belonging to a repertoire of conserved genes using several methods. For example, an isolated gene may be used as a hybridization probe under low stringency conditions to detect other members of the repertoire of conserved genes present in genomic DNA using the methods described by Southern, *J. Mol. Biol.*, 98:503 (1975). If the gene used as a hybridization probe hybridizes to multiple restriction endonuclease fragments of the genome, that gene is a member of a repertoire of conserved genes.

Immunoglobulins

Figure 1:
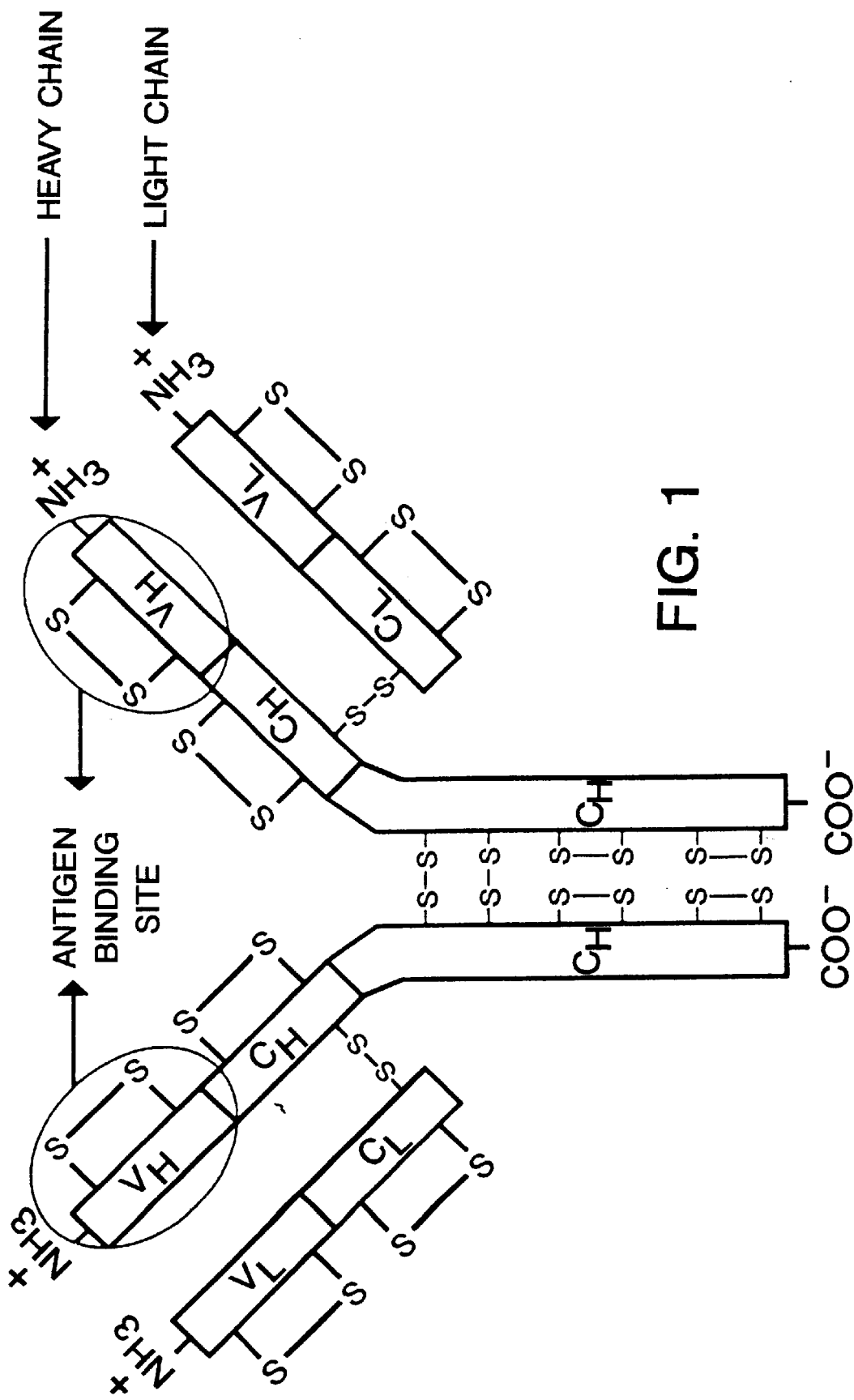
FIG. 1 illustrates a schematic diagram of the immunoglobulin molecule showing the principal structural features. The circled area on the heavy chain represents the variable region ($V_H$), a polypeptide containing a biologically active (ligand binding) portion of that region, and a gene coding for that polypeptide, are produced by the methods of the present invention.
Figure 2A:
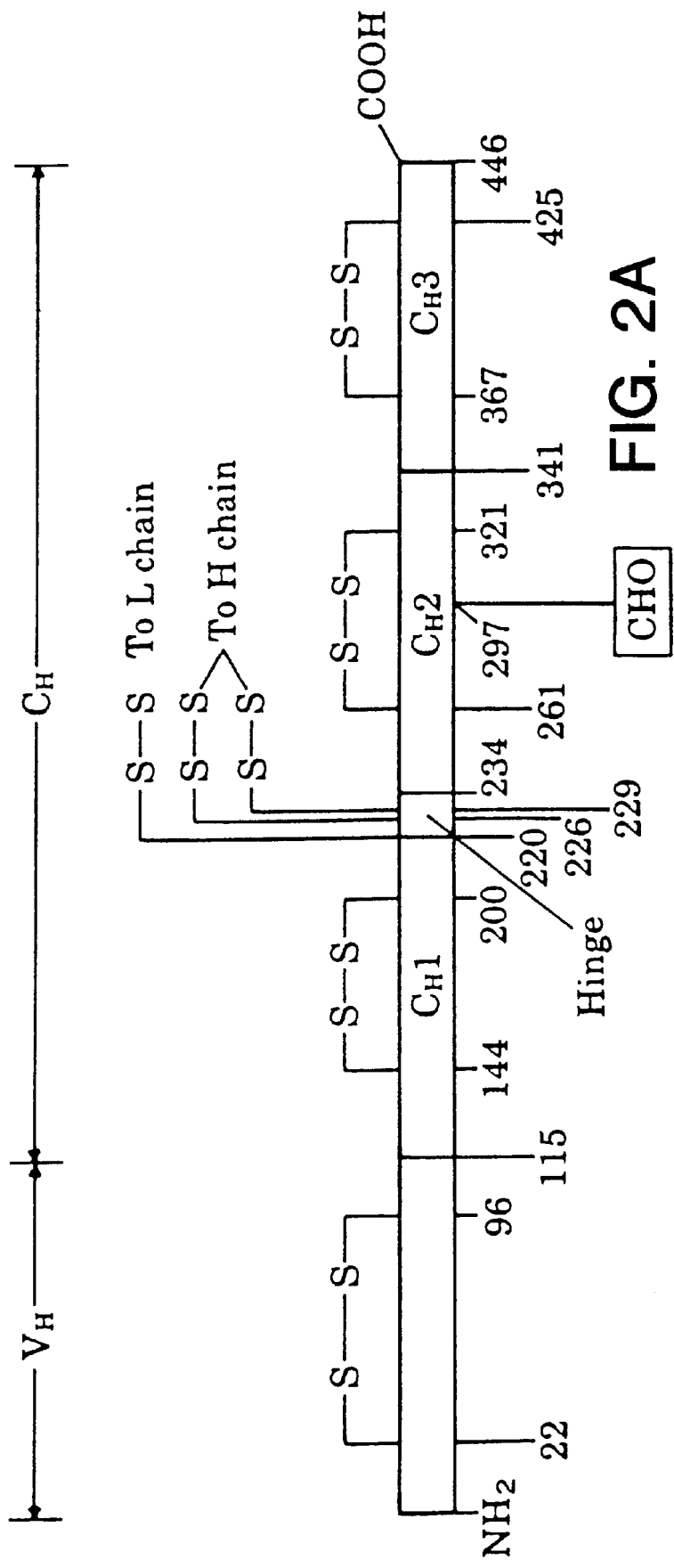
FIG. 2A is a diagrammatic sketch of a heavy (H) chain of human IgG (IgG1 subclass). Numbering is from the N-terminus on the left to the C-terminus on the right. Note the presence of four domains, each containing an intrachain disulfide bond (S—S) spanning approximately 60 amino acid residues. The symbol CHO stands for carbohydrate. The V region of the heavy (H) chain ($V_H$) resembles $V_L$ in having three hypervariable CDR (not shown).
Figures 1, 2B:
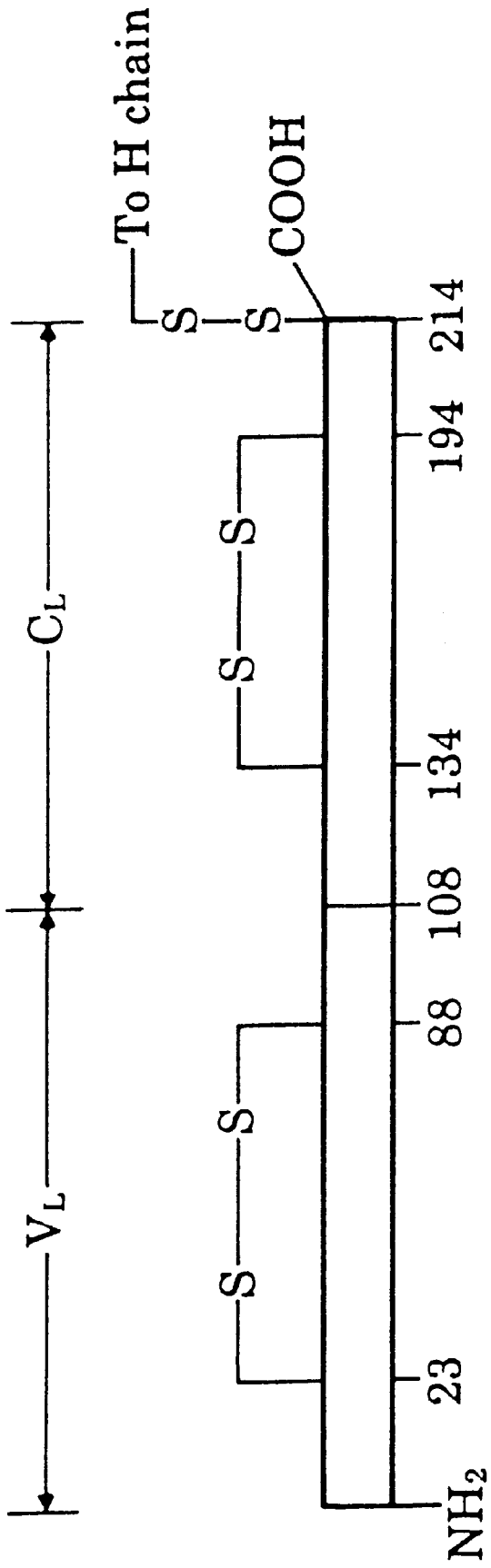
Figures 2, 2B:
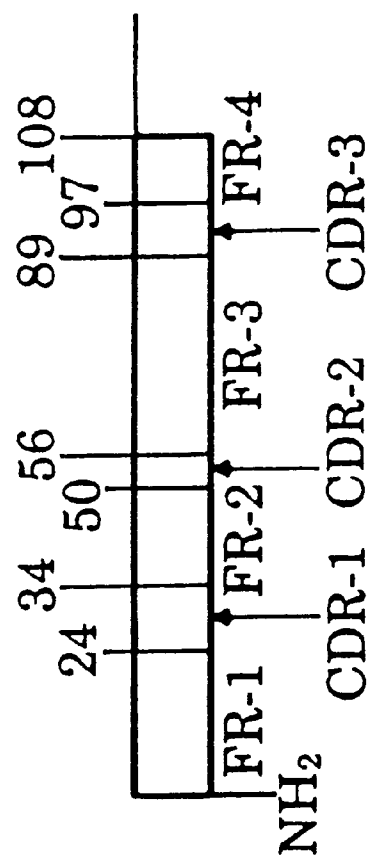

The immunoglobulins, or antibody molecules, are a large family of molecules that include several types of molecules, such as IgD, IgG, IgA, IgM and IgE. The antibody molecule is typically comprised of two heavy (H) and light (L) chains with both a variable (V) and constant (C) region present on each chain as shown in FIG. 1. Schematic diagrams of human IgG heavy chain and human kappa light chain are shown in FIGS. 2A and 2B, respectively. Several different regions of an immunoglobulin contain conserved sequences useful for isolating an immunoglobulin repertoire. Extensive amino acid and nucleic acid sequence data displaying exemplary conserved sequences is compiled for immunoglobulin molecules by Kabat et al., in *Sequences of Proteins of Immunological Interest*, National Institutes of Health, Bethesda, Md., 1987.

The C region of the H chain defines the particular immunoglobulin type. Therefore the selection of conserved sequences as defined herein from the C region of the H chain results in the preparation of a repertoire of immunoglobulin genes having members of the immunoglobulin type of the selected C region.

The V region of the H or L chain typically comprises four framework (FR) regions each containing relatively lower degrees of variability that includes lengths of conserved sequences. The use of conserved sequences from the FR1 and FR4 (J region) framework regions of the $V_H$ chain is a preferred exemplary embodiment and is described herein in the Examples. Framework regions are typically conserved across several or all immunoglobulin types and thus conserved sequences contained therein are particularly suited for preparing repertoires having several immunoglobulin types.

Major Histocompatibility Complex

The major histocompatibility complex (MHC) is a large genetic locus that encodes an extensive family of proteins that include several classes of molecules referred to as class I, class II or class III MHC molecules. Paul et al., in *Fundamental Immunology*, Raven Press, NY, pp. 303–378 (1984).

Class I MHC molecules are a polymorphic group of transplantation antigens representing a conserved family in which the antigen is comprised of a heavy chain and a non-MHC encoded light chain. The heavy chain includes several regions, termed the N, C1, C2, membrane and cytoplasmic regions. Conserved sequences useful in the present invention are found primarily in the N, C1 and C2 regions and are identified as continuous sequences of "invariant residues" in Kabat et al., supra.

Class II MHC molecules comprise a conserved family of polymorphic antigens that participate in immune responsiveness and are comprised of an alpha and a beta chain. The genes coding for the alpha and beta chain each include several regions that contain conserved sequences suitable for producing MHC class II alpha or beta chain repertoires. Exemplary conserved nucleotide sequences include those coding for amino acid residues 26–30 of the A1 region, residues 161–170 of the A2 region and residues 195–206 of the membrane region, all of the alpha chain. Conserved sequences are also present in the B1, B2 and membrane regions of the beta chain at nucleotide sequences coding for amino acid residues 41–45, 150–162 and 200–209, respectively.

Lymphocyte Receptors and Cell Surface Antigens

Lymphocytes contain several families of proteins on their cell surfaces including the T-cell receptor, Thy-1 antigen and numerous T-cell surface antigens including the antigens defined by the monoclonal antibodies OKT4 (leu3), OKT5/8 (leu2), OKT3, OKT1 (leu1), OKT 11 (leu5) OKT6 and OKT9. Paul, supra at pp. 458–479.

The T-cell receptor is a term used for a family of antigen binding molecules found on the surface of T-cells. The T-cell receptor as a family exhibits polymorphic binding specificity similar to immunoglobulins in its diversity. The mature T-cell receptor is comprised of alpha and beta chains each having a variable (V) and constant (C) region. The similarities that the T-cell receptor has to immunoglobulins in genetic organization and function shows that T-cell receptor contains regions of conserved sequence. Lai et al., *Nature*, 331:543–546 (1988).

Exemplary conserved sequences include those coding for amino acid residues 84–90 of alpha chain, amino acid residues 107–115 of beta chain, and amino acid residues 91–95 and 111–116 of the gamma chain. Kabat et al., supra, p. 279.

Integrins And Adhesions

Adhesive proteins involved in cell attachment are members of a large family of related proteins termed integrins. Integrins are heterodimers comprised of a beta and an alpha subunit. Members of the integrin family include the cell surface glycoproteins platelet receptor GpIIb-IIIa, vitronectin receptor (VnR), fibronectin receptor (FnR) and the leukocyte adhesion receptors LFA-1, Mac-1, Mo-1 and 60.3. Rouslahti et al., *Science*, 238:491–497 (1987). Nucleic acid and protein sequence data demonstrates regions of conserved sequences exist in the members of these families, particularly between the beta chain of GpIIb-IIIa, VnR and FnR, and between the alpha subunit of VnR, Mac-1, LFA-1, FnR and GpIIb-IIIa. Suzuki et al., *Proc. Natl. Acad. Sci. USA*, 83:8614–8618, 1986; Ginsberg et al., *J. Biol. Chem.*, 262:5437–5440, 1987.

Various well known methods can be employed to produce a useful gene repertoire. For instance, $V_H$ and $V_L$ gene repertoires can be produced by isolating $V_H$- and $V_L$-coding mRNA from a heterogeneous population of antibody producing cells, i.e., B lymphocytes (B cells), preferably rearranged B cells such as those found in the circulation or spleen of a vertebrate. Rearranged B cells are those in which immunoglobulin gene translocation, i.e., rearrangement, has occurred as evidenced by the presence in the cell of mRNA with the immunoglobulin gene V, D and J region transcripts adjacently located thereon. Typically, the B cells are collected in a 1–100 ml sample of blood which usually contains $10^6$ B cells/ml.

In some cases, it is desirable to bias a repertoire for a preselected activity, such as by using as a source of nucleic acid cells (source cells) from vertebrates in any one of various stages of age, health and immune response. For example, repeated immunization of a healthy animal prior to collecting rearranged B cells results in obtaining a repertoire enriched for genetic material producing a receptor of high affinity. Mullinax et al., *Proc. Natl. Acad. Sci. USA*, 87:8095–8099 (1990). Conversely, collecting rearranged B cells from a healthy animal whose immune system has not been recently challenged (i.e., a naive immune system) results in producing a repertoire that is not biased towards the production of high affinity $V_H$ and/or $V_L$ polypeptides.

It should be noted the greater the genetic heterogeneity of the population of cells for which the nucleic acids are obtained, the greater the diversity of the immunological repertoire (comprising $V_H$- and $V_L$-coding genes) that will be made available for screening according to the method of the present invention. Thus, cells from different individuals, particularly those having an immunologically significant age difference, and cells from individuals of different strains, races or species can be advantageously combined to increase the heterogeneity (diversity) of a repertoire.

Thus, in one preferred embodiment, the source cells are obtained from a vertebrate, preferably a mammal, which has been immunized or partially immunized with an antigenic ligand (antigen) against which activity is sought, i.e., a preselected antigen. The immunization can be carried out conventionally. Antibody titer in the animal can be monitored to determine the stage of immunization desired, which stage corresponds to the amount of enrichment or biasing of the repertoire desired. Partially immunized animals typically receive only one immunization and cells are collected from those animals shortly after a response is detected. Fully immunized animals display a peak titer, which is achieved with one or more repeated injections of the antigen into the host mammal, normally at 2 to 3 week intervals. Usually three to five days after the last challenge, the spleen is removed and the genetic repertoire of the splenocytes, about 90% of which are rearranged B cells, is isolated using standard procedures. See, *Current Protocols in Molecular Biology*, Ausubel et al., eds., John Wiley & Sons, NY. Nucleic acids coding for $V_H$ and $V_L$ polypeptides can be derived from cells producing IgA, IgD, IgE, IgG or IgM, most preferably from IgM and IgG, producing cells.

Methods for preparing fragments of genomic DNA from which immunoglobulin variable region genes can be cloned as a diverse population are well known in the art. See for example Herrmann et al., *Methods In Enzymol.*, 152:180–183, (1987); Frischauf, *Methods In Enzymol.*, 152:183–190 (1987); Frischauf, *Methods In Enzymol.*, 152:190–199 (1987); and DiLella et al., *Methods In Enzymol.*, 152:199–212 (1987). (The teachings of the references cited herein are hereby incorporated by reference.)

The desired gene repertoire can be isolated from either genomic material containing the gene expressing the variable region or the messenger RNA (mRNA) which represents a transcript of the variable region. The difficulty in using the genomic DNA from other than non-rearranged B lymphocytes is in juxtaposing the sequences coding for the variable region, where the sequences are separated by introns. The DNA fragment(s) containing the proper exons must be isolated, the introns excised, and the exons then spliced in the proper order and in the proper orientation. For the most part, this will be difficult, so that the alternative technique employing rearranged B cells will be the method of choice because the V, D and J immunoglobulin gene regions have translocated to become adjacent, so that the sequence is continuous (free of introns) for the entire variable regions.

Where mRNA is utilized the cells will be lysed under RNase inhibiting conditions. In one embodiment, the first step is to isolate the total cellular mRNA. Poly A+ mRNA can then be selected by hybridization to an oligo-dT cellulose column. The presence of mRNAs coding for the heavy and/or light chain polypeptides can then be assayed by hybridization with DNA single strands of the appropriate genes. Conveniently, the sequences coding for the constant portion of the $V_H$ and $V_L$ can be used as polynucleotide probes, which sequences can be obtained from available sources. See for example, Early and Hood, *Genetic Engineering*, Setlow and Hollaender, eds., Vol. 3, Plenum Publishing Corporation, NY, (1981), pages 157–188; and Kabat et al., *Sequences of Immunological Interest*, National Institutes of Health, Bethesda, Md., (1987).

In preferred embodiments, the preparation containing the total cellular mRNA is first enriched for the presence of $V_H$ and/or $V_L$ coding mRNA. Enrichment is typically accomplished by subjecting the total mRNA preparation or partially purified mRNA product thereof to a primer extension reaction employing a polynucleotide synthesis primer as described herein. Exemplary methods for producing $V_H$ and $V_L$ gene repertoires using polynucleotide synthesis primers are described in PCT Application No. PCT/US 90/02836 (International Publication No. WO 90/14430). Particularly preferred methods for producing a gene repertoire rely on the use of preselected oligonucleotides as primers in a polymerase chain reaction (PCR) to form PCR reaction products as described herein.

In preferred embodiments, isolated B cells are immunized in vitro against a preselected antigen. In vitro immunization is defined as the clonal expansion of epitope-specific B cells in culture, in response to antigen stimulation. The end result is to increase the frequency of antigen-specific B cells in the immunoglobulin repertoire, and thereby decrease the number of clones in an expression library that must be screened to identify a clone expressing an antibody of the desired specificity. The advantage of in vitro immunization is that human monoclonal antibodies can be generated against a limitless number of therapeutically valuable antigens, including toxic or weak immunogens. For example, antibodies specific for the polymorphic determinants of tumor-associated antigens, rheumatoid factors, and histocompatibility antigens can be produced, which can not be elicited in immunized animals. In addition, it may be possible to generate immune responses which are normally suppressed in vivo.

In vitro immunization can be used to give rise to either a primary or secondary immune response. A primary immune response, resulting from first time exposure of a B cell to an antigen, results in clonal expansion of epitope-specific cells and the secretion of IgM antibodies with low to moderate apparent affinity constants ($10^6$–$10^8$ $M^{-1}$). Primary immunization of human splenic and tonsillar lymphocytes in culture can be used to produce monoclonal antibodies against a variety of antigens, including cells, peptides, macromolecule, haptens, and tumor-associated antigens. Memory B cells from immunized donors can also be stimulated in culture to give rise to a secondary immune response characterized by clonal expansion and the production of high affinity antibodies ($>10^9$ $M^{-1}$) of the IgG isotype, particularly against viral antigens by clonally expanding sensitized lymphocytes derived from seropositive individuals.

In one embodiment, peripheral blood lymphocytes are depleted of various cytolytic cells that appear to downmodulate antigen-specific B cell activation. When lysosome-rich subpopulations (natural killer cells, cytotoxic and suppressor T cells, monocytes) are first removed by treatment with the lysosmotropic methyl ester of leucine, the remaining cells (including B cells, T helper cells, accessory cells) respond antigen-specifically during in vitro immunization. The lymphokine requirements for inducing antibody production in culture are satisfied by a culture supernatant from activated, irradiated T cells.

In addition to in vitro immunization, cell panning (immunoaffinity absorption) can be used to further increase the frequency of antigen-specific B cells. Techniques for selecting B cell subpopulations via solid-phase antigen binding are well established. Panning conditions can be optimized to selectively enrich for B cells which bind with high affinity to a variety of antigens, including cell surface proteins. Panning can be used alone, or in combination with in vitro immunization to increase the frequency of antigen-specific cells above the levels which can be obtained with either technique alone. Immunoglobulin expression libraries constructed from enriched populations of B cells are biased in favor of antigen-specific antibody clones, and thus, enabling identification of clones with the desired specificities from smaller, less complex libraries.

In one embodiment, donor peripheral blood lymphocytes (PBL) can be transferred into severe combined immunodeficiency (SCID) mice and then boosted in vivo in the SCID mice to increase the immune response prior to harvesting the heavy and light chain coding nucleic acids from the SCID mouse's B cells. See for example, Duchosal et al, *Nature*, 355:258–262 (1992). In that report, human PBLs from a donor who had anti-tetanus toxoid (TT) titers were boosted while in the SCID mouse host. The resulting library of 370,000 clones yielded 2 phage particles expressing a surface Fab able to bind TT.

3. Preparation of Polynucleotide Primers

The term "polynucleotide" as used herein in reference to primers, probes and nucleic acid fragments or segments to be synthesized by primer extension is defined as a molecule comprised of two or more deoxyribonucleotide or ribonucleotides, preferably more than 3. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on may factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarily with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nucl. Acids Res.*, 12:7057–70 (1984); Studier et al., *J. Mol. Biol.*, 189:113–130 (1986); and *Molecular Cloning: A Laboratory Manual, Second Edition*, Maniatis et al., eds., Cold Spring Harbor, N.Y. (1989).

When a primer containing a DNA-dependent RNA polymerase promoter is used the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology*, 6:1197–1202 (1988). RNA-directed polymerases produce large-numbers of RNA strands from a small number of template RNA strands that contain a template sequence or replication initiation site. These polymerases typically give a one million-fold amplification of the template strand as has been described by Kramer et al., *J. Mol. Biol.*, 89:719–736 (1974).

The polynucleotide primers can be prepared using any suitable method, such as, for example, the phosphotriester or phosphodiester methods see Narang et al., *Meth. Enzymol.*, 68:90, (1979); U.S. Pat. No. 4,356,270; and Brown et al., *Meth. Enzymol.*, 68:109, (1979).

The choice of a primer's nucleotide sequence depends on factors such as the distance on the nucleic acid from the region coding for the desired receptor, its hybridization site on the nucleic acid relative to any second primer to be used, the number of genes in the repertoire it is to hybridize to, and the like.

a. Primers for Producing
Immunoglobulin Gene Repertoires $V_H$ and $V_L$ gene repertoires can be separately prepared prior to their utilization in the present invention. Repertoire preparation is typically accomplished by primer extension, preferably by primer extension in a polymerase chain reaction (PCR) format.

To produce a repertoire of $V_H$-coding DNA homologs by primer extension, the nucleotide sequence of a primer is selected to hybridize with a plurality of immunoglobulin heavy chain genes at a site substantially adjacent to the $V_H$-coding region so that a nucleotide sequence coding for a functional (capable of binding) polypeptide is obtained. To hybridize to a plurality of different $V_H$-coding nucleic acid strands, the primer must be a substantial complement of a nucleotide sequence conserved among the different strands. Such sites include nucleotide sequences in the constant region, any of the variable region framework regions, preferably the third framework region, leader region, promoter region, J region and the like.

It the repertoires of $V_H$-coding and $V_L$-coding DNA homologs are to be produced by (PCR) amplification, two primers, i.e., a PCR primer pair, must be used for each coding strand of nucleic acid to be amplified. The first primer becomes part of the nonsense (minus or complementary) strand and hybridizes to a nucleotide sequence conserved among $V_H$ (plus or coding) strands within the repertoire. To produce $V_H$ coding DNA homologs, first primers are therefore chosen to hybridize to (i.e. be complementary to) conserved regions within the J region, CH1 region, hinge region, CH2 region, or CH3 region of immunoglobulin genes and the like. To produce a $V_L$ coding DNA homolog, first primers are chosen to hybridize with (i.e. be complementary to) a conserved region within the J region or constant region of immunoglobulin light chain genes and the like. Second primers become part of the coding (plus) strand and hybridize to a nucleotide sequence conserved among minus strands. To produce the $V_H$-coding DNA homologs, second primers are therefore chosen to hybridize with a conserved nucleotide sequence at the 5' end of the $V_H$-coding immunoglobulin gene such as in that area coding for the leader or first framework region. It should be noted that in the amplification of both $V_H$- and $V_L$-coding DNA homologs the conserved 5' nucleotide sequence of the second primer can be complementary to a sequence exogenously added using terminal deoxynucleotidyl transferase as described by Loh et al., *Science*, 243:217–220 (1989). One or both of the first and second primers can contain a nucleotide sequence defining an endonuclease recognition site. The site can be heterologous to the immunoglobulin gene being amplified and typically appears at or near the 5' end of the primer.

When present, the restriction site-defining portion is typically located in a 5'-terminal non-priming portion of the primer. The restriction site defined by the first primer is typically chosen to be one recognized by a restriction enzyme that does not recognize the restriction site defined by the second primer, the objective being to be able to produce a DNA molecule having cohesive termini that are non-complementary to each other and thus allow directional insertion into a vector.

In one embodiment, the present invention utilizes a set of polynucleotides that form primers having a priming region located at the 3'-terminus of the primer. The priming region is typically the 3'-most (3'-terminal) 15 to 30 nucleotide bases. The 3'-terminal priming portion of each primer is capable of acting as a primer to catalyze nucleic acid synthesis, i.e., initiate a primer extension reaction off its 3' terminus. One or both of the primers can additionally contain a 5'-terminal (5'-most) non-priming portion, i.e., a region that does not participate in hybridization to repertoire template.

In PCR, each primer works in combination with a second primer to amplify a target nucleic acid sequence. The choice of PCR primer pairs for use in PCR is governed by considerations as discussed herein for producing gene repertoires. That is, the primers have a nucleotide sequence that is complementary to a sequence conserved in the repertoire. Useful $V_H$ and $V_L$ priming sequences are shown in Tables 5 and 6, herein below.

4. Polymerase Chain Reaction to Produce Gene Repertoires

The strategy used for cloning the $V_H$ and $V_L$ genes contained within a repertoire will depend, as is well known in the art, on the type, complexity, and purity of the nucleic acids making up the repertoire. Other factors include whether or not the genes are contained in one or a plurality of repertoires and whether or not they are to be amplified and/or mutagenized.

The $V_H$- and $V_L$-coding gene repertoires are comprised of polynucleotide coding strands, such as mRNA and/or the sense strand of genomic DNA. If the repertoire is in the form of double stranded genomic DNA, it is usually first denatured, typically by melting, into single strands. A repertoire is subjected to a PCR reaction by treating (contacting) the repertoire with a PCR primer pair, each member of the pair having a preselected nucleotide sequence. The PCR primer pair is capable of initiating primer extension reactions by hybridizing to nucleotide sequences, preferably at least about 10 nucleotides in length and more preferably at least about 20 nucleotides in length, conserved within the repertoire. The first primer of a PCR primer pair is sometimes referred to herein as the "sense primer" because it hybridizes to the coding or sense strand of a nucleic acid. In addition, the second primer of a PCR primer pair is sometimes referred to herein as the "anti-sense primer" because it hybridizes to a non-coding or anti-sense strand of a nucleic acid, i.e., a strand complementary to a coding strand.

The PCR reaction is performed by mixing the PCR primer pair, preferably a predetermined amount thereof, with the nucleic acids of the repertoire, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing a plurality of different $V_H$-coding and/or $V_L$-coding DNA homologs.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined to increase the diversity of the gene library.

In another strategy, the object is to clone the $V_H$- and/or $V_L$-coding genes from a repertoire by providing a polynucleotide complement of the repertoire, such as the anti-sense strand of genomic dsDNA or the polynucleotide produced by subjecting mRNA to a reverse transcriptase reaction. Methods for producing such complements are well known in the art.

The PCR reaction is performed using any suitable method. Generally it occurs in a buffered aqueous solution, i.e., a PCR buffer, preferably at a pH of 7–9, most preferably about 8. Preferably, a molar excess (for genomic nucleic acid, usually about $10^{6:1}$ primer:template) of the primer is admixed to the buffer containing the template strand. A large molar excess is preferred to improve the efficiency of the process.

The PCR buffer also contains the deoxyribonucleotide triphosphates dATP, dCTP, dGTP, and dTTP and a polymerase, typically thermostable, all in adequate amounts for primer extension (polynucleotide synthesis) reaction. The resulting solution (PCR admixture) is heated to about 90° C.–100° C. for about 1 to 10 minutes, preferably from 1 to 4 minutes. After this heating period the solution is allowed to cool to 54° C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. An exemplary PCR buffer comprises the following: 50 mM KCl; 10 mM Tris-HCl; pH 8.3; 1.5 mM $MgCl_2$; 0.001% (wt/vol) gelatin, 200 μM dATP; 200 μM dTTP; 200 μM dCTP; 200 μM dGTP; and 2.5 units Thermus acuaticus DNA polymerase I (U.S. Pat. No. 4,889,818) per 100 microliters of buffer.

The inducing agent may be any compound or system which will function to accomplish the synthesis of primer extension products, including enzymes.

Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., The Enzymes, ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., Nuc. Acid Res., 17:711–722 (1989). Amplification systems based on transcription have been described by Gingeras et al., in PCR Protocols, A Guide to Methods and Applications, pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process.

The first and/or second PCR reactions discussed above can advantageously be used to incorporate into the receptor a preselected epitope useful in immunologically detecting and/or isolating a receptor. This is accomplished by utilizing a first and/or second polynucleotide synthesis primer or expression vector to incorporate a predetermined amino acid residue sequence into the amino acid residue sequence of the receptor.

After producing $V_H$- and $V_L$-coding DNA homologs for a plurality of different $V_H$- and $V_L$-coding genes within the repertoires, the DNA molecules are typically further amplified. While the DNA molecules can be amplified by classic techniques such as incorporation into an autonomously replicating vector, it is preferred to first amplify the molecules by subjecting them to a polymerase chain reaction (PCR) prior to inserting them into a vector. PCR is typically carried out by thermocycling i.e., repeatedly increasing and decreasing the temperature of a PCR reaction admixture within a temperature range whose lower limit is about 10° C. to about 40° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,195, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

In preferred embodiments only one pair of first and second primers is used per amplification reaction. The amplification reaction products obtained from a plurality of different amplifications, each using a plurality of different primer pairs, are then combined.

However, the present invention also contemplates DNA homolog production via co-amplification (using two pairs of primers), and multiplex amplification (using up to about 8, 9 or 10 primer pairs).

In preferred embodiments, the PCR process is used not only to produce a library of DNA molecules, but also to induce mutations within the library or to create diversity from a single parental clone and thereby provide a library having a greater heterogeneity. First, it should be noted that the PCR process itself is inherently mutagenic due to a variety of factors well known in the art. Second, in addition to the mutation inducing variations described in the above referenced U.S. Pat. No. 4,683,195, other mutation inducing PCR variations can be employed. For example, the PCR reaction admixture, can be formed with different amounts of one or more of the nucleotides to be incorporated into the extension product. Under such conditions, the PCR reaction proceeds to produce nucleotide substitutions within the extension product as a result of the scarcity of a particular base. Similarly, approximately equal molar amounts of the nucleotides can be incorporated into the initial PCR reaction admixture in an amount to efficiently perform X number of cycles, and then cycling the admixture through a number of cycles in excess of X, such as, for instance, 2X. Alternatively, mutations can be induced during the PCR reaction by incorporating into the reaction admixture nucleotide derivatives such as inosine, not normally found in the nucleic acids of the repertoire being amplified. During subsequent in vivo DNA synthesis and replication of the nucleic acids in a host cell, the nucleotide derivative will be replaced with a substitute nucleotide thereby inducing a point mutation.

5. Linear DNA Expression Vectors

A DNA expression vector for use in a method of the invention for producing a library of DNA molecules is a linearized DNA molecule as described before having two (upstream and downstream) cohesive termini adapted for directional ligation to a polypeptide gene.

A linear DNA expression vector is typically prepared by restriction endonuclease digestion of a circular DNA expression vector of this invention to cut at two preselected restriction sites within the sequence of nucleotides of the vector adapted for directional ligation to produce a linear DNA molecule having the required cohesive termini that are adapted for direction ligation. Directional ligation refers to the presence of two (a first and second) cohesive termini on a vector, or on the insert DNA molecule to be ligated into the vector selected, so that the termini on a single molecule are not complementary. A first terminus of the vector is complementary to a first terminus of the insert, and the second terminus of the vector is complementary to the second terminus of the insert.

6. Ligation Reactions to Produce Gene Libraries

In preparing a library of DNA molecules of this invention, a ligation admixture is prepared as described above, and the admixture is subjected to ligation conditions for a time period sufficient for the admixed repertoire of polypeptide genes to ligate (become operatively linked) to the plurality of DNA expression vectors to form the library.

Ligation conditions are conditions selected to favor a ligation reaction wherein a phosphodiester bond is formed between adjacent 3' hydroxyl and 5' phosphoryl termini of DNA. The ligation reaction is preferably catalyzed by the enzyme T4 DNA ligase. Ligation conditions can vary in time, temperature, concentration of buffers, quantities of DNA molecules to be ligated, and amounts of ligase, as is well known. Preferred ligation conditions involve maintaining the ligation admixture at 4 degrees Centigrade (4° C.) to 12° C. for 1 to 24 hours in the presence of 1 to 10 units of T4 DNA ligase per milliliter (ml) and about 1 to 2 micrograms (ug) of DNA. Ligation buffer in a ligation admixture typically contains 0.5 M Tris-HCl (pH 7.4), 0.01 M $MgCl_2$, 0.01 M dithiothrietol, 1 mM spermidine, 1 mM ATP and 0.1 mg/ml bovine serum albumin (BSA). Other ligation buffers can also be used.

Exemplary ligation reactions are described in Example 2.

7. Preparation of Dicistronic Gene Libraries

In a particularly preferred embodiment, the present invention contemplates methods for the preparation of a library of dicistronic DNA molecules. A dicistronic DNA molecule is a single DNA molecule having the capacity to express two separate polypeptides from two separate cistrons. In preferred embodiments, the two cistrons are operatively linked at relative locations on the DNA molecule such that both cistrons are under the transcriptional control of a single promoter. Each dicistronic molecule is capable of expressing first and second polypeptides from first and second cistrons, respectively, that can form, in a suitable host, a heterodimeric receptor on the surface of a filamentous phage particle.

The method for producing a library of dicistronic DNA molecules comprises the steps of:

(a) Forming a first ligation admixture by combining in a ligation buffer:
  (i) a repertoire of first polypeptide genes in the form of dsDNA, each having cohesive termini adapted for directional ligation, and
  (ii) a plurality of DNA expression vectors in linear form, each having upstream and downstream first cohesive termini that are (a) adapted for directionally receiving the first polypeptide genes in a common reading frame, and (b) operatively linked to respective upstream and downstream translatable DNA sequences. The upstream translatable DNA sequence encodes a pelB secretion signal, the downstream translatable DNA sequence encodes a filamentous phage coat protein membrane anchor, and translatable DNA sequences are operatively linked to respective upstream and downstream DNA expression control sequences.

(b) Subjecting the admixture to ligation conditions for a time period sufficient to operatively link the first polypeptide genes to the vectors and produce a plurality of circular DNA molecules each having a first cistron for expressing the first polypeptide.

(c) Treating the plurality of circular DNA molecules under DNA cleavage conditions to produce a plurality of DNA expression vectors in linear form that each have upstream and downstream second cohesive termini that are (i) adapted for directionally receiving a repertoire of second polypeptide genes in a common reading frame, and (ii) operatively linked to respective upstream and downstream DNA sequences. The upstream DNA sequence is a translatable sequence encoding a secretion signal, the downstream DNA sequence has at least one stop codon in the reading frame, and the translatable DNA sequence is operatively linked to a DNA expression control sequence.

(d) Forming a second ligation admixture by combining in a ligation buffer:
  (i) the plurality of DNA expression vectors formed in step (c), and
  (ii) the repertoire of second polypeptide genes in the form of dsDNA, each having cohesive termini adapted for directional ligation to the plurality of DNA expression vectors; and (e) Subjecting the second admixture to ligation conditions for a time period sufficient to operatively link the second polypeptide genes to said vectors and produce a plurality of circular DNA molecules each having the second cistron for expressing the second polypeptide, thereby forming the library.

In preferred embodiments a secretion signal is a pelB secretion signal. Also preferred is the use of a filamentous phage membrane anchor that is derived from cpIII or cpVIII as described herein.

DNA expression vectors useful for practicing the above method are the dicistronic expression vectors described in greater detail before.

In practicing the method of producing a library of dicistronic DNA molecules, it is preferred that the upstream and downstream first cohesive termini do not have the same nucleotide sequences as the upstream and downstream second cohesive termini. In this embodiment, the treating step (c) to linearize the circular DNA molecules typically involves the use of restriction endonucleases that are specific for producing said second termini, but do not cleave the circular DNA molecule at the sites that formed the first termini. Exemplary and preferred first and second termini are the termini defined by cleavage of pCBAK8 with Xho I and Spe I to form the upstream and downstream first termini, and defined by cleavage of pCBAK8 with Sac I and Xba I to form the upstream and downstream second termini. In this embodiment, other pairs of cohesive termini can be utilized at the respective pairs of first and second termini, so long as the four termini are each distinct, non-complementary termini. Exemplary are the termini found on the vectors pCOMB3, pCOMB2-3, pCOMB2-3', pCOMB8 and pCOMB2-8 described herein.

Methods of treating the plurality of circular DNA molecules under DNA cleavage conditions to form linear DNA molecules are generally well known and depend on the nucleotide sequence to be cleaved and the mechanism for cleavage. Preferred treatments involve admixing the DNA molecules with a restriction endonuclease specific for a endonuclease recognition site at the desired cleavage location in an amount sufficient for the restriction endonuclease to cleave the DNA molecule. Buffers, cleavage conditions, and substrate concentrations for restriction endonuclease cleavage are well known and depend on the particular enzyme utilized. Exemplary restriction enzyme cleavage conditions are described in Example 2.

In a related embodiment, the invention provides a method for producing a library of DNA molecules having a single cistron, following the method described previously and stopping after completing step (b). Such a library contains DNA molecules each comprising a cistron for expressing a polypeptide of this invention.

8. Methods for Changing the Diversity of a Library

The present invention provides methods for changing the diversity of a library of filamentous phage library of this invention. These methods generally increase the diversity of the library, thereby increasing the pool of possible epitope-binding complexes from which to screen for a desired binding activity. Alternatively, the methods can be directed at enriching for a class of epitope-binding complexes. The class is typically defined by the ability to bind a particular epitope or family of epitopes present on a preselected antigen or group of antigens.

a. Increasing Library Diversity by Mutation

A particularly preferred method for increasing diversity is to alter the amino acid residue sequence of one or more polypeptides of the epitope-binding complex encoded by the genome of a phage of this invention. Alterations can be conveniently introduced at the nucleic acid level by mutation of the nucleic acid. The method can be practiced on a single species of nucleic acid coding a polypeptide of this invention, or can be practiced on a library of nucleic acids present in a library of phage of this invention.

Mutation of nucleic acid can be conducted by a variety of means, but is most conveniently conducted in a PCR reaction during a PCR process of the present invention. PCR mutagenesis can be random or directed to specific nucleotide sequences, as is generally well known. Conducting PCR under conditions favorable to random mutagenesis has been described previously, and is referred to as "error prone PCR". Similarly, directed mutagenesis involves the use of PCR primers designed to target a specific type of mutation into a specific region of nucleotide sequence.

In one embodiment, the invention contemplates increasing diversity of one or more epitope-binding s complexes by PCR-directed mutation of a complementarity determining region (CDR) of an antibody variable domain present in an epitope-binding complex polypeptide of this invention. CDR mutagenesis has been previously described in general terms for "humanizing" an antibody by introducing human sequences into the CDR region of a murine antibody. See European Application No. EP 239400.

Thus the invention contemplates a mutagenesis method for altering the immunological specificity of a cloned immunoglobulin gene present in a DNA vector of this invention. The method provides directed mutagenesis in a preselected CDR of an immunoglobulin gene which comprises subjecting a recombinant DNA molecule (rDNA) containing the cloned immunoglobulin gene having a target CDR to PCR conditions suitable for amplifying a preselected region of the CDR. In the method, the rDNA molecule is subjected to PCR conditions that include a PCR primer oligonucleotide as described below constituting the first primer in a PCR primer pair as is well known to produce an amplified PCR product that is derived from the preselected CDR region but that includes the nucleotide sequences of the PCR primer. The second oligonucleotide in the PCR amplifying conditions can be any PCR primer derived from the immunoglobulin gene to be mutagenized, as described herein.

Preferred are methods using an oligonucleotide of this invention as described below.

In a related embodiment, therefore, an oligonucleotide is contemplated that is useful as a primer in a polymerase chain reaction (PCR) for inducing mutagenesis in a complementarity determining region (CDR) of an immunoglobulin gene. The oligonucleotide has 3' and 5' termini and comprises (1) a nucleotide sequence at its 3' terminus capable of hybridizing to a first framework region of an immunoglobulin gene, (2) a nucleotide sequence at its 5' terminus capable of hybridizing to a second framework region of an immunoglobulin gene, and (3) a nucleotide sequence between the 3' and 5' termini adapted for introducing mutations during a PCR into the CDR region between the first and second framework regions of the immunoglobulin gene, thereby mutagenizing the CDR region.

Insofar as immunoglobulin genes have three CDR regions on both the heavy chain and the light chain of an immunoglobulin, each separated by a distinctive framework region, it is to be understood that the above example is readily applicable to introducing mutations into a specific CDR by selection of the above 5' and 3' nucleotide sequences as to hybridize to the framework regions flanking the targeted CDR. Thus the above first and second framework sequences can be the conserved sequences flanking CDR1, CDR2 or CDR3 on either the heavy or light chain. Exemplary and preferred is the CDR3 of the human immunoglobulin heavy chain.

The length of the 3' and 5' terminal nucleotide sequences of a subject mutagenizing oligonucleotide can vary in length as is well known, so long as the length provides a stretch of nucleotides complementary to the target framework sequences as to hybridize thereto. In the case of the 3' terminal nucleotide sequence, it must be of sufficient length and complementarity to the target framework region located 3' to the CDR region to be mutagenized as to hybridize and provide a 3'hydroxyl terminus for initiating a primer extension reaction. In the case of the 5' terminal nucleotide sequence, it must be of sufficient length and complementarity to the target framework region located 5' to the CDR region to be mutagenized as to provide a means for hybridizing in a PCR overlap extension reaction as described above to assemble the complete immunoglobulin heavy or light chain.

Framework regions flanking a CDR are well characterized in the immunological arts, and include known nucleotide sequences or consensus sequences as described elsewhere herein. Where a single, preselected immunoglobulin gene is to be mutagenized, the framework-defined sequences flanking a particular CDR are known, or can be readily determined by nucleotide sequencing protocols. Where a repertoire of immunoglobulin genes are to be mutagenized, the framework-derived sequences are preferably conserved, as described elsewhere herein.

Preferably, the length of the 3' and 5' terminal nucleotide sequences are each at least 6 nucleotides in length, and can be up to 50 or more nucleotides in length, although these lengths are unnecessary to assure accurate and reproducible hybridization. Preferred are lengths in the range of 12 to 30 nucleotides, and typically are about 18 nucleotides.

A particularly preferred framework-defined nucleotide sequence for use as a 3' terminus nucleotide sequence has the nucleotide sequence 5'-TGGGGCCAAGGGACCACG-3' (SEQ ID NO 122).

A particularly preferred framework-defined nucleotide sequence for use as a 5' terminus nucleotide sequence has the nucleotide sequence 5'-GTGTATTATTGTGCGAGA-3' (SEQ ID NO 123).

The nucleotide sequence located between the 3' and 5' termini adapted for mutagenizing a CDR can be any nucleotide sequence, insofar as the novel sequence will be incorporated by the above methods. However, the present approach provides a means to produce a large population of mutagenized CDR's in a single PCR reaction by the use of a population of redundant sequences defining randomized or nearly randomized nucleotides in the CDR region to be mutagenized.

A preferred oligonucleotide comprises a nucleotide sequence between the above described 3' and 5' termini that is represented by the formula: [NNB]$_n$, wherein N can independently be any nucleotide, B can be G, C or T or analogs thereof, and where n is from 3 to about 24. In preferred embodiments, the oligonucleotide has the formula: 5'-GTGTATTATTGTGCGAGA[NNB]$_n$ TGGGGCCAAGGGACCACG-3' (SEQ ID NO 124).

Exemplary and particularly preferred is the oligonucleotide where B is G or C and n is 16, such that the oligonucleotide represents a large population of redundant oligonucleotide sequences.

Thus, the invention contemplates a method for increasing the diversity of a library of filamentous phage particles comprising the steps of: a) providing a library of filamentous phage particles according to the present invention, and b) mutating the immunoglobulin variable domain-coding nucleotide sequence present in each DNA expression vector in the library to form a library of phage particles each containing a mutated immunoglobulin variable domain nucleotide sequence.

The providing can include manipulating the genomes of the phage particles in the library in order to isolate the nucleic acids in preparation for a mutagenizing PCR reaction. Manipulations of a phage library to isolate the phage genome for use in a PCR reaction is described elsewhere herein.

In one embodiment, the mutating comprises subjecting the immunoglobulin variable domain-coding nucleotide sequence to an error-prone polymerase chain reaction. In another embodiment, the mutating comprises subjecting the immunoglobulin variable domain-coding nucleotide sequence to a method for mutating a CDR of the immunoglobulin variable domain-coding nucleotide sequence using a CDR-directed oligonucleotide as described herein.

Exemplary methods of mutating the CDR region of a particular epitope-binding complex coding nucleic acid using the above CDR-directing oligonucleotide or using error-prone PCR to produce a large library of diverse complexes is described in the Examples.

b. Enrichment of a Library

The invention describes a method to change the diversity of the library by enriching the library for a preselected class of epitope-binding complexes. The process generally involves affinity selection of those phage particles in a library that are capable of binding a preselected antigen. The process of affinity selection, or panning, is described in detail in the Examples.

Thus the invention contemplates a method for changing the diversity of a library of filamentous phage particles comprising the steps of a) providing a library of filamentous phage particles according to the present invention, b) contacting the provided library with a preselected ligand under conditions sufficient for members of the library to bind to the ligand and form a ligand-phage particle complex, and c) isolating phage particles in the complex away from non-bound library members to form a ligand-enriched library comprising phage particles having binding specificity for the preselected ligand.

In preferred embodiments, the preselected ligand is affixed to a solid support, and the ligand-phage particle complex is formed in the solid phase. This embodiment further comprises the steps of i) washing the solid support after the contacting step to rinse non-bound library members from the solid support; and ii) eluting any solid-phase bound phage particles off of the solid support. The eluted phage particles are collected, thereby forming isolated phage particles that comprise an enriched library.

Elution can be conducted under a variety of conditions that disrupt the ligand-epitope-binding complex interaction. Typical conditions include high salt or low pH buffers. Particularly preferred are buffers of about pH 1 to 5, preferably about pH 2 to 3. Alternatively, the interaction can be disrupted by competition with an excess amount of the preselected ligand in the elution buffer. Both elution procedures are described in the Examples.

A related embodiment combines the features of both increasing diversity of a library by mutation and enriching the library by panning to "mature" epitope-binding complex affinities for a preselected ligand. Thus it is possible to evolve new binding specificities, and more potent binding specificities, using the present methods for changing library diversity.

The combination of these methods can be configured in a variety of ways, as will be apparent to a skilled practitioner. For example, one can isolate a library, mutagenize (diversify), and then screen (enrich) for a particular binding activity. Alternatively, one can enrich for a particular activity from a library, mutagenize the specific epitope-binding complex and further enrich the library produced by the mutagenesis.

In another permutation on this theme, one can utilize the differences between libraries based on cpIII- and cpVIII-derived membrane anchors due to their inherent differences in valency. Because a library of phage having the cpIII-derived membrane anchor will typically contain only 1 to 4 copies of the epitope-binding complex on the surface of each phage particle, the phage presents a binding complex is of relatively "low" valency, approaching one. In contrast, a library of phage having a cpVIII-derived membrane anchor will typically contain 20 to 1000 copies of the epitope-binding complex on the surface of each phage particle, the particle presents a relatively "high" valency. Thus, cpIII-based libraries are referred to as monovalent and cpVIII-based libraries are referred to as multivalent.

Applying the well-known principles of antibody affinity and valence, it is understood that a cpIII-based library can be enriched upon screening for generally higher affinity binding interactions (binding constants of $10^6$ to $10^9$ $M^{-1}$) as compared to the broader range of affinities (binding constants of $10^4$ to $10^9$ $M^{-1}$) isolatable using a multivalent reagent found in the cpVIII-based library. Therefore, a cpVIII-based library is useful to isolate a broad range of affinities of epitope-binding complexes from low to high, whereas a cpIII-based library is useful to isolate a narrower range of higher affinity epitope-binding complexes.

Thus the invention contemplates producing a first enriched library by enrichment of a cpVIII-based library. Thereafter the genes for encoding the epitope-binding complex polypeptides are transferred into a cpIII-based vector, and subsequently enriched for a high affinity binding interaction. In one embodiment, a mutation step can be utilized prior to the transfer into the cpIII-based vector.

In another embodiment, the ability to mature a novel affinity is shown by an example herein in which a cloned $V_H/V_L$ heterodimer-coding gene capable of expressing a heterodimer that binds the ligand tetanus toxoid (TT) is mutagenized using CDR-directed PCR mutagenesis, and the mutagenized nucleic acid population resulting therefrom is inserted into a cpIII-based library and screened for binding to a different ligand, fluorescein. A high affinity epitope-binding complex was identified that binds fluorescein.

In a related embodiment, a naive (non-immunized) library was cloned into a cpVIII-based library and screened for binding to the antigen progesterone. Low affinity binders were cloned into a cpIII-based library, and three high affinity binding clones identified that bind progesterone. The three clones were pooled, and the pool was subjected to error-prone PCR mutagenesis, and the resulting library of mutated nucleic acids were cloned into a cpIII-based vector and screened against progesterone to yield a high affinity epitope-binding complex that binds progesterone. Thus a high affinity complex was "matured" from a naive library.

Thus, the present invention also contemplates a method for maturing the affinity of an epitope-binding complex encoded by a filamemtous phage of this invention comprising the steps of a) providing the genome of a filamentous phage, b) mutating the immunoglobulin variable domain-coding nucleotide sequence present in the provided genome to form a library of phage particles containing a mutated immunoglobin variable domain nucleotide sequence, c) contacting the library formed in step (b) with a preselected ligand under conditions sufficient for members of the library to bind to the ligand and form a ligand-phage particle complex, and d) isolating phage particles in said complex away from non-bound library members to form a ligand-enriched library comprising phage particles having binding specificity for the preselected ligand.

F. Phage Libraries

The present invention contemplates a library of DNA molecules that each encode a fusion polypeptide of this invention where the library is in the form of a population of different filamentous phage particles each containing a different rDNA molecule of this invention. By different rDNA molecule is meant a rDNA molecule differing in nucleotide base sequence encoding a polypeptide of this invention when compared in nucleotide sequence to another rDNA molecule in the library.

Thus, a phage library is a population of filamentous phage, preferably f1, fd or M13 filamentous phage, each phage having packaged inside the particle a rDNA expression vector of this invention, the rDNA is encapsulated in the phage particle by the matrix proteins of the phage. Stated differently, a phage library contains a plurality of filamentous phage particles, each different phage particle containing at least one epitope-binding complex on its surface as described herein. A preferred library is comprised of phage particles containing DNA molecules that encode at least $10^6$, preferably $10^7$ and more preferably $10^{8-9}$ different fusion polypeptides of this invention. By different fusion polypeptides is meant fusion polypeptides differing in amino acid residue sequence. Even higher library diversities are available when the methods of random combination or mutagenesis are utilized as described herein to increase library diversity.

Where the packaged expression vector encodes first and second polypeptides of an autogenously assembling receptor, e.g. $V_H$ and $V_L$ polypeptides that form a Fab, the library can also be characterized as containing or expressing a multiplicity of receptor specificities. Thus, libraries express at least $10^5$, preferably at least $10^6$ and more preferably at least $10^7$ different receptors, such as different antibodies, T cell receptors, integrins and the like.

The size of the library can vary depending on a number of factors, particularly the method in which the library is produced. As used herein, size connotes the complexity or diversity of the library, that is the number of different species making up the library, rather than the absolute number of particles in the library.

Thus, where a library is produced by first separately cloning two repertoires of genes, corresponding to the first and second polypeptides, the resulting library size after randomly combining the two repertoires in the form of a dicistronic vector is greatly increased. For example, consider light chain and heavy chain variable antibody gene repertoires, each having $10^6$ different members. Combining the two repertoires theoretically yields a library of $10^{12}$ possible different dicistronic vector species.

An experimental system was designed to evaluate the ability to "shuffle" two repertoires as described above in order to generate greater diversity. The system utilized a combinatorial Fab library derived from a mouse immunized with the hapten para-nitrophenyl phosphonamidate (NPN). Twenty-two different clones were isolated, and the heavy and light chain coding nucleic acids were isolated and sequenced to determine that 21 of the 22 pairs were different at the level of nucleic acid sequence. The 22 NPN ligand-binding clones were randomly recombined (shuffled), and rescreened for binding to NPN.

Assuming that the heavy and light chains can only form ligand-binding heterodimeric receptor molecules if the original pairs are rejoined, the model predicts that 4.6 percent of the total combinations would provide ligand-binding combinations. Any higher percentage demonstrates that pairings other than the original pairs are also capable of binding NPN. The results showed that 27 percent of the clones isolated bound NPN, indicating a 5.8-fold increase in the library size of receptors able to bind NPN upon shuffling. This demonstrated increase is limited to those clones that bind NPN. Other members of the randomly shuffled library have the capacity to bind diverse, non-NPN, ligands. Thus, shuffling was shown to increase diversity.

Library complexity can also be increased using the methods herein for mutating nucleotide sequences in a pre-existing library of sequences. Stated in terms of amino acid residue differences for an expressed fusion polypeptide, there can be potentially a twenty-fold increase in library size for each amino acid residue position that is targeted for random mutation.

For example, using the complementarity determining region (CDR)-directed mutagenesis of antibody genes as described in the Examples, a linear region of 16 amino acid residues was targeted for random mutation. Starting with a single species and mutating all 16 residue positions through all possible combinations with a choice of 20 different amino acids would theoretically produce a library of $20^{16}$ different species, or $6 \times 10^{20}$ different species.

As described herein, a particular advantage of a filamentous phage in the present invention is that the DNA molecule present in the phage particle and encoding one or both of the members of the heterodimeric receptor can be segregated from other DNA molecules present in the library on the basis of the presence of the particular expressed fusion polypeptide the surface of the phage particle.

Isolation (segregation) of a DNA molecule encoding one or both members of a heterodimeric receptor is conducted by segregation of the filamentous phage particle containing the gene or genes of interest away from the population of other phage particles comprising the library. Segregation of phage particles involves the physical separation and propagation of individual phage particles away from other particles in the library. Methods for physical separation of filamentous phage particles to produce individual particles, and the propagation of the individual particles to form populations of progeny phage derived from the individual segregated particle are well known in the filamentous phage arts.

A preferred separation method involves the identification of the expressed heterodimer on the surface of the phage particle by means of a ligand binding specificity between the phage particle and a preselected ligand. Exemplary and preferred is the use of "panning" methods whereby a suspension of phage particles is contacted with a solid phase ligand (antigen) and allowed to specifically bind (or immunoreact where the heterodimer includes an immunoglobulin variable domain). After binding, non-bound particles are washed off the solid phase, and the bound phage particles are those that contain ligand-specific heterodimeric receptor (heterodimer) on their surface. The bound particles can then be recovered by elution of the bound particle from the solid phase, typically by the use of aqueous solvents that interfere with the ligand-receptor interaction. Typical solvent include buffers having high ionic strength, low pH, or an amount of soluble competing ligand sufficient to disrupt the receptor-ligand binding interaction.

An alternate method for separating a phage particle based on the ligand specificity of the surface-expressed heterodimer from a population of particles is to precipitate the phage particles from the solution phase by crosslinkage with the ligand. An exemplary and preferred crosslinking and precipitation method is described in detail in Example 4c.

The use of the above particle segregation methods provides a means for screening a population of filamentous phage particles present in a phage library of this invention. As applied to a phage library, screening can be utilized to enrich the library for one or more particles that express a heterodimer having a preselected ligand binding specificity. Where the library is designed to contain multiple species of heterodimers that all have some detectable measure of ligand binding activity, but differ in protein structure, antigenicity, ligand binding affinity or avidity, and the like, the screening methods can be utilized sequentially to first produce a library enriched for a preselected binding specificity, and then to produce a second library further enriched by further screening comprising one or more isolated phage particles. Methods for measuring ligand binding activities, antigenicity and the like interactions between a ligand and a receptor are generally well known and are not discussed further as they are not essential features of the present invention.

Thus, in one embodiment, a phage library is a population of particles enriched for a preselected ligand binding specificity.

In another embodiment, a phage library comprises a population of particles wherein each particle contains at least one fusion polypeptide of this invention on the surface of the phage particle. The actual amount of fusion polypeptide present on the surface of a phage particle depends, in part, on the choice of coat protein membrane anchor present in the fusion polypeptide.

Where the anchor is derived from cpIII, there are typically about 1 to 4 fusion polypeptides per phage particle. Where the anchor is derived from the more preferred cpVIII, there is the potential for hundreds of fusion polypeptides on the particle surface depending on the growth conditions and other factors as discussed herein. The actual amount of fusion polypeptides present on a phage particle can be adjusted by controlling the amount "captured" by the phage particle as it is being synthesized in a host cell.

Typically, a phage particle in a library of this invention contains from about 10 to about 500 cpVIII-derived fusion polypeptides on the surface of each particle, and more preferably about 20 to 50 fusion polypeptides per particle. Exemplary amounts of surface fusion polypeptide are shown by the electron micrographs described in Example 4a that describe particles having about 20 to 24 cpVIII-derived fusion polypeptides per particle.

In another embodiment, the present invention contemplates a population of phage particles that are the progeny of a single particle, and therefor all express the same heterodimer on the particle surface. Such a population of phage are homogeneous and clonally derived, and therefore provide a source for expressing large quantities of a particular fusion polypeptide. An exemplary clonally homogeneous phage population is described in Example 4.

A filamentous phage particle in a library of this invention is produced by standard filamentous phage particle preparation methods and depends on the presence in a DNA expression vector of this invention of a filamentous phage origin of replication as described herein to provide the signals necessary for (1) production of a single-stranded filamentous phage replicative form and (2) packaging of the replicative form into a filamentous phage particle. Such a DNA molecule can be packaged when present in a bacterial cell host upon introduction of genetic complementation to provide the filamentous phage proteins required for production of infectious phage particles. A typical and preferred method for genetic complementation is to infect a bacterial host cell containing a DNA expression vector of this invention with a helper filamentous phage, thereby providing the genetic elements required for phage particle assembly. Exemplary helper rescue methods are described herein at Example 2, and described by Short et al., *Nuc. Acids Res.*, 16:7583–7600 (1988).

The level of heterodimeric receptor captured on the surface of a filamentous phage particle during the process of phage particle extrusion from the host cell can be controlled by a variety of means. In one embodiment, the levels of fusion polypeptides are controlled by the use of strong promoters in the first and second cistrons for expressing the polypeptides, such that transcription of the fusion polypeptide cistrons occurs at a relative rate greater than the rate of transcription of the cpVIII gene on the helper phage. In another embodiment, the helper phage can have an amber mutation in the gene for expressing cpVIII, such that less wild-type cpVIII is transcribed in the host cell than fusion polypeptides, thereby leading to increased ratios of fusion polypeptide compared to cpVIII during the extrusion process.

In another embodiment, the amount of heterodimeric receptor on the phage particle surface can be controlled by controlling the timing between expression of fusion polypeptides and the superinfection by helper phage. After introduction of the expression vector into the host cell, longer delay times before the addition of helper phage will allow for increased accumulation of the fusion polypeptides in the host cell, thereby increasing the amount of fusion polypeptide captured by the extruding phage particle.

G. Diagnostic Methods

The present invention also describes a diagnostic system, preferably in kit form, for assaying for the presence of a preselected ligand, or antigen, in a sample where it is desirable to detect the presence, and preferably the amount, of the ligand or antigen in a sample according to the diagnostic methods described herein.

The sample can be a tissue, tissue extract, fluid sample or body fluid sample, such as blood, plasma or serum.

The diagnostic system includes, in an amount sufficient to perform at least one assay, a filamentous phage or ligand-binding heterodimeric receptor according to the present invention, as a separately packaged reagent.

Exemplary diagnostic systems for detecting a preselected ligand in the solid phase and utilizing a filamentous phage of this invention are described in the Examples.

Instructions for use of the packaged reagent(s) are also typically included.

As used herein, the term "package" refers to a solid matrix or material such as glass, plastic (e.g., polyethylene, polypropylene or polycarbonate), paper, foil and the like capable of holding within fixed limits a heterodimeric receptor, filamentous phage or library of phage of the present invention. Thus, for example, a package can be a glass vial used to contain milligram quantities of a contemplated labeled phage preparation, or it can be a microtiter plate well to which microgram quantities of a contemplated receptor or phage particle(s) have been operatively affixed, i.e., linked so as to be capable of binding a ligand.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

A diagnostic system of the present invention preferably also includes a label or indicating means capable of signaling the formation of a binding reaction complex containing a ligand-binding heterodimeric receptor or phage complexed with the preselected ligand.

The word "complex" as used herein refers to the product of a specific binding reaction such as an phage-ligand or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed polypeptide, or phage particle that is used in a diagnostic method. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$ indium of $^3$H.

The linking of labels, i.e., labeling of, polypeptides and proteins is well known in the art. For instance, proteins or phage can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or phage of the present invention. Exemplary specific binding agents are antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of a preselected ligand in a fluid sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample and is readily applicable to the present methods. A description of the ELISA technique is found in Chapter 22 of the 4th Edition of *Basic and Clinical Immunolocy* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in some embodiments, a polypeptide, or a phage of the present invention can be affixed to a solid matrix to form a solid support that comprises a package in the subject diagnostic systems.

A reagent is typically affixed to a solid matrix is by adsorption from an aqueous medium although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

H. Assay Methods

The present invention contemplates various assay methods for determining the presence, and preferably amount, of a preselected ligand, typically present in an aqueous composition such as a biological fluid sample using a heterodimeric receptor or phage of this invention as an ligand-binding reagent to form a binding reaction product whose amount relates, either directly or indirectly, to the amount of the preselected ligand in the sample.

Those skilled in the art will understand that there are numerous well known clinical diagnostic chemistry procedures in which a binding reagent of this invention can be used to form an binding reaction product whose amount relates to the amount of the ligand in a sample. Thus, while exemplary assay methods are described herein, the invention is not so limited.

Various heterogenous and homogeneous protocols, either competitive or noncompetitive, can be employed in performing an assay method of this invention.

In one embodiment, the invention contemplates a direct binding assay using a ligand-binding heterodimeric receptor of this invention as a binding reagent to detect the presence of a preselected ligand with which the receptor binds. The method comprises the steps of a) admixing a sample suspected to contain a preselected antigen with a ligand-binding heterodimeric receptor of this invention that binds to the preselected ligand under binding conditions sufficient for the ligand-binding heterodimeric receptor to bind the ligand and form a ligand-receptor complex; and b) detecting the presence of the ligand-receptor complex or the ligand-binding heterodimeric receptor in the complex.

Binding conditions are those that maintain the ligand-binding activity of the receptor. Those conditions include a temperature range of about 4 to 50 degrees Centigrade, a pH value range of about 5 to 9 and an ionic strength varying from about that of distilled water to that of about one molar sodium chloride.

The detecting step can be directed, as is well known in the immunological arts, to either the complex or the binding reagent (the receptor component of the complex). Thus, a secondary binding reagent such as an antibody specific for the receptor may be utilized.

Alternatively, the complex may be detectable by virtue of having used a labeled receptor molecule, thereby making the complex labeled. Detection in this case comprises detecting the label present in the complex.

In a preferred embodiment, the ligand-binding heterodimeric receptor is provided as an attachment on a filamentous phage particle, i.e., on the surface of the phage. An exemplary assay using a filamentous phage of this invention is described in an ELISA format in the Examples.

In another embodiment, a filamentous phage particle is detectably labeled, such as by a radioisotope incorporated in a protein or nucleic acid of the phage as described herein. In this embodiment, detection comprises detecting the label in the complex, and thereby detecting the presence of the ligand in the complex.

A further diagnostic method utilizes the multivalency of a filamentous phage particle to cross-link ligand, thereby forming an aggregation of multiple ligands and phage particles, producing a precipitable aggregate. This embodiment is comparable to the well known methods of immune precipitation. This embodiment comprises the steps of admixing a sample with a plurality of phage particle of this invention to form a binding admixture under binding conditions, followed by a separation step to isolate the formed binding complexes. Typically, isolation is accomplished by centrifugation or filtration to remove the aggregate from the admixture. The presence of binding complexes indicates the presence of the preselected ligand to be detected.

EXAMPLES

The following examples are intended to illustrate, but not limit, the scope of the invention.

1. Construction of a Dicistronic Expression Vector for Producing a Heterodimeric Receptor on Phase Particles To obtain a vector system for generating a large number of Fab antibody fragments that can be screened directly, expression libraries in bacteriophage Lambda have previously been constructed as described in Huse et al., *Science*, 246:1275–1281 (1989). These systems did not contain design features that provide for the expressed Fab to be targeted to the surface of a filamentous phage particle.

The main criterion used in choosing a vector system was the necessity of generating the largest number of Fab fragments which could be screened directly. Bacteriophage Lambda was selected as the starting point to develop an expression vector for three reasons. First, in vitro packaging of phage DNA was the most efficient method of reintroducing DNA into host cells. Second, it was possible to detect protein expression at the level of single phage plaques. Finally, the screening of phage libraries typically involved less difficulty with nonspecific binding. The alternative, plasmid cloning vectors, are only advantageous in the analysis of clones after they have been identified. This advantage was not lost in the present system because of the use of a dicistronic expression vector such as pCombVIII, thereby permitting a plasmid containing the heavy chain, light chain, or Fab expressing inserts to be excised.

a. Construction of Dicistronic Expression Vector pCOMB (i) Preparation of Lambda Zap ™II Lambda Zap™ II is a derivative of the original Lambda Zap (ATCC #40, 298) that maintains all of the characteristics of the original Lambda Zap including 6 unique cloning sites, fusion protein expression, and the ability to rapidly excise the insert in the form of a phagemid (Bluescript SK−), but lacks the SAM 100 mutation, allowing growth on many Non-Sup F strains, including XL1-Blue. The Lambda Zap™ II was constructed as described in Short et al., *Nuc. Acids Res.*, 16:7583–7600, 1988, by replacing the Lambda S gene contained in a 4254 base pair (bp) DNA fragment produced by digesting Lambda Zap with the restriction enzyme Nco I. This 4254 bp DNA fragment was replaced with the 4254 bp DNA fragment containing the Lambda S gene isolated from Lambda gt10 (ATCC #40,179) after digesting the vector with the restriction enzyme Nco I. The 4254 bp DNA fragment isolated from lambda gt10 was ligated into the original Lambda Zap vector using T4 DNA ligase and standard protocols such as those described in *Current Protocols in Molecular Biology*, Ausubel et al., eds., John Wiley and Sons, NY, 1987, to form Lambda Zap™ II.

(ii) Preparation of Lambda Hc2

To express a plurality of $V_H$-coding DNA homologs in an *E. coli* host cell, a vector designated Lambda Hc2 was constructed. The vector provided the following: the capacity to place the $V_H$-coding DNA homologs in the proper reading frame; a ribosome binding site as described by Shine et al., *Nature*, 254:34, 1975; a leader sequence directing the expressed protein to the periplasmic space designated the pelB secretion signal; a polynucleotide sequence that coded for a known epitope (epitope tag); and also a polynucleotide that coded for a spacer protein between the $V_H$-coding DNA homolog and the polynucleotide coding for the epitope tag. Lambda Hc2 has been previously described by Huse et al., *Science*, 246:1275–1281 (1989).

To prepare Lambda Hc2, a synthetic DNA sequence containing all of the above features was constructed by designing single stranded polynucleotide segments of 20–40 bases that would hybridize to each other and form the double stranded synthetic DNA sequence shown in FIG. 3. The individual single-stranded polynucleotide segments are shown in Table 3.

Polynucleotides N2, N3, N9-4, N11, N10-5, N6, N7 and N8 (Table 3) were kinased by adding 1 µl of each polynucleotide 0.1 micrograms/microliter (µg/µl) and units of T$_4$ polynucleotide kinase to a solution containing 70 mM Tris-HCl, pH 7.6, 10 mM MgCl$_2$, 5 mM dithiothreitol (DTT), 10 mM beta-mercaptoethanol, 500 micrograms per milliliter (µg/ml) bovine serum albumin (BSA). The solution was maintained at 37 degrees Centigrade (37° C.) for 30 minutes and the reaction stopped by maintaining the solution at 65° C. for 10 minutes. The two end polynucleotides, 20 ng of polynucleotides N1 and polynucleotides N12, were added to the above kinasing reaction solution together with 1/10 volume of a solution containing 20.0 mM Tris-HCl, pH 7.4, 2.0 mM MgCl$_2$ and 50.0 mM NaCl. This solution was heated to 70° C. for 5 minutes and allowed to cool to room temperature, approximately 25° C., over 1.5 hours in a 500 ml beaker of water. During this time period all 10 polynucleotides annealed to form the double stranded synthetic DNA insert shown in FIG. 3. The individual polynucleotides were covalently linked to each other to stabilize the synthetic DNA insert by adding 40 µl of the above reaction to a solution containing 50 mM Tris-HCl, pH 7.5, 7 mM MgCl$_2$, 1 mM DTT, 1 mM adenosine triphosphate (ATP) and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 µl of the above reaction, 4 µl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

TABLE 3

| SEQ. ID. NO. | | |
|---|---|---|
| (22) | N1) | 5' GGCCGCAAATTCTATTTCAAGGAGACAGTCAT 3' |
| (23) | N2) | 5' AATGAAATACCTATTGCCTACGGCAGCCGCTGGATT 3' |
| (24) | N3) | 5' GTTATTACTCGCTGCCCAACCAGCCATGGCCC 3' |
| (25) | N6) | 5' CAGTTTCACCTGGGCCATGGCTGGTTGGG 3' |
| (26) | N7) | 5' CAGCGAGTAATAACAATCCAGCGGCTGCCGTAGGCAATAG 3' |
| (27) | N8) | 5' GTATTTCATTATGACTGTCTCCTTGAAATAGAATTTGC 3' |
| (28) | N9-4) | 5' AGGTGAAACTGCTCGAGATTTCTAGACTAGTTACCCGTAC 3' |
| (29) | N10-5) | 5' CGGAACGTCGTACGGGTAACTAGTCTAGAAATCTCGAG 3' |
| (30) | N11) | 5' GACGTTCCGGACTACGGTTCTTAATAGAATTCG 3' |
| (31) | N12) | 5' TCGACGAATTCTATTAAGAACCGTAGTC 3' |

Figure 4:
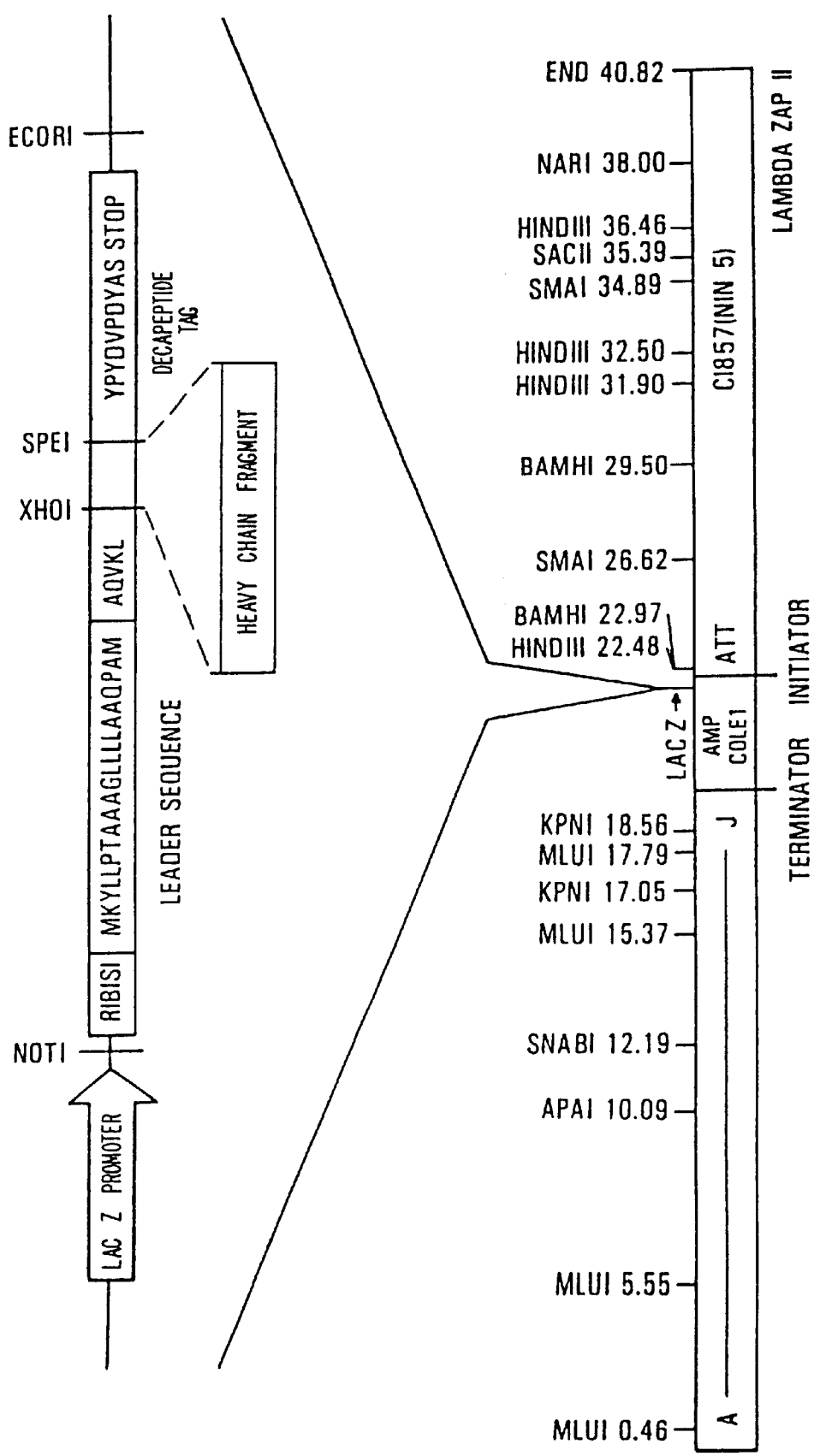
FIG. 4 illustrates the major features of the bacterial expression vector Lambda Hc2 ($V_H$ expression vector). The synthetic DNA sequence from FIG. 3 is shown at the top along with the $T_3$ polymerase promoter from Lambda Zap II. The orientation of the insert in Lambda zap II is shown. The $V_H$ DNA homologs are inserted into the Xho I and spe I cloning sites. The read through transcription produces the decapeptide epitope (tag) that is located just 3' of the cloning site.

The completed synthetic DNA insert was ligated directly into the Lambda Zap™ II vector described in Example 1a (i) that had been previously digested with the restriction enzymes, Not I and Xho I. The ligation mixture was packaged according to the manufacture's instructions using Gigapack II Gold packing extract available from Stratagene, La Jolla, Calif. The packaged ligation mixture was plated on XL1-Blue cells (Stratagene). Individual lambda plaques were cored and the inserts excised according to the in vivo excision protocol for Lambda Zap™ II provided by the manufacturer (Stratagene). This in vivo excision protocol moved the cloned insert from the Lambda Hc2 vector into a phagemid vector to allow easy for manipulation and sequencing. The accuracy of the above cloning steps was confirmed by sequencing the insert using the Sanger dideoxy method described in by Sanger et al., *Proc. Natl. Acad. Sci. USA*, 74:5463–5467, (1977) and using the manufacture's instructions in the AMV Reverse Transcriptase $^{35}$S-ATP sequencing kit (Stratagene). The sequence of the resulting double-stranded synthetic DNA insert in the $V_H$ expression vector (Lambda Hc2) is shown in FIG. 3. The sequence of each strand (top and bottom) of Lambda Hc2 is listed in the sequence listing as SEQ ID NO 1 and SEQ ID NO 2, respectively. The resultant Lambda Hc2 expression vector is shown in FIG. 4.

(iii) Preparation of Lambda Lc2

To express a plurality of $V_L$-coding DNA homologs in an *E. coli* host cell, a vector designated Lambda Lc2 was constructed having the capacity to place the $V_L$-coding DNA homologs in the proper reading frame, provided a ribosome binding site as described by Shine et al., *Nature*, 254:34 (1975), provided the pelB gene leader sequence secretion signal that has been previously used to successfully secrete Fab fragments in *E. coli* by Lei et al., *J. Bac.*, 169:4379 (1987) and Better et al., *Science*, 240:1041 (1988), and also provided a polynucleotide containing a restriction endonuclease site for cloning. Lambda Lc2 has been previously described by Huse et al., *Science*, 246:1275–1281 (1989).

A synthetic DNA sequence containing all of the above features was constructed by designing single stranded polynucleotide segments of 20–60 bases that would hybridize to each other and form the double stranded synthetic DNA sequence shown in FIG. 5. The sequence of each individual single-stranded polynucleotide segment (01-08) within the double stranded synthetic DNA sequence is shown in Table 4.

Polynucleotides 02, 03, 04, 05, 06 and 07 (Table 4) were kinased by adding 1 µl (0.1 ug/µl) of each polynucleotide and 20 units of $T_4$ polynucleotide kinase to a solution containing 70 mM Tris-HCl, pH 7.6, 10 mM MgCl, 5 mM DTT, 10 mM beta-mercaptoethanol, 500 mg/ml of BSA. The solution was maintained at 37° C. for 30 minutes and the reaction stopped by maintaining the solution at 65° C. for 10 minutes. The 20 ng each of the two end polynucleotides, 01 and 08, were added to the above kinasing reaction solution together with 1/10 volume of a solution containing 20.0 mM Tris-HCl, pH 7.4, 2.0 mM MgCl and 15.0 mM sodium chloride (NaCl). This solution was heated to 70° C. for 5 minutes and allowed to cool to room temperature, approximately 25° C., over 1.5 hours in a 500 ml beaker of water. During this time period all 8 polynucleotides annealed to form the double stranded synthetic DNA insert shown in FIG. 5. The individual polynucleotides were covalently linked to each other to stabilize the synthetic DNA insert by adding 40 µl of the above reaction to a solution containing 50 ml Tris-HCl, pH 7.5, 7 ml MgCl, 1 mm DTT, 1 mm ATP and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 µl of the above reaction, 4 µl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

TABLE 4

| SEQ. ID. NO. | | |
|---|---|---|
| (32) | 01) | 5' TGAATTCTAAACTAGTCGCCAAGGAGACAGTCAT 3' |
| (33) | 02) | 5' AATGAAATACCTATTGCCTACGGCAGCCGCTGGATT 3' |
| (34) | 03) | 5' GTTATTACTCGCTGCCCAACCAGCCATGGCC 3' |
| (35) | 04) | 5' GAGCTCGTCAGTTCTAGAGTTAAGCGGCCG 3' |
| (36) | 05) | 5' GTATTTCATTATGACTGTCTCCTTGGCGACTAGTTTAGAA-TTCAAGCT 3' |

TABLE 4-continued

| SEQ. ID. NO. | |
|---|---|
| (37) 06) | 5' CAGCGAGTAATAACAATCCAGCGGCTGCCGTAGGCAATAG 3' |
| (38) 07) | 5' TGACGAGCTCGGCCATGGCTGGTTGGG 3' |
| (39) 08) | 5' TCGACGGCCGCTTAACTCTAGAAC 3' |

The completed synthetic DNA insert was ligated directly into the Lambda Zap™ II vector described in Example 1(a)(i) that had been previously digested with the restriction enzymes Sac I and Xho I. The ligation mixture was packaged according to the manufacture's instructions using Gigapack II Gold packing extract (Stratagene). The packaged ligation mixture was plated on XL1-Blue cells (Stratagene). Individual lambda plaques were cored and the inserts excised according to the in vivo excision protocol for Lambda Zap™ II provided by the manufacturer (Stratagene). This in vivo excision protocol moved the cloned insert from the Lambda Lc2 vector into a plasmid phagemid vector allow for easy manipulation and sequencing. The accuracy of the above cloning steps was confirmed by sequencing the insert using the manufacture's instructions in the AMV Reverse Transcriptase $^{35}$S-dATP sequencing kit (Stratagene). The sequence of the resulting Lc2 expression vector (Lambda Lc2) is shown in FIG. 5. Each strand is separately listed in the Sequence Listing as SEQ ID NO 3 and SEQ ID NO 4. The resultant Lc2 vector is schematically diagrammed in FIG. 6.

A preferred vector for use in this invention, designated Lambda Lc3, is a derivative of Lambda Lc2 prepared above. Lambda Lc2 contains a Spe I restriction site (ACTAGT) located 3' to the EcoR I restriction site and 5' to the Shine-Dalgarno ribosome binding site as shown in the sequence in FIG. 5 and in SEQ ID NO 3. A Spe I restriction site is also present in Lambda Hc2 as shown in FIGS. 3 and 4 and in SEQ ID NO 1. A combinatorial vector, designated pComb, was constructed by combining portions of Lambda Hc2 and Lc2 together as described in Example 1a (iv) below. The resultant combinatorial pComb vector contained two Spe I restriction sites, one provided by Lambda Hc2 and one provided by Lambda Lc2, with an EcoR I site in between. Despite the presence of two Spe I restriction sites, DNA homologs having Spe I and EcoR I cohesive termini were successfully directionally ligated into a pComb expression vector previously digested with Spe I and EcoR I as described in Example 1b below. The proximity of the EcoR I restriction site to the 3' Spe I site, provided by the Lc2 vector, inhibited the complete digestion of the 3' Spe I site. Thus, digesting pComb with Spe I and EcoR I did not result in removal of the EcoR I site between the two Spe I sites.

The presence of a second Spe I restriction site may be undesirable for ligations into a pComb vector digested only with Spe I as the region between the two sites would be eliminated. Therefore, a derivative of Lambda Lc2 lacking the second or 3' Spe I site, designated Lambda Lc3, is produced by first digesting Lambda Lc2 with Spe I to form a linearized vector. The ends are filled in to form blunt ends which are ligated together to result in Lambda Lc3 lacking a Spe I site. Lambda Lc3 is a preferred vector for use in constructing a combinatorial vector as described below.

(iv) Preparation of pComb

Phagemids were excised from the expression vectors Lambda Hc2 or Lambda Lc2 using an in vivo excision protocol described above. Double stranded DNA was prepared from the phagemid-containing cells according to the methods described by Holmes et al., Anal. Biochem., 114:193 (1981). The phagemids resulting from in vivo excision contained the same nucleotide sequences for antibody fragment cloning and expression as did the parent vectors, and are designated phagemid Hc2 and Lc2, corresponding to Lambda Hc2 and Lc2, respectively.

For the construction of combinatorial phagemid vector pcomb, produced by combining portions of phagemid Hc2 and phagemid Lc2, phagemid Hc2 was first digested with Sac I to remove the restriction site is located 5' to the LacZ promoter. The linearized phagemid was then blunt ended with T4 polymerase and ligated to result in a Hc2 phagemid lacking a Sac I site. The modified Hc2 phagemid and the Lc2 phagemid were then separately restriction digested with Sca I and EcoR I to result in a Hc2 fragment having from 5' to 3' Sca I, Not I Xho I, Spe I and EcoR I restriction sites and a Lc2 fragment having from 5' to 3' EcoR I, Sac I, Xba I and Sac I restriction sites. The linearized phagemids were then ligated together at their respective cohesive ends to form pComb, a circularized phagemid having a linear arrangement of restriction sites of Not I, Xho I, Spe I, EcoR I, Sac I, Xba I, Not I, Apa I and Sca I. The ligated phagemid vector was then inserted into an appropriate bacterial host and transformants were selected on the antibiotic ampicillin.

Figure 7:
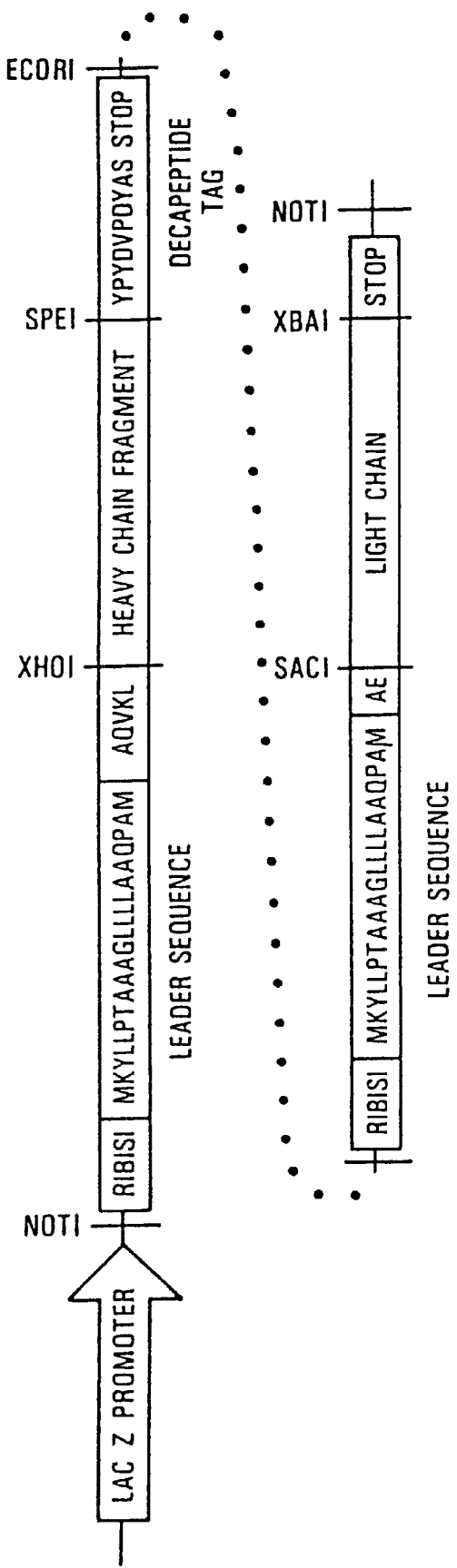
FIG. 7 illustrates the dicistronic expression vector, pComb, in the form of a phagemid expression vector. To produce pComb, phagemids were first excised from the expression vectors, Lambda Hc2 and Lambda Lc2, using an in vivo excision protocol according to manufacturers instructions (Stratagene, La Jolla, Calif.). The pComb expression vector is prepared from Lambda Hc2 and Lambda Lc2 which do not contain $V_H$-coding or $V_L$-coding DNA homologs. The in vivo excision protocol moved the cloned insert from the Lambda Hc2 and Lc2 vectors into a phagemid vector. The resultant phagemids contained the same nucleotide sequences for antibody fragment cloning and expression as did the parent vectors. Hc2 and Lc2 phagemid expression vectors were separately restriction digested with Sca I and EcoR I. The linearized phagemids were ligated via the Sca I and EcoR I cohesive termini to form the dicistronic (combinatorial) vector, pComb.

Selected ampicillin resistant transformants were screened for the presence of two Not I sites. The resulting ampicillin resistant combinatorial phagemid vector was designated pcomb, the schematic organization of which is shown in FIG. 7. The resultant combinatorial vector, pComb, consisted of a DNA molecule having two cassettes to express two fusion proteins and having nucleotide residue sequences for the following operatively linked elements listed in a 5' to 3' direction: a first cassette consisting of an inducible LacZ promoter upstream from the LacZ gene; a Not I restriction site; a ribosome binding site; a pelB leader; a spacer; a cloning region bordered by a 5' Xho and 3' Spe I restriction site.; a decapeptide tag followed by expression control stop sequences; an EcoR I restriction site located 5' to a second cassette consisting of an expression control ribosome binding site; a pelB leader; a spacer region; a cloning region bordered by a 5' Sac I and a 3' Xba I restriction site followed by expression control stop sequences and a second Not I restriction site.

A preferred combinatorial vector for use in this invention, designated pComb2, is constructed by combining portions of phagemid Hc2 and phagemid Lc3 as described above for preparing pComb. The resultant combinatorial vector, pComb2, consists of a DNA molecule having two cassettes identical to pComb to express two fusion proteins identically to pComb except that a second Spe I restriction site in the second cassette is eliminated.

b. Construction of Vectors pCombVIII and pCombIII for Expressing Fusion Proteins Having a Bacteriophage Coat Protein Membrane Anchor Because of the multiple endonuclease restriction cloning sites, the pComb phagemid expression vector prepared above is a useful cloning vehicle for modification for the preparation of an expression vector of this invention. To that end, pcomb is digested with EcoR I and Spe I followed by phosphatase treatment to produce linearized pcomb.

(i) Preparation of pCombVIII

A PCR product produced in Example 2g and having a nucleotide sequence that defines a filamentous bacteriophage coat protein VIII (cpVIII) membrane anchor domain and cohesive Spe I and EcoR I termini was admixed with the linearized pcomb to form a ligation admixture. The cpVIII-membrane anchor-encoding PCR fragment was directionally ligated into the pComb phagemid expression vector at corresponding cohesive termini, that resulted in forming pCombVIII (also designated pComb8). pCombVIII contains a cassette defined by the nucleotide sequence shown in SEQ ID NO 116 from nucleotide base 1 to base 208, and contains a pelB secretion signal operatively linked to the cpVIII membrane anchor.

A preferred phagemid expression vector for use in this invention, designated either pComb2-VIII or pComb2-8, was prepared as described above by directionally ligating the cpVIII membrane anchor-encoding PCR fragment into a pComb2 phagemid expression vector via Spe I and EcoR I cohesive termini. The pComb2-8 had only one Spe I restriction site.

(ii) Preparation of vCombIII

A separate phagemid expression vector was constructed using sequences encoding bacteriophage cpIII membrane anchor domain. A PCR product defining the cpIII membrane anchor containing a LacZ promotor region sequence 3' to the membrane anchor for expression of the light chain and Spe I and EcoR I cohesive termini was prepared as described for cpVIII, the details of which are described in Example 2g. The cpIII-derived PCR product was then ligated into linearized pComb2 vector having only one Spe I site to form the vector pComb2-3 (also designated pComb2-III).

A more preferred phagemid expression vector for use in this invention having additional restriction enzyme cloning sites, designated pComb-III' or pComb2-3', was prepared as described above for pComb2-3 with the addition of a 51 base pair fragment from pBluescript as described by Short et al., Nuc. Acids Res., 16:7583–7600 (1988) and commercially available from Stratagene. To prepare pComb2-3', pComb2-3 was first digested with Xho I and Spe I restriction enzymes to form a linearized pComb2-3. The vector pBluescript was digested with the same enzymes releasing a 51 base pair fragment containing the restriction enzyme sites Sal I, Acc I, Hinc II, Cla I, Hind III, EcoR V, Pst I, Sma I and BamH I. The 51 base pair fragment was ligated into the linearized pComb2-3 vector via the cohesive Xho I and Spe I termini to form pComb2-3'.

c. Construction of pCBAK Vectors Having a Chloramphenicol Resistance Marker

In order to utilize a different selectable marker gene, such as chloramphenicol acetyl transferase (CAT), for the selection of bacteria transformed with a vector of this invention, expression vectors based on pComb were developed having a gene encoding CAT and are designated pCBAK vectors. The pCBAK vectors are prepared by combining portions of pCB and pComb.

(i) Preparation of pCB pBlueScript phagemid vectors, pBC SK(−) and pBS SK(−), (Stratagene), were modified and combined to generate a third vector designated pCB as described below.

pBC SK(−), which contains a chloramphenicol resistance selectable marker gene, was digested with Bst BI and blunt ended with T4 polymerase. A second digestion with Pvu I allowed for the removal of a 1 kilobase (kb) fragment leaving a 2.4 kb linearized vector which retained the CAT selectable resistance marker gene, an inducible LacZ promoter upstream from the LacZ gene and a ColE1 origin region. The 2.4 kb fragment was recovered. The pBS SK(−) vector was digested with Aat II and blunt ended with T4 polymerase. A second digestion with Pvu I allowed for the isolation of an 800 base pair (bp) fragment containing the f1 origin of replication. Ligation of the pBS derived 800 bp f1 fragment with the 2.4 kb pBC fragment created a pCB precursor vector containing a rod Sac I site, an f1 origin of replication, a CAT selectable resistance marker gene, ColE1 origin, a multiple cloning site (MCS) flanked by $T_3$ and $T_7$ promoters, and an inducible LacZ promoter upstream from LacZ gene.

The pCE precursor vector was then digested with Sac I and blunt-ended with T4 polymerase. The T4 polymerase-treated pCB vector was then religated to form pCB vector and is lacking a Sac I site.

(ii) Preparation of pCBAK0

The pCB vector containing the CAT selectable resistance marker gene was digested with Sac II and Apa I and treated with phosphatase to prevent religation and to form linearized pCB vector. The pComb vector prepared in Example 1(a)(iv) was restriction digested with Sac II and Apa I to release a fragment containing nucleotide residue sequences starting 5' to the LacZ promoter and extending past the 3' end of the second Not I site. The Sac II and Apa I pComb DNA fragment was then directionally ligated into the similarly digested pCB vector to form phagemid expression vector pCBAK0. Preferred pCBAK expression vectors are constructed with pComb2. The resultant pCBAK expression vector contained only one Spe I restriction site.

(iii) Preparation of pCBAK8

To prepare a pCBAK-based phagemid expression vector which encodes a bacteriophage coat protein membrane anchor domain in the expressed fusion protein, pCB phagemid cloning vector prepared in Example 1c(ii) was linearized by digestion with Sac II and Apa I. The pCombVIII phagemid expression vector, prepared in Example 1b(i), was restriction digested with Sac II and Apa I to form a fragment containing a nucleotide residue sequence starting 5' to the LacZ promoter and extending past the 3' end of the second Not 1 site. The fragment was directionally ligated into the linearized pCB cloning vector to form phagemid expression vector pCBAK8.

(iv) Preparation of pCBAK3

The phagemid expression vector, pCBAK3, for the expression of fusion protein having cpIII membrane anchor domains, was similarly constructed by directionally ligating the Sac II and Apa I restriction digested fragment from pCombIII with Sac II and Apa I linearized pCB cloning vector.

2. Construction of Dicistronic Expression Vectors for Expressing Anti-NPN Heterodimer on Phage Surfaces In practicing this invention, the heavy (Fd consisting of $V_H$ and $C_H1$) and light (kappa) chains ($V_L$, $C_L$) of antibodies are first targeted to the periplasm of E. coli for the assembly of heterodimeric Fab molecules. In order to obtain expression of antibody Fab libraries on a phage surface, the nucleotide residue sequences encoding either the Fd or light chains must be operatively linked to the nucleotide residue sequence encoding a filamentous bacteriophage coat protein membrane anchor. Two preferred coat proteins for use in this invention in providing a membrane anchor are VIII and III (cpVIII and cpIII, respectively). In the Examples described herein, methods for operatively linking a nucleotide residue sequence encoding a Fd chain to either cpVIII or cpIII membrane anchors in a fusion protein of this invention are described.

In a phagemid vector, a first and second cistron consisting of translatable DNA sequences are operatively linked to form a dicistronic DNA molecule. Each cistron in the dicistronic DNA molecule is linked to DNA expression control sequences for the coordinate expression of a fusion protein, Fd-cpVIII or Fd-cpIII, and a kappa light chain.

The first cistron encodes a periplasmic secretion signal (pelB leader) operatively linked to the fusion protein, either Fd-cpVIII or Fd-cpIII. The second cistron encodes a second pelB leader operatively linked to a kappa light chain. The presence of the pelB leader facilitates the coordinated but separate secretion of both the fusion protein and light chain from the bacterial cytoplasm into the periplasmic space.

The process described above is schematically diagrammed in FIG. 8. Briefly, the phagemid expression vector carries a chloramphenicol acetyl transferase (CAT) selectable resistance marker gene in addition to the Fd-cpVIII fusion and the kappa chain. The f1 phage origin of replication facilitates the generation of single stranded phagemid. The isopropyl thiogalactopyranoside (IPTG) induced expression of a dicistronic message encoding the Fd-cpVIII fusion ($V_H$, $C_H1$, cpVIII) and the light chain ($V_L$, $C_L$) leads to the formation of heavy and light chains. Each chain is delivered to the periplasmic space by the pelB leader sequence, which is subsequently cleaved. The heavy chain is anchored in the membrane by the cpVIII membrane anchor domain while the light chain is secreted into the periplasm. The heavy chain in the presence of light chain assembles to form Fab molecules. This same result can be achieved if, in the alternative, the light chain is anchored in the membrane via a light chain fusion protein having a membrane anchor and heavy chain is secreted via a pelB leader into the periplasm.

With subsequent infection of *E. coli* with a helper phage, as the assembly of the filamentous bacteriophage progresses, the coat protein VIII is incorporated along the entire length of the filamentous phage particles as shown in FIGS. 8 and 9. If cpIII is used, the accumulation occurs on the tail of the bacteriophage. The advantage of the utilization of membrane anchors from cpVIII over cpIII is two fold. Firstly, a multiplicity of binding sites, consisting of approximately 2700 cpVIII monomers assembled in a tubular array, exist along the particle surface. Secondly, the construct does not interfere with phage infectivity.

a. Polynucleotide Selection

The nucleotide sequences encoding the immunoglobulin protein CDR's are highly variable. However, there are several regions of conserved sequences that flank the V region domains of either the light or heavy chain, for instance, and that contain substantially conserved nucleotide sequences, i.e., sequences that will hybridize to the same primer sequence. Therefore, polynucleotide synthesis (amplification) primers that hybridize to the conserved sequences and incorporate restriction sites into the DNA homolog produced that are suitable for operatively linking the synthesized DNA fragments to a vector were constructed. More specifically, the primers are designed so that the resulting DNA homologs produced can be inserted into an expression vector of this invention in reading frame with the upstream translatable DNA sequence at the region of the vector containing the directional ligation means.

(i) $V_H$ Primers

For amplification of the $V_H$ domains, primers are designed to introduce cohesive termini compatible with directional ligation into the unique Xho I and Spe I sites of the phagemid Hc2 expression vector. For example, the 3' primer (primer 12A in Table 5), was designed to be complementary to the mRNA in the $J_H$ region. In all cases, the 5' primers (primers 1–10, Table 5) were chosen to be complementary to the first strand cDNA in the conserved N-terminus region (antisense strand) Initially amplification was performed with a mixture of 32 primers (primer 1, Table 5) that were degenerate at five positions. Hybridoma mRNA could be amplified with mixed primers, but initial attempts to amplify mRNA from spleen yielded variable results. Therefore, several alternatives to amplification using the mixed 5' primers were compared.

The first alternative was to construct multiple unique primers, eight of which are shown in Table 5, corresponding to individual members of the mixed primer pool. The individual primers 2–9 of Table 5 were constructed by incorporating either of the two possible nucleotides at three of the five degenerate positions.

The second alternative was to construct a primer containing inosine (primer 10, Table 5) at four of the variable positions based on the published work of Takahashi, et al., *Proc. Natl. Acad. Sci. (USA)*, 82:1931–1935, (1985) and Ohtsuka et al., *J. Biol. Chem.*, 260: 2605–2608, (1985). This primer has the advantage that it is not degenerate and, at the same time minimizes the negative effects of mismatches at the unconserved positions as discussed by Martin et al., *Nuc. Acids Res.*, 13:8927 (1985). However, it was not known if the presence of inosine nucleotides would result in incorporation of unwanted sequences in the cloned $V_H$ regions. Therefore, inosine was not included at the one position that remains in the amplified fragments after the cleavage of the restriction sites. As a result, inosine was not in the cloned insert.

Additional $V_H$ amplification primers including the unique 3' primer were designed to be complementary to a portion of the first constant region domain of the gamma 1 heavy chain mRNA (primers 16 and 17, Table 5). These primers will produce DNA homologs containing polynucleotides coding for amino acids from the $V_H$ and the first constant region domains of the heavy chain. These DNA homologs can therefore be used to produce Fab fragments rather than $F_V$.

Additional unique 3' primers designed to hybridize to similar regions of another class of immunoglobulin heavy chain such as IgM, IgE and IgA are contemplated. Other 3' primers that hybridize to a specific region of a specific class of $CH_1$ constant region and are adapted for transferring the $V_H$ domains amplified using this primer to an expression vector capable of expressing those $V_H$ domains with a different class of heavy or light chain constant region are also contemplated.

As a control for amplification from spleen or hybridoma mRNA, a set of primers hybridizing to a highly conserved region within the constant region IgG, heavy chain gene were constructed. The 5' primer (primer 11, Table 5) is complementary to the cDNA in the $C_H2$ region whereas the 3' primer (primer 13, Table 5) is complementary to the mRNA in the $C_H3$ region. It is believed that no mismatches were present between these primers and their templates.

The primers used for amplification of heavy chain Fd fragments for construction of Fabs are shown at least in Table 5. Amplification was performed in eight separate reactions, each containing one of the 5' primers (primers 2–9) and one of the 3' primers (primer 16). The remaining 5' primers that have been used for amplification in a single reaction are either a degenerate primer (primer 1) or a primer that incorporates inosine at four degenerate positions (primer 10, Table 5, and primers 17 and 18, Table 6). The remaining 3' primer (primer 14, Table 6) has been used to construct $F_V$ fragments. Many of the 5' primers incorporate a Xho I site, and the 3' primers incorporate a Spe I restriction site for insertion of the $V_H$ DNA homolog into the phagemid Hc2 expression vector (FIG. 4).

$V_H$ amplification primers designed to amplify human heavy chain variable regions are shown in Table 6. One of the 5' heavy chain primer contains inosine residues at degenerate nucleotide positions allowing a single primer to hybridize to a large number of variable region sequences. Primers designed to hybridize to the constant region sequences of various IgG mRNAs are also shown in Table 6.

(ii) $V_L$ Primers

The nucleotide sequences encoding the $V_L$ CDRs are highly variable. However, there are several regions of conserved sequences that flank the $V_L$ CDR domains including the $J_L$, $V_L$ framework regions and $V_L$ leader/promotor. Therefore, amplification primers were constructed that hybridized to the conserved sequences and incorporate restriction sites that allow cloning the amplified fragments into the phagemid Lc2 vector cut with Sac I and Xba I.

Figure 6:
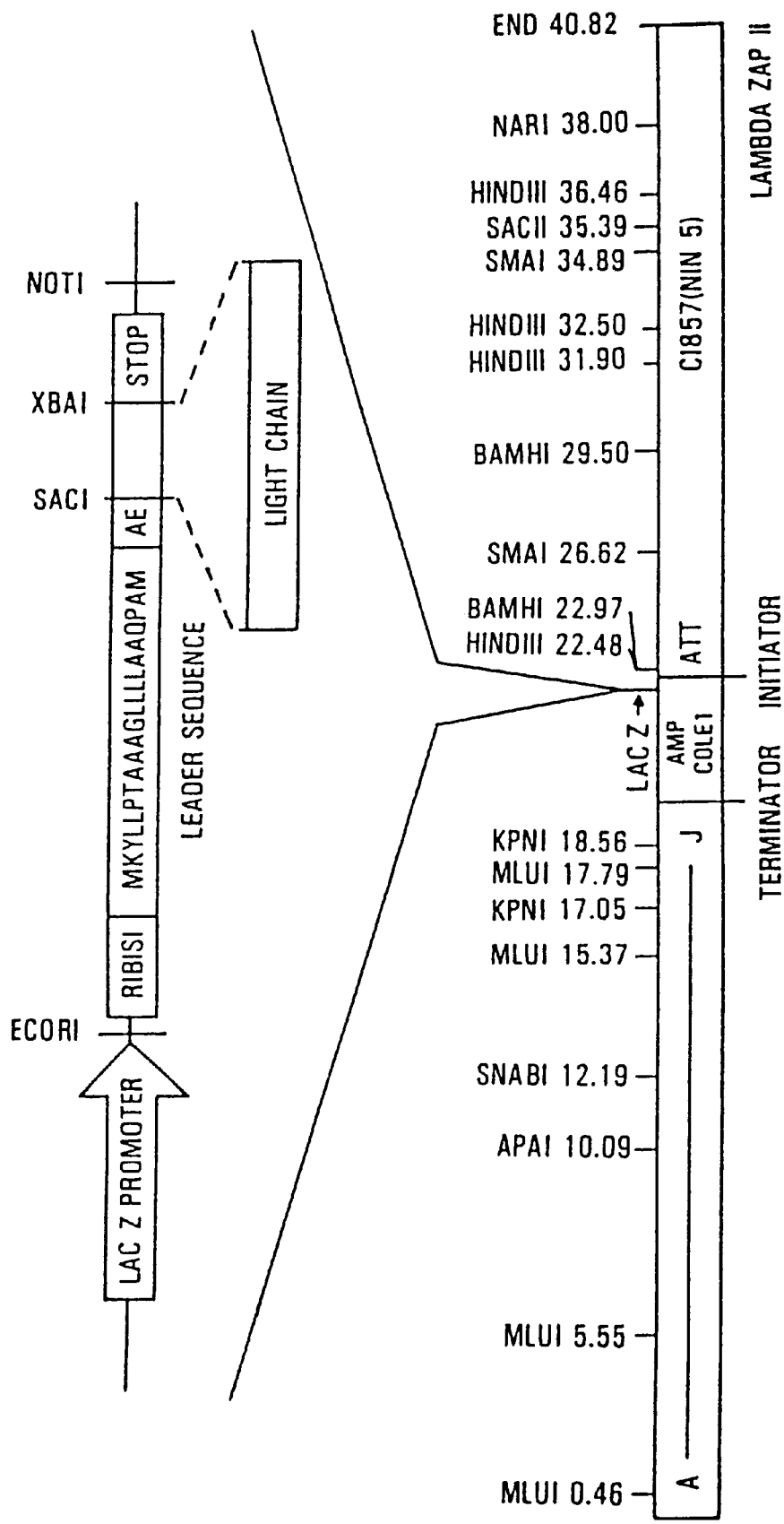
FIG. 6 illustrates the major features of the bacterial expression vector Lc2 ($V_L$ expression vector). The synthetic DNA sequence from FIG. 5 is shown at the top along with the $T_3$ polymerase promoter from Lambda Zap II. The orientation of the insert in Lambda Zap II is shown. The $V_L$ DNA homologs are inserted into the Sac I and Xho I cloning sites.

For amplification of the $V_L$ CDR domains, the 5' primers (primers 1–8 in Table 6) were designed to be complementary to the first strand cDNA in the conserved N-terminus region. These primers also introduced a Sac I restriction endonuclease site to allow the $V_L$ DNA homolog to be cloned into the phagemid Lc2 expression vector. The 3' $V_L$ amplification primer (primer 9 in Table 6) was designed to be complementary to the mRNA in the $J_L$ regions and to introduce the Xba I restriction endonuclease site required to insert the $V_L$ DNA homolog into the phagemid Lc2 expression vector (FIG. 6).

Additional 3' $V_L$ amplification primers were designed to hybridize to the constant region of either kappa or lambda mRNA (primers 10 and 11 in Table 6). These primers allow a DNA homolog to be produced containing polynucleotide sequences coding for constant region amino acids of either kappa or lambda chain. These primers make it possible to produce an Fab fragment rather than an $F_V$.

The primers used for amplification of kappa light chain sequences for construction of Fabs are shown at least in Table 6. Amplification with these primers was performed in 5 separate reactions, each containing one of the 5' primers (primers-3–6, and 12) and one of the 3' primers (primer 13). The remaining 3' primer (primer 9) has been used to construct $F_V$ fragments. The 5' primers contain a Sac I restriction site and the 3' primers contain a Xba I restriction site.

$V_L$ amplification primers designed to amplify human light chain variable regions of both the lambda and kappa isotypes are also shown in Table 6.

All primers and synthetic polynucleotides described herein, including those shown in Tables 3–7 were either purchased from Research Genetics in Huntsville, Alabama or synthesized on an Applied Biosystems DNA synthesizer, model 381A, using the manufacturer's instruction.

TABLE 5

| | | |
|---|---|---|
| (1) | 5'AGGT(C/G)(C/A)A(G/A)CT(G/T)CTCGAGTC(T/A)GG 3' | degenerate 5' primer for the amplification of mouse and human heavy chain variable regions ($V_H$) |
| (2) | 5'AGGTCCAGCTGCTCGAGTCTGG 3' | Unique 5' primer for the amplification of mouse and human $V_H$ |
| (3) | 5'AGGTCCAGCTGCTCGAGTCAGG 3' | Unique 5' primer for the amplification of mouse and human $V_H$ |
| (4) | 5'AGGTCCAGCTTCTCGAGTCTGG 3' | Unique 5' primer for the amplification of mouse and human $V_H$ |
| (5) | 5'AGGTCCAGCTTCTCGAGTCAGG 3' | Unique 5' primer for the amplification of mouse and human $V_H$ |
| (6) | 5'AGGTCCAACTGCTCGAGTCTGG 3' | Unique 5' primer for the amplification of mouse and human $V_H$ |
| (7) | 5'AGGTCCAACTGCTCGAGTCAGG 3' | Unique 5' primer for the amplification of mouse and human $V_H$ |
| (8) | 5'AGGTCCAACTTCTCGAGTCTGG 3' | Unique 5' primer for the amplification of mouse and human $V_H$ |
| (9) | 5'AGGTCCAACTTCTCGAGTCAGG 3' | Unique 5' primer for the amplification of mouse and human $V_H$ |
| (10) | | 5' degenerate primer containing inosine at 4 degenerate positions for amplification of mouse $V_H$ |
| (11) | 5'GCCCAAGGATGTGCTCACC 3' | 5' primer for amplification in the $C_H2$ region of mouse IgGl |
| (12) | 5'CTATTAGAATTCAACGGTAACAGTGGTGCCTTGGCCCCA 3' | 3' primer for amplification of $V_H$ and introducing a 3' Eco RI site |
| (12A) | 5'CTATTAACTAGTAACGGTAACAGTGGTGCCTTGGCCCCA 3' | 3' primer for amplification of $V_H$ using 3' Spe I site |
| (13) | 5'CTCAGTATGGTGGTTGTGC 3' | 3' primer for amplification in the $C_H3$ region of mouse IgGl |
| (14) | 5'GCTACTAGTTTTGATTTCCACCTTGG 3' | 3' primer for amplification of mouse kappa light chain variable regions ($V_L$) |
| (15) | 5'CAGCCATGGCCGACATCCAGATG 3' | 5' primer for amplification of mouse kappa light chain variable regions |
| (16) | 5'AATTTTACTAGTCACCTTGGTGCTGCTGGC 3' | Unique 3' primer for amplification of $V_H$ including part of the mouse gamma 1 first constant region |
| (17) | 5'TATGCAACTAGTACAACCACAATCCCTGGGCACAATTTT 3' | Unique 3' primer for amplification of Fd including part of mouse IgGl first constant region and hinge region |

TABLE 5-continued

| | |
|---|---|
| (18) 5'AGGCTTACTAGTACAATCCCTGGGCACAAT 3' | 3' primer for amplifying mouse Fd including part of the mouse IgG first constant region and part of the hinge region |

TABLE 6

| | |
|---|---|
| (1) 5' CCAGTTCCGAGCTCGTTGTGACTCAGGAATCT 3' | Unique 5' primer for the amplification of kappa light chain variable regions |
| (2) 5' CCAGTTCCGAGCTCGTGTTGACGCAGCCGCCC 3' | Unique 5' primer for the amplification of kappa light chain variable regions |
| (3) 5' CCAGTTCCGAGCTCGTGCTCACCCAGTCTCCA 3' | Unique 5' primer for the amplification of kappa light chain variable regions |
| (4) 5' CCAGTTCCGAGCTCCAGATGACCCAGTCTCCA 3' | Unique 5' primer for the amplification of kappa light chain variable regions |
| (5) 5' CCAGATGTGAGCTCGTGATGACCCAGACTCCA 3' | Unique 5' primer for the amplification of kappa light chain variable regions |
| (6) 5' CCAGATGTGAGCTCGTCATGACCCAGTCTCCA 3' | Unique 5' primer for the amplification of kappa light chain variable regions |
| (7) 5' CCAGATGTGAGCTCTTGATGACCCAAACTCAA 3' | Unique 5' primer for the amplification of kappa light chain variable regions |
| (8) 5' CCAGATGTGAGCTCGTGATAACCCAGGATGAA 3' | Unique 5' primer for the amplification of kappa light chain variable regions |
| (9) 5' GCAGCATTCTAGAGTTTCAGCTCCAGCTTGCC 3' | Unique 3' primer for amplification of kappa light chain variable regions |
| (10) 5' CCGCCGTCTAGAACACTCATTCCTGTTGAAGCT 3' | Unique 3' primer for mouse kappa light chain amplification including the constant region |
| (11) 5' CCGCCGTCTAGAACATTCTGCAGGAGACAGACT 3' | Unique 3' primer for mouse lambda light chain amplification including the constant region |
| (12) 5' CCAGTTCCGAGCTCGTGATGACACAGTCTCCA 3' | Unique 5' primer for $V_L$ amplification |
| (13) 5' GCGCCGTCTAGAATTAACACTCATTCCTGTTGAA 3' | Unique 3' primer for amplification of kappa light chain |
| (14) 5' CTATTAACTAGTAACGGTAACAGTGGTGCCTTGCCCCA 3' | Unique 3' primer for amplification of mouse $F_V$ |
| (15) 5' AGGCTTACTAGTACAATCCCTGGGCACAAT 3' | Unique 3' primer for amplification of mouse IgG Fd |
| (16) 5' GCCGCTCTAGAACACTCATTCCTGTTGAA 3' | Unique 3' primer for amplification of mouse kappa light chain |
| (17) 5' AGGTIIAICTICTCGAGTCTGC 3' | Degenerate 5' primer containing inosine at 4 degenerate positions for amplifying mouse $V_H$ |
| (18) 5' AGGTIIAICTICTCGAGTCAGC 3' | Degenerate 5' primer containing inosine at 4 degenerate positions for amplifying mouse $V_H$ |
| (19) 5' GTGCCAGATGTGAGCTCGTGATGACCCAGTCTCCA 3' | Unique 5' primer for human and mouse kappa $V_L$ amplification |
| (20) 5' TCCTTCTAGATTACTAACACTCTCCCCTGTTGAA 3' | Unique 3' primer for kappa $V_L$ amplification |
| (21) 5' GCATTCTAGACTATTATGAACATTCTGTAGGGGC 3' | Unique 3' primer for human, mouse and rabbit lambda $V_L$ amplification |
| (22) 5' CTGCACAGGGTCCTGGGCCGAGCTCGTGGTGACTCAG 3' | Unique 5' primer for human lambda $V_L$ amplification |
| (23) 5' AGITGCAIITGCTCGAGTCTGG 3' | 5' degenerate primer for human $V_H$ amplification containing inosine at 3 degenerate positions |
| (24) 5' GTGGGCATGTGTGAGTTGTGTCACTAGTTGGGGTTTTGAGCTC 3' | Unique 3' primer for human $V_H$ amplification |
| (25) 5' AGCATCACTAGTACAAGATTTGGGCTC 3' | Unique 3' primer for human IgG1 Fd amplification |
| (26) 5' AGGTGCAGCTGCTCGAGTCTGG 3' | Unique 5' primers for amplification of human variable regions ($V_H$) |
| (27) 5' AGGTGCAGCTGCTCGAGTCGGG 3' | Unique 5' primers for amplification of human variable regions ($V_H$) |
| (28) 5' AGGTGCAACTGCTCGAGTCTGG 3' | Unique 5' primers for amplification of human variable regions ($V_H$) |
| (29) 5' AGGTGCAACTGCTCGAGTCGGG 3' | Unique 5' primers for amplification of human variable regions ($V_H$) |
| (30) 5' TCCTTCTAGATTACTAACACTCTCCCCTGTTGAA 3' | 3' primer in human kappa light chain constant region |
| (31) 5' CTGCACAGGGTCCTGGGCCGAGCTCGTGGTGACTCAG 3' | 5' primer for amplification of human lambda light chain variable regions |
| (32) 5' GCATTCTAGACTATTAACATTCTGTAGGGGC 3' | 3' primer in human lambda light chain constant region |

TABLE 6-continued

| | |
|---|---|
| (33) 5' ACCCAAGGACACCCTCATG 3' | Control primer hybridizing to the human $CH_2$ region |
| (34) 5' CTCAGTATGGTGGTTGTGC 3' | Control primer hybridizing to the human $CH_3$ region |
| (35) 5' GTCTCACTAGTCTCCACCAAGGGCCCATCGGTC 3' | 5' primer for amplifying human IgG heavy chain first constant region |
| (36) 5' ATATACTAGTGAGACAGTGACCAGGGTTCCTTGGCCCCA 3' | 3' primer for amplifying human heavy chain variable regions |
| (37) 5' ACGTCTAGATTCCACCTTGGTCCC 3' | 3' primer for amplifying human kappa chain variable regions |
| (38) 5' GCATACTAGTCTATTAACATTCTGTAGGGGC 3' | 5' primer for amplifying human kappa light chain constant region |
| (39) 5' CCGGAATTCTTATCATTTACCCGGAGA 3' | 3' primer located in the CH3 region of human IgGl to amplify the entire heavy chain |
| (40) 5' TCTGCACTAGTTGGAATGGGCACATGCAG 3' | 3' primer for amplifying the Fd region of mouse IgM |

The 19 primers listed in Table 5 have been listed in the Sequence Listing and have been assigned the following SEQ ID NO:

(1)=SEQ ID NO 40
(2)=SEQ ID NO 41
(3)=SEQ ID NO 42
(4)=SEQ ID NO 43
(5)=SEQ ID NO 44
(6)=SEQ ID NO 45
(7)=SEQ ID NO 46
(8)=SEQ ID NO 47
(9)=SEQ ID NO 48
(10)=SEQ ID NO 49
(11)=SEQ ID NO 50
(12)=SEQ ID NO 51
(12A)=SEQ ID NO 52
(13)=SEQ ID NO 53
(14)=SEQ ID NO 54
(15)=SEQ ID NO 55
(16)=SEQ ID NO 56
(17)=SEQ ID NO 57
(18)=SEQ ID NO 58

The 40 primers listed as "1(1)" through "(40)" in Table 6 have also been individually and sequentially listed in the Sequence Listing beginning with SEQ ID NO 59 through SEQ ID NO 98, respectively.

b. Preparation of a Repertoire of Genes Encoding Immunoglobulin Variable Domain

Nitrophenylphosphonamidate (NPN) was selected as the ligand for receptor binding in preparing a heterodimeric receptor according to the methods of the invention.

Keyhole limpet hemocyanin (KLH) was conjugated to NPN to form a NPN-KLH conjugate used for immunizing a mouse to produce an anti-NPN immune response and thereby provide a source of ligand specific heterodimeric receptor genes.

The NPN-KLH conjugate was prepared by admixing 250 µl of a solution containing 2.5 mg of NPN in dimethylformamide with 750 µl of a solution containing 2 mg of KLH in 0.01 Molar (M) sodium phosphate buffer (pH 7.2). The two solutions were admixed by slow addition of the NPN solution to the KLH solution while the KLH solution was being agitated by a rotating stirring bar. Thereafter the admixture was maintained at 4° C. for 1 hour with the same agitation to allow conjugation to proceed. The conjugated NPN-KLH was isolated from the nonconjugated NPN and KLH by gel filtration through Sephadex G-25. The isolated NPN-KLH conjugate was injected into mice as described below.

The NPN-KLH conjugate was prepared for injection into mice by adding 100 µg of the conjugate to 250 µl of phosphate buffered saline (PBS). An equal volume of complete Freund's adjuvant was added and emulsified the entire solution for 5 minutes. A 129 $G_{IX+}$ mouse was injected with 300 µl of the emulsion. Injections were given subcutaneously at several sites using a 21 gauge needle. A second immunization with NPN-KLH was given two weeks later. This injection was prepared as follows: 50 micrograms (µg) of NPN-KLH were diluted in 250 µl of PBS and an equal volume of alum was admixed to the NPN-KLH solution. The mouse was injected intraperitoneally with 500 µl of the solution using a 23 gauge needle. One month later the mice were given a final injection of 50 µg of the NPN-KLH conjugate diluted to 200 µl in PBS. This injection was given intravenously in the lateral tail vein using a 30 gauge needle. Five days after this final injection the mice were sacrificed and total cellular RNA was isolated from their spleens.

Total cellular RNA was prepared from the spleen of a single mouse immunized with KLH-NPN as described above using the RNA preparation methods described by Chomczynski et al., Anal Biochem., 162:156–159 (1987) and using the RNA isolation kit (Stratagene) according to the manufacturer's instructions. Briefly, immediately after removing the spleen from the immunized mouse, the tissue was homogenized in 10 ml of a denaturing solution containing 4.0 M guanine isothiocyanate, 0.25 M sodium citrate at pH 7.0, and 0.1 M beta-mercaptoethanol using a glass homogenizer. One ml of sodium acetate at a concentration of 2 M at pH 4.0 was admixed with the homogenized spleen. One ml of phenol that had been previously saturated with $H_2O$ was also admixed to the denaturing solution containing the homogenized spleen. Two ml of a chloroform:isoamyl alcohol (24:1 v/v) mixture was added to this homogenate. The homogenate was mixed vigorously for ten seconds and maintained on ice for 15 minutes. The homogenate was then transferred to a thick-walled 50 ml polypropylene centrifuged tube (Fisher Scientific Company, Pittsburg, Pa.). The solution was centrifuged at 10,000×g for 20 minutes at 4° C. The upper RNA-containing aqueous layer was transferred to a fresh 50 ml polypropylene centrifuge tube and mixed with an equal volume of isopropyl alcohol. This solution was maintained at −20° C. for at least one hour to precipitate the RNA. The solution containing the precipitated RNA was centrifuged at 10,000×g for twenty minutes at 4° C. The pelleted total cellular RNA was collected and dissolved in 3 ml of the denaturing solution described above. Three ml of isopropyl alcohol was added to the re-suspended total cellular RNA and vigorously mixed. This solution was maintained at −20° C. for at least 1 hour to precipitate the RNA. The solution containing the precipitated RNA was centrifuged at 10,000×g for ten minutes at 4° C. The pelleted RNA was washed once with a solution containing 75% ethanol. The pelleted RNA was dried under vacuum for 15 minutes and then re-suspended in dimethyl pyrocarbonate (DEPC) treated (DEPC-$H_2O$) $H_2O$.

Messenger RNA (mRNA) enriched for sequences containing long poly A tracts was prepared from the total cellular RNA using methods described in *Molecular Cloning: A Laboratory Manual*, Maniatis et al., eds., Cold Spring Harbor, N.Y., (1982). Briefly, one half of the total RNA isolated from a single immunized mouse spleen prepared as described above was resuspended in one ml of DEPC-$H_2O$ and maintained at 65° C. for five minutes. One ml of 2×high salt loading buffer consisting of 100 mM Tris-HCl (Tris [hydroxymethyl] aminomethane hydrochloride), 1 M sodium chloride (NaCl), 2.0 mM disodium ethylene diamine tetraacetic acid (EDTA) at pH 7.5, and 0.2% sodium dodecyl sulfate (SDS) was added to the re-suspended RNA and the mixture allowed to cool to room temperature. The mixture was then applied to an oligo-dT (Collaborative Research Type 2 or Type 3) column that was previously prepared by washing the oligo-dT with a solution containing 0.1 M sodium hydroxide and 5 mM EDTA and then equilibrating the column with DEPC-$H_2O$. The eluate was collected in a sterile polypropylene tube and reapplied to the same column after heating the eluate for 5 minutes at 65° C. The oligo-dT column was then washed with 2 ml of high salt loading buffer consisting of 50 mM Tris-HCl, pH 7.5, 500 mM sodium chloride, 1 mM EDTA at pH 7.5 and 0.1% SDS. The oligo dT column was then washed with 2 ml of 1×medium salt buffer consisting of 50 mM Tris-HCl, pH 7.5, 100 mM, 1 mM EDTA and 0.1% SDS. The messenger RNA was eluted from the oligo-dT column with 1 ml of buffer consisting of 10 mM Tris-HCl, pH 7.5, 1 mM EDTA, at pH 7.5, and 0.05% SDS. The messenger RNA was purified by extracting this solution with phenol/chloroform followed by a single extraction with 100% chloroform. The messenger RNA was concentrated by ethanol precipitation and resuspended in DEPC $H_2O$.

The messenger RNA (mRNA) isolated by the above process contains a plurality of different $V_H$ coding polynucleotides, i.e., greater than about $10^4$ different $V_H$-coding genes, and contains a similar number of $V_L$-coding genes. Thus, the mRNA population represents a repertoire of variable region-coding genes.

C. Preparation of DNA Homologs

In preparation for PCR amplification, mRNA prepared above is used as a template for cDNA synthesis by a primer extension reaction. In a typical 50 μl transcription reaction, 5–10 μg of spleen mRNA in water is first hybridized (annealed) with 500 ng (50.0 pmol.) of the 3' $V_H$ primer (primer 12A, Table 5), at 65° C. for five minutes. Subsequently, the mixture is adjusted to 1.5 mM DATP, dCTP, dGTP and dTTP, 40 mM Tris-HCl, pH 8.0, 8 mM $MgCl_2$, 50 mM NaCl, and 2 mM spermidine. Moloney-Murine Leukemia virus Reverse transcriptase (Stratagene), 26 units, is added and the solution is maintained for 1 hour at 37° C.

PCR amplification is performed in a 100 μl reaction containing the products of the reverse transcription reaction (approximately 5 ug of the cDNA/RNA hybrid), 300 ng of 3' $V_H$ primer (primer 12A of Table 5), 300 ng each of the 5' $V_H$ primers (primers 2–10 of Table 5) 200 mM of a mixture of dNTP's, 50 mM KCl, 10 mM Tris-HCl pH 8.3, 15 mM $MgCl_2$, 0.1% gelatin and 2 units of *Thermus acuaticus* (Taq) DNA polymerase (Perkin-Elmer-Cetus, Emeryville, Calif.). The reaction mixture is overlaid with mineral oil and subjected to 40 cycles of amplification. Each amplification cycle includes denaturation at 92° C. for 1 minute, annealing at 52° C. for 2 minutes and polynucleotide synthesis by primer extension (elongation) at 72° C. for 1.5 minutes. The amplified $V_H$-coding DNA homolog containing samples are then extracted twice with phenol/chloroform, once with chloroform, ethanol precipitated and are stored at −70° C. in 10 mM Tris-HCl, pH 7.5, and 1 mM EDTA.

Using unique 5' primers (2–9, Table 5), efficient $V_H$-coding DNA homolog synthesis and amplification from the spleen mRNA is achieved as shown by agarose gel electrophoresis. The amplified cDNA ($V_H$-coding DNA homolog) was seen as a major band of the expected size (360 bp). The amount the amplified $V_H$-coding polynucleotide fragment in each reaction is similar, indicating that all of these primers were about equally efficient in initiating amplification. The yield and quality of the amplification with these primers is reproducible.

The primer containing inosine also synthesizes amplified $V_H$-coding DNA homologs from spleen mRNA reproducibly, leading to the production of the expected sized fragment, of an intensity similar to that of the other amplified cDNAs. The presence of inosine also permits efficient DNA homolog synthesis and amplification, clearly indicating that such primers are useful in generating a plurality of $V_H$-coding DNA homologs. Amplification products obtained from the constant region primers (primers 11 and 13, Table 5) are more intense indicating that amplification was more efficient, possibly because of a higher degree of homology between the template and primers. Following the above procedures, a $V_H$-coding gene library is constructed from the products of eight amplifications, each performed with a different 5' primer. Equal portions of the products from each primer extension reaction are mixed and the mixed product is then used to generate a library of $V_H$-coding DNA homolog-containing vectors.

DNA homologs of the $V_L$ are also prepared from the purified mRNA prepared as described above. In preparation for PCR amplification, mRNA prepared according to the above examples is used as a template for cDNA synthesis. In a typical 50 μl transcription reaction, 5–10 μg of spleen mRNA in water is first annealed with 300 ng (50.0 pmol) of the 3' $V_L$ primer (primer 14, Table 5), at 65° C. for five minutes. Subsequently, the mixture is adjusted to 1.5 mM dATP, dCTP, dGTP, and dTTP, 40 mM Tris-HCl, pH 8.0, 8 mM $MgCl_2$, 50 mM NaCl, and 2 mM spermidine. Moloney-Murine Leukemia virus reverse transcriptase (Stratagene), 26 units, is added and the solution is maintained for 1 hour at 37° C. The PCR amplification is performed in a 100 μl reaction containing approximately 5 μg of the cDNA/RNA hybrid produced as described above, 300 ng of the 3' $V_L$ primer (primer 14 of Table 5), 300 ng of the 5' $V_L$ primer (primer 16 of Table 5), 200 mM of a mixture of dNTP's, 50 mM KCl, 10 mM Tris-HCl pH 8.3, 15 MM $MgCl_2$, 0.1% gelatin and 2 units of Taq DNA polymerase. The reaction mixture is overlaid with mineral oil and subjected to 40 cycles of amplification. Each amplification cycle includes denaturation at 92° C. for 1 minute, annealing at 52° C. for 2 minutes and elongation at 72° C. for 1.5 minutes. The amplified samples are then extracted twice with phenol/chloroform, once with chloroform, ethanol precipitated and are stored at −70° C. in 10 mM Tris-HCl, 7.5 and 1 mM EDTA.

d. Insertion of DNA Homologs into a DNA Expression Vector

To prepare an expression library enriched in $V_H$ sequences, DNA homologs enriched in $V_H$ sequences are prepared according to Example 2c using the same set of 5' primers but with primer 12A (Table 5) as the 3' primer. The resulting PCR amplified products (2.5 µg/30 µl of 150 mM NaCl, 8 mM Tris-HCl, pH 7.5, 6 mM MgSO$_4$, 1 mM DTT, 200 µg/ml BSA) are digested at 37° C. with restriction enzymes Xho I (125 units) and Spe I (125 units). In cloning experiments which required a mixture of the products of the amplification reactions, equal volumes (50 µl, 1–10 µg concentration) of each reaction mixture are combined after amplification but before restriction digestion. The $V_H$ homologs are purified on a 1% agarose gel using the standard electroelution technique described in *Molecular Cloning A Laboratory Manual*, Maniatis et al., eds., Cold Spring Harbor, N.Y., (1982). After gel electrophoresis of the digested PCR amplified spleen mRNA, the region of the gel containing DNA fragments of approximate 350 bp is excised, electroeluted into a dialysis membrane, ethanol precipitated and resuspended in a TE solution containing 10 mM Tris-HCl, pH 7.5 and 1 mM EDTA to a final concentration of 50 ng/µl. The resulting $V_H$ DNA homologs represent a repertoire of polypeptide genes having cohesive termini adapted for directional ligation to the vector Lambda Hc2. These prepared $V_H$ DNA homologs are then directly inserted by directional ligation into linearized Lambda Hc2 expression vector prepared as described below.

The Lambda Hc2 expression DNA vector is prepared for inserting a DNA homolog by admixing 100 µg of this DNA to a solution containing 250 units each of the restriction endonucleases Xho I and Spe I (both from Boehringer Mannheim, Indianapolis, Ind.) and a buffer recommended by the manufacturer. This solution is maintained at 37 from 1.5 hours. The solution is heated at 65° C. for 15 minutes top inactivate the restriction endonucleases. The solution is chilled to 30° C. and 25 units of heat-killable (HK) phosphatase (Epicenter, Madison, Wis.) and CaCl$_2$ is admixed to it according to the manufacturer's specifications. This solution is maintained at 30° C. for 1 hour. The DNA is purified by extracting the solution with a mixture of phenol and chloroform followed by ethanol precipitation. The Lambda Hc2 expression vector is now ready for ligation to the $V_H$ DNA homologs prepared in the above examples. These prepared $V_H$ DNA homologs are then directly inserted into the Xho I and Spe I restriction digested Lambda Hc2 expression vector that prepared above by ligating 3 moles of $V_H$ DNA homolog inserts with each mole of the Hc2 expression vector overnight at 5° C. Approximately 3.0×10$^5$ plague forming units are obtained after packaging the DNA with Gigapack II Bold (Stratagene) of which 50% are recombinants. The ligation mixture containing the $V_H$ DNA homologs are packaged according to the manufacturers specifications using Gigapack Gold II Packing Extract (Stratagene). The resulting Lambda Hc2 expression libraries are then transformed into XL1-Blue cells.

To prepare a library enriched in $V_L$ sequences, PCR amplified products enriched in $V_L$ sequences are prepared according to Example 2c. These $V_L$ DNA homologs are digested with restriction enzymes Sac I and Xba I and the digested $V_L$ DNA homologs are purified on a 1% agarose gel as described above for the $V_H$ DNA homologs' to form a repertoire of $V_L$-polypeptide genes adapted for directional ligation. The prepared $V_L$ DNA homologs are then directionally ligated into the Lambda Lc2 expression vector previously digested with the restriction enzymes, Sac I and Xba I as described for Lambda Hc2. The ligation mixture containing the $V_L$ DNA homologs is packaged to form a Lambda Lc2 expression library as described above and is ready to be plated on XL1-Blue cells.

e. Randomly Combining $V_H$ and $V_L$ DNA Homologs on the Same Expression Vector The construction of a library containing vectors for expressing two cistrons that express heavy and light chains is accomplished in two steps. In the first step, separate heavy and light chain libraries are constructed in the expression vectors Lambda Hc2 and Lambda Lc2, respectively, as described using gene repertoires obtained from a mouse immunized with NPN-KLH. In the second step, these two libraries are combined at the antisymmetric EcoR I sites present in each vector. This resulted in a library of clones each of which potentially co-expresses a heavy and a light chain. The actual combinations are random and do not necessarily reflect the combinations present in the B-cell population in the parent animal.

The spleen mRNA resulting from the above immunizations (Example 2b) is isolated and used to create a primary library of $V_H$ gene sequences using the Lambda Hc2 expression vector. The primary library contains 1.3×10$^6$ plaque-forming units (pfu) and can be screened for the expression of the decapeptide tag to determine the percentage of clones expressing $V_H$ and $C_H1$ (Fd) sequences. The sequence for this peptide is only in frame for expression following the cloning of a Fd (or $V_H$) fragment into the vector. At least 80% of the clones in the library express Fd fragments based on immunodetection of the decapeptide tag.

The light chain library is constructed in the same way as the heavy chain and contains 2.5×10$^6$ members. Plaque screening, using an anti-kappa chain antibody, indicates that 60% of the library contained express light chain inserts. A small percentage of inserts results from incomplete dephosphorylation of vector after cleavage with Sac I and Xba I.

Once obtained, the two libraries are used to construct a combinatorial library by crossing them at the EcoR I site. To accomplish the cross, DNA is first purified from each library.

The Lambda Lc2 library prepared in Example 2d is amplified and 500 µg of Lambda Lc2 expression library phage DNA is prepared from the amplified phage stock using the procedures described in *Molecular Cloning: A Laboratory Manual*, Maniatis et al., eds., Cold Spring Harbor, N.Y. (1982). Fifty µg of this amplified expression library phage DNA is maintained in a solution containing 100 units of MLu I restriction endonuclease (Boehringer Mannheim, Indianapolis, Ind.) in 200 µl of a buffer supplied by the endonuclease manufacturer for 1.5 hours at 37° C. The solution is then extracted with a mixture of phenol and chloroform. The DNA is then ethanol precipitated and resuspended in 100 µl of water. This solution is admixed with 100 units of the restriction endonuclease EcoR I (Boehringer) in a final volume of 200 µl of buffer containing the components specified by the manufacturer. This solution is maintained at 37° C. for 1.5 hours and the solution is then extracted with a mixture of phenol and chloroform. The DNA was ethanol precipitated and the DNA resuspended in TE.

The Lambda Hc2 expression library prepared in Example 2d is amplified and 500 µg of Lambda Hc2 expression library phage DNA is prepared using the methods detailed above. 50 µg of this amplified library phage DNA is maintained in a solution containing 100 units of Hind III restriction endonuclease (Boehringer) in 200 µl of a buffer supplied by the endonuclease manufacturer for 1.5 hours at 37° C. The solution is then extracted with a mixture of phenol and chloroform saturated with 0.1 M Tris-HCl, pH 7.5. The DNA is then ethanol precipitated and re-suspended in 100 μl of water. This solution is admixed with 100 units of the restriction endonuclease EcoR I (Boehringer) in a final volume of 200 μl of buffer containing the components specified by the manufacturer. This solution is maintained at 37° C for 1.5 hours and the solution is then extracted with a mixture of phenol and chloroform. The DNA is ethanol precipitated and the DNA re-suspended in TE.

The restriction digested Hc2 and Lc2 expression libraries are ligated together. To that end, a DNA admixture consists of 1 μg of Hc2 and 1 μg of Lc2 phage library DNA is prepared in a 10 μl reaction using the reagents supplied in a ligation kit (Stratagene). The DNA admixture is warmed to 45° C for 5 minutes to melt any cohesive termini that may have reannealed. The admixture is then chilled to 0° C. to prevent religation. Bacteriophage T4 DNA ligase (0.1 Weiss units which is equivalent to 0.02 units as determined in an exonuclease resistance assay) is admixed into the chilled DNA solution along with 1 μl of 5 mM ATP and 1 μl 10×bacteriophage T4 DNA ligase buffer (10×buffer is prepared by admixing 200 mM Tris-HCl, pH 7.6, 50 mM $MgCl_2$, 50 mM DTT, and 500 μg/ml BSA) to form a ligation admixture. After ligation for 16 hr at 40° C., 1 μl of the ligated the phage DNA is packaged with Gigapack Gold II packaging extract and plated on XL1-Blue cells prepared according to the manufacturers instructions to form a Lambda phage library of dicistronic expression vectors capable of expressing heavy and light chains derived from the NPN-immunized mouse. A portion of the clones obtained are used to determine the effectiveness of the combination.

f. Selection of Anti-NPN Reactive Heterodimer-Producing Dicistronic Vectors

The combinatorial Fab expression library prepared above in Example 2a was screened to identify clones having affinity for NPN. To determine the frequency of the phage clones which co-expressed the light and heavy chain fragments, duplicate lifts of the light chain, heavy chain and combinatorial libraries were screened as above for light and heavy chain expression. In this study of approximately 500 recombinant phage, approximately 60% co-expressed light and heavy chain proteins.

All three libraries, the light chain, the heavy chain and the combinatorial, were screened to determine if they contained recombinant phage that expressed antibody fragments which bound NPN. In a typical procedure 30,000 phage were plated on XL1-Blue cells and duplicate lifts with nitrocellulose were screened for binding to NPN coupled to $^{125}I$ labeled BSA. The BSA was iodinated following the Chloramine-T method as described by Bolton et al., *Biochem.*, 133:529–534 (1973). Duplicate screens of 80,000 recombinant phage from the light chain library and a similar number from the heavy chain library did not identify any clones which bound the antigen. In contrast, the screen of a similar number of clones from the Fab expression library identified many phage plaques that bound NPN. This observation indicates that under conditions where many heavy chains in combination with light chains bind to antigen the same heavy or light chains alone do not. Therefore, in the case of NPN, it is believed that there are many heavy and light chains that only bind antigen when they are combined with specific light and heavy chains, respectively.

To assess the ability to screen large numbers of clones and obtain a more quantitative estimate of the frequency of antigen binding clones in the combinatorial library, one million phage plaques were screened and approximately 100 clones which bound to antigen were identified. For six clones which were believed to bind NPN, a region of the plate containing the six positive and approximately 20 surrounding bacteriophage plaques was selected and each plaque was cored, replated, and screened with duplicate lifts. As expected, approximately one in twenty of the phage specifically bound to antigen. Cores of regions of the plated phage believed to be negative did not give positives on replating.

Clone 2b, one of the plaques which reacted with NPN, was excised according to an in vivo excision protocol where 200 μl of phage stock and 200 μl of a F+derivative of XL1-Blue ($A_{600}$=1.00) (Stratagene) were admixed with 1 μl of M13mp8 helper phage ($1\times10^{10}$ pfu/milliliter (ml)) and maintained at 37° C. for 15 minutes. After a four hour maintenance in Luria-Bertani (LB) medium and heating at 70° C. for 20 minutes to heat kill the XL1-Blue cells, the phagemids were re-infected into XL1-Blue cells and plated onto LB plates containing ampicillin. This procedure converted the cloned insert from the Lambda Zap II vector into a plasmid vector to allow easy manipulation and sequencing (Stratagene). The phagemid DNA encoding the $V_H$ and part of the $V_L$ was then determined by DNA sequencing using the Sanger dideoxy method described in Sanger et al., *Proc. Natl. Acad. Sci.*, 74:5463–5467 (1977) using a Sequenase kit according to manufacturer's instructions (US Biochemical Corp., Cleveland, Ohio). The nucleotide residue sequence of Clone 2b Fd chain is listed in the Sequence Listing as SEQ ID NO 99. The nucleotide this residue sequences of the kappa light chain variable and constant regions are listed in the Sequence Listing as SEQ ID NO 100 and SEQ ID NO 101, respectively.

g. Preparation of a DNA Sequence Encoding a Filamentous Phage Coat Protein Membrane Anchor cpVIII Membrane Anchor: M13mp18, a commercially available bacteriophage vector (Pharmacia, Piscataway, N.J.), was used as a source for isolating the gene encoding cpVIII. The sequence of the gene encoding the membrane anchor domain of cpVIII listed in Sequence Listing as SEQ ID NO 102, was modified through PCR amplification to incorporate the restriction endonuclease sites, Spe I and EcoR I, and two stop codons prior to the EcoR I site. The corresponding amino acid residue sequence of the membrane anchor domain of cpVIII is listed as SEQ ID NO 17.

To prepare a modified cpVIII, replicative form DNA from M13mp18 was first isolated. Briefly, into 2 ml of LB (Luria-Bertani medium), 50 μl of a culture of a bacterial strain carrying an F' episome (JM107, JM109 or TG1) was admixed with a one tenth suspension of bacteriophage particles derived from a single plaque. The admixture was incubated for 4 to 5 hours at 37° C. with constant agitation. The admixture was then centrifuged at 12,000×g for 5 minutes to pellet the infected bacteria. After the supernatant was removed, the pellet was resuspended by vigorous vortexing in 100 μl of ice-cold solution I. Solution I was prepared by admixing 50 mM glucose, 10 mM EDTA and 25 mM Tris-HCl, pH 8.0, and autoclaving for 15 minutes.

To the bacterial suspension, 200 μl of freshly prepared Solution II was admixed and the tube was rapidly inverted five times. Solution II was prepared by admixing 0.2 N NaOH and 1% SDS. To the bacterial suspension, 150 μl of ice-cold Solution III was admixed and the tube was vortexed gently in an inverted position for 10 seconds to disperse Solution III through the viscous bacterial lysate. Solution III was prepared by admixing 60 ml of 5 M potassium acetate, 11.5 ml of glacial acetic acid and 28.5 ml of water. The resultant bacterial lysate was then stored on ice for 5 minutes followed by centrifugation at 12,000×g for 5 minutes at 4° C. in a microfuge. The resultant supernatant was recovered and transferred to a new tube. To the supernatant was added an equal volume of phenolchloroform and the admixture was vortexed. The admixture was then centrifuged at 12,000×g for 2 minutes in a microfuge. The resultant supernatant was transferred to a new tube and the double-stranded for 2 minutes. The resultant PCR modified cpVIII membrane anchor domain DNA fragment from M13mp18 containing samples were then purified with Gene Clean (BIO101, La Jolla, Calif.), extracted twice with phenol/chloroform, once with chloroform followed by ethanol precipitation and were stored at −70° C. in 10 mM Tris-HCl, pH 7.5, and 1 mM EDTA.

TABLE 7

| SEQ. ID. NO. | | | | Primer |
|---|---|---|---|---|
| (103)[1] | AK 5 | (F) | 5' | GTGCCCAGGGATTGTACTAGTGCTGAGGGTGACGAT 3' |
| (104)[2] | AK 6 | (B) | 5' | ACTCGAATTCTATCAGCTTGCTTTCGAGGTGAA 3' |
| (105)[3] | Hc3 | (F) | 5' | AGGTCCAGCTTCTCGAGTCTGG 3' |
| (106)[4] | AK 7 | (B) | 5' | GTCACCCTCAGCACTAGTACAATCCCTGGGCAC 3' |
| (107)[5] | G-3 | (F) | 5' | GAGACGACTAGTGGTGGCGGTGGCTCTCCATTC GTTTGTGAATATCAA 3' |
| (108)[6] | G-3 | (B) | 5' | TTACTAGCTAGCATAATAACGGAATACCCAAAA GAACTGG 3' |
| (109)[7] | LAC-F | | 5' | TATGCTAGCTAGTAACACGACAGGTTTCCCGAC TGG 3' |
| (110)[8] | LAC-B | | 5' | ACCGAGCTCGAATTCGTAATCATGGTC 3' |
| (125)9 | LAC-B' | | 5' | AGCTGTTGAATTCGTGAAATTGTTATCCGCT 3' |

(F) Forward Primer
(B) Backward Primer
[1]From 5' to 3': the overlapping sequence for $C_H1$ 3' end is double underlined; the Spe I restriction site sequence is single underlined; the overlapping sequence for cpVIII is double underlined.
[2]EcoR I restriction site sequence is single underlined
[3]Xho I restriction site sequence is underlined
[4]From 5' to 3': the overlapping sequence for cpVIII is double underlined; the Spe I restriction site sequence is single underlined; the overlapping sequence for $C_H1$ 3' end is double underlined.
[5]From 5' to 3': Spe I restriction site sequence is single underlined; the overlapping sequence with the 5' end of cpIII is double underlined
[6]From 5' to 3': Nhe I restriction site sequence is single underlined; the overlapping sequence with 3' end of cpIII is double underlined.
[7]From 5' to 3': overlapping sequence with the 3' end of cpIII is double underlined; Nhe I restriction sequence begins with the nucleotide residue "G" at position 4 and extends 5 more residues = GCTAGC.
[8]EcoR I restriction site sequence is single underlined.
9Alternative backwards primer for amplifying LacZ; EcoR I restriction site sequence is single underlined.

bacteriophage DNA was precipitated with 2 volumes of ethanol at room temperature. After allowing the admixture to stand at room temperature for 2 minutes, the admixture was centrifuged to pellet the DNA. The supernatant was removed and the pelleted replicative form DNA was resuspended in 25 μl of Tris-HCl, pH 7.6, and 10 mM EDTA (TE).

The double-stranded M13mp18 replicative form DNA was then used as a template for PCR. Primers, AK 5 (SEQ ID NO 103) and AK 6 (SEQ ID NO 104), the sequences of which are listed in. Table 7 below, were used in the PCR reaction to amplify the mature gene for cpVIII member anchor domain and incorporate the two cloning sites, Spe I and EcoR I. For the PCR reaction, 2 μl containing 1 ng of M13mp18 replicative form DNA was admixed with 10 μl of 10×PCR buffer purchased commercially (Promega Biotech, Madison, Wis.) in a 0.5 ml microfuge tube. To the DNA admixture, 8 μl of a 2.5 mM solution of dNTPs (DATP, dCTP, dGTP, dTTP) was admixed to result in a final concentration of 200 micromolar (uM). Three μl (equivalent to 60 picomoles (pM)) of the 5' forward AK 5 primer and 3 μl (60 pM) of the 3' backward AK 6 primer was admixed into the DNA solution. To the admixture, 73 μl of sterile water and 1 μl/5 units of polymerase (Promega Biotech) was added. Two drops of mineral oil were placed on top of the admixture and 40 rounds of PCR amplification in a thermocycler were performed. The amplification cycle consisted of 52° C. for 2 minutes, 72° C. for 1.5 minutes and 91° C.

To verify amplification of the modified cpVIII membrane anchor domain, the PCR purified DNA products were electrophoresed in a 1% agarose gel. The expected size of the cpVIII was approximately 150 base pairs. The area in the agarose containing the modified cpVIII DNA fragment was isolated from the agarose as described above. The sequence of the isolated modified cpVIII DNA fragment is listed as SEQ ID NO 111. The isolated cpVIII DNA fragment was then admixed with a similarly prepared fragment of modified Fd as described below in Example 2i in order to form a DNA segment encoding the fusion protein Fd-cpVIII.

cpIII Membrane Anchor: M13mp18 was also used as a source for isolating the gene encoding the membrane anchor domain at cpIII, the sequence of which is listed in the Sequence Listing as SEQ ID NO 112. The amino acid residue sequence of membrane anchor domain cpIII is listed in SEQ ID NO 16. M13mp18 replicative form DNA was prepared as described above and used as a template for two PCR amplifications for construction of a DNA fragment consisting of the mature gene for cpIII membrane anchor domain located 5' to a sequence encoding the LacZ promoter, operator and cap-binding site for controlling light chain expression. The restriction sites, Spe I and EcoR I, were created in the amplification reactions and were located at the 5' and 3' ends of the fragment respectively. The procedure for creating this fragment by combining the products of two separate PCR amplifications is described below.

The primer pair, G-3(F) (SEQ ID NO 107) and G-3(B) (SEQ ID NO 108) listed in Table 7, was used in the first PCR reaction as performed above to amplify the cpIII membrane anchor gene and incorporate Spe .I and Nhe I restriction sites into the fragment. The amplified PCR fragment also contained nucleotide sequences for encoding a five amino acid tether composed of four glycerine residues and one serine juxtaposed between the heavy chain and cpIII encoding domains. Once expressed, the five amino acid sequence lacking an orderly secondary structure served to minimize the interaction between the Fab and cpIII domains. The resultant PCR modified cpIII DNA fragment having Spe I and Nhe I sites in the 5' and 3' ends, respectively, of the fragment was verified and purified as described above. The sequence of the PCR modified cpIII membrane anchor domain DNA fragment is listed in the Sequence Listing as SEQ ID NO 113. A second PCR amplification using the primer pairs, Lac-F (SEQ ID NO 109) and Lac-B (SEQ ID NO 110) listed in Table 7, was performed on a separate aliquot of M13mp18 replicative form template DNA to amplify the LacZ promoter, operator and Cap-binding site having a 5' Nhe I site and a 3' EcoR I site. The primers used for this amplification were designed to incorporate a Nhe I site on the 5' end of the amplified fragment to overlap with a portion of the 3' end of the cpIII gene fragment and of the Nhe I site 3' to the amplified cpIII fragment. The reaction and purification of the PCR product was performed as described above. The sequence of the resultant PCR modified cpIII DNA fragment having a 5' Nhe I and 3' EcoR I restriction site is listed in the Sequence Listing as SEQ ID NO 114.

An alternative Lac-B primer for use in constructing the cpIII membrane anchor and LacZ promotor region was Lac-B' as shown in Table 7. The amplification reactions were performed as described above with the exception that in the second PCR amplification, Lac-B' was used with Lac-F instead of Lac-B. The product from the amplification reaction is listed in the sequence listing as SEQ ID NO 114 from nucleotide position 1 to nucleotide position 172. The use of Lac-B' resulted in a LacZ region lacking 29 nucleotides on the 3' end but was functionally equivalent to the longer fragment produced with the Lac-F and Lac-B primers.

The products of the first and second PCR amplifications using the primer pairs 6-3(F) and 6-3(B) and Lac-F and Lac-B were then recombined at the nucleotides corresponding to cpIII membrane anchor overlap and Nhe I restriction site and subjected to a second round of PCR using the G3-F (SEQ ID NO 107) and Lac-B (SEQ ID NO 110) primer pair to form a recombined PCR DNA fragment product consisting of the following: a 5' Spe I restriction site; a cpIII DNA membrane anchor domain beginning at the nucleotide residue sequence which corresponds to the amino acid residue 198 of the entire mature cpIII protein; an endogenous stop site provided by the membrane anchor at amino acid residue number 112; a Nhe I restriction site, a LacZ promoter, operator and Cap-binding site sequence; and a 3' EcoR I restriction site. The recombined PCR modified cpIII membrane anchor domain DNA fragment was then restriction digested with Spe I and EcoR I to produce a DNA fragment for directional ligation into a pComb2 phagemid expression vector having only one Spe I site prepared in Example la(iv) to form a pComb2-III (also referred to as pComb2-III) phagemid expression vector as described in Example 1b(ii).

h. Isolation of Anti-NPN Coding V$_H$ DNA Segment

To prepare modified Fd fragments for recombination with the PCR modified cpVIII membrane anchor domain fragment to form a Fd-cpVIII DNA fusion product, PCR amplification as described above was performed using Clone 2b, prepared in Example 2f, as a template. The primers, Hc3 (SEQ ID NO 105) and AK 7 (SEQ ID NO 106), the sequences of which are listed in Table 7, were used in PCR to amplify the Fd portion of the Clone 2b and incorporate Xho I and Spe I cloning sites along with a cpVIII overlapping sequence. The amplified PCR modified Fd product was purified, electrophoresed and isolated from 1% agarose gels as described above. The size of the Fd fragment was 680 base pairs.

i. Preparation of a DNA Segment Encoding a Portion of the Fusion Protein Fd-cpVIII The purified PCR modified Fd DNA fragment containing cpVIII overlapping nucleotide sequences prepared above was then admixed with the PCR modified cpVIII membrane anchor domain fragment to form an admixture. The fragments in the admixture were allowed to recombine at their complementary regions. The admixture containing the recombined PCR fragments was then subjected to a second round of PCR amplification as described above using the end primer pair AK 6 (SEQ ID NO 104) and Hc3 (SEQ ID NO 105) (Table 7). The corresponding product of the PCR amplification was purified and electrophoresed on agarose gels as described above. The PCR product was determined to be approximately 830 base pairs (Fd=680+150) confirming the fusion of Fd with cpVIII. The sequence of the PCR product linking the Fd sequence with the cpVIII sequence in frame in a 5' to 3' direction is listed as SEQ ID NO 115. The Fd-cpVIII fusion product was then used in directional ligations described in Example 2j for the construction of a pCBAK8-2b dicistronic phagemid expression vector.

j. Construction of pCBAK8-2b Dicistronic Expression Vector

To construct a phagemid vector for the coordinate expression of a Fd-cpVIII fusion protein is with kappa light chain, the PCR amplified Fd-cpVIII fusion product prepared in above in Example 2i was first ligated into Clone 2b phagemid expression vector isolated from the NPN combinatorial library prepared in Example 2f. For the ligation, the Fd-cpVIII PCR fusion product was first restriction digested with Xho I and EcoR I. Clone 2b phagemid vector was similarly digested resulting in the removal of the cloning and decapeptide regions. The digested Fd-cpVIII fragment was admixed and ligated into the digested Clone 2b at the cohesive termini generated by Xho I and EcoR I restriction digestion. The ligation resulted in operatively linking the nucleotide residue sequence encoding the Fd-cpVIII polypeptide fusion protein to a second cassette having the nucleotide residue sequences encoding the ribosome binding site, a pelB leader sequence and the kappa light chain already present in Clone 2b to form a dicistronic DNA molecule in the original Clone 2b phagemid expression vector.

E. coli, strain TG1, was then transformed with the phagemid containing the dicistronic DNA molecule and transformants were selected on ampicillin as the original Clone 2b contained an ampicillin selectable resistance marker gene. For high efficiency electro-transformation of E. coli, a 1:100 volume of an overnight culture of TG1 cells was inoculated into one liter of L-broth (1 Bacto tryptone, 0.5% Bacto yeast extract, 0.5% NaCl). The cell suspension was maintained at 37° C. with vigorous shaking to a absorbance at 600 nm of 0.5 to 1.0. The cell suspension in log phase growth was then harvested by first chilling the flask on ice for 15 to 30 minutes followed by centrifugation in a cold rotor at 4000×g for 15 minutes to pellet the bacteria. The resultant supernatant was removed and the bacterial cell pellet was resuspended in a total of one liter of cold water to form a cell suspension. The centrifugation and resuspension procedure was repeated two more times and after the final centrifugation, the cell pellet was resuspended in 20 ml of cold 10% glycerol. The resuspended cell suspension was then centrifuged to form a cell pellet. The resultant cell pellet was resuspended to a final volume of 2 to 3 ml in cold 10% glycerol resulting in a cell concentration of 1 to $3 \times 10^{10}$ cells/ml. For the electro-transformation procedure, 40 µl of the prepared cell suspension was admixed with 1 to 2 µof phagemid DNA to form a cell-phagemid DNA admixture. The resultant admixture was mixed and allowed to sit on ice for one minute. An electroporation apparatus, for example a Gene Pulsar, was set a 25 uF and 2.5 kV. The pulse controller was set to 200 ohms. The cell-DNA admixture was transferred to a cold 0.2 cm electroporation cuvette. The cuvette was then placed in the chilled safety chamber and pulsed once at the above settings. To the pulsed admixture, 1 ml of SOC medium was then admixed and the cells were resuspended with a Pasteur pipette (SOC medium was prepared by admixing 2% Bacto tryptone, 0.5% Bacto yeast extract, 10 mM NaCl, 2.5 mM KCl, 10 mM $MgCl_2$, 10 mM $MgSO_4$, and 20 mM glucose). The cells suspension was then transferred to a 17×100 mm polypropylene tube and maintained at 37° C. for one hour. After the maintenance period, the transformed TG1 cells were then plated on ampicillin LB plates for selection of ampicillin resistant colonies containing the phagemid which provided the selectable marker gene.

Ampicillin resistant colonies were selected and analyzed for the correct insert size and expression of Fab. Briefly, DNA minipreps of selected colonies were prepared for the isolation of phagemid DNA. The isolated phagemid DNA from each miniprep was restriction digested with Xho I and EcoR I and the digests were electrophoresed on a 1% agarose gel. Clone AK16 was selected as an 830 bp fragment was visualized on the gels confirming the insertion of the Fd-cpVIII PCR fusion product into digested Clone 2b.

Clone AK16 phagemid was then restriction digested with Xho I and Xba I and the nucleotide residue sequence of the dicistronic DNA molecule encoding the Fd-cpVIII fusion protein, the ribosome binding site and pelB leader sequence for expression of the light chain, a spacer region and the 2b kappa light chain was isolated by agarose gel electrophoresis. The isolated dicistronic DNA fragment was then ligated into a Xho I and Xba I restriction digested pCBAKO expression vector prepared in Example 1c(ii) to form a dicistronic phagemid expression vector designated pCBAK8-2b.

The resultant pCBAK8-2b expression vector consisted of nucleotide residue sequences encoding the following elements: f1 filamentous phage origin of replication; a chloramphenicol acetyl transferase selectable resistance marker gene; an inducible LacZ promoter upstream from the LacZ gene; a multiple cloning site flanked by T3 and T7 polymerase promoters; and the dicistronic DNA molecule (a first cassette consisting of a ribosome binding site, a pelB leader, and a Fd-cpVIII DNA fusion product operatively linked to a second cassette consisting of a second ribosome binding site, a second pelB leader, and a kappa light chain).

k. Construction of pCBAK3-2b Dicistronic Expression Vector

To construct a phagemid vector for the coordinate expression of a Fd-cpIII fusion protein with kappa light chain, the PCR amplified and recombined cpIII membrane anchor and LacZ promotor region fragment prepared in Example 2g having a 5' Spe I and 3' EcoR I restriction site was first directionally ligated into a pComb2 phagemid expression vector previously digested with Spe I and EcoR I prepared in Example 1a(iv) to form a pComb2-3 (also called pComb2-III) phagemid vector. See Example 1b(ii) for details of vector construction. This vector was used in this invention when ampicillin resistant vectors were preferred. Thus, the resultant pComb2-3 vector, having only one Spe I restriction site, contained separate LacZ promoter/operator sequences for directing the separate expression of the heavy chain (Fd)-cpIII fusion product and the light chain protein. The expressed proteins were directed to the periplasmic space by pelB leader sequences for functional assembly on the membrane. Inclusion of the phage F1 intergenic region in the vector allowed for packaging of single stranded phagemid with the aid of helper phage. The use of helper phage superinfection lead to expression of two form of cpIII. Thus, normal phage morphogenesis was perturbed by competition between the Fab-cpIII fusion and the native cpIII of the helper phage for incorporation into the virion as schematically shown in FIG. 8 for Fab-cpVIII fusions.

For producing chloramphenicol resistant vectors for use in this invention, the resultant pComb2-3 phagemid vector was then restriction digested with Sac II and Apa I to form an isolated fragment. The resultant isolated fragment containing the expression control sequences and the cpIII sequence was then directionally ligated into a similarly digested pCBAKO phagemid vector prepared in Example 1c(ii) to form a pCBAK3 phagemid expression vector. This vector lacked Fd and kappa light chain sequences.

A chloramphenicol-resistant phagemid expression vector, pCBAK3-2b, for the expression of a fusion protein and kappa light chain was then constructed. Briefly, the pCBAK3 phagemid expression vector prepared above was first digested with Xho I and Spe I to form a linearized pCBAK3 phagemid expression vector. PCR amplified and modified Fd fragment, prepared in Example 2h containing Xho I and Spe I sites, was subsequently restriction digested with Xho I and Spe I. The resultant Fd fragment was then directionally ligated via cohesive termini into the Xho I and Spe I restriction digested pCBAK3 phagemid expression vector to form a second phagemid expression vector in which the PCR modified Fd fragment was operatively linked in-frame to nucleotide residue sequences encoding cpIII. E. coli strain XL1-Blue (Stratagene) was then transformed with the above phagemid vector containing Fd-cpIII. Transformants containing the Fd-cpIII encoding phagemid were selected on chloramphenicol. Phagemid DNA was isolated from chloramphenicol resistant clones and was restriction digested with Sac I and Xba I to form a linearized phagemid expression vector into which a Sac I and Xba I light chain fragment prepared below was directionally ligated.

Phagemid Clone 2b, isolated from the original combinatorial library as described in Example 2a, was restriction digested with Sac I and Xba I to isolate the nucleotide residue sequence encoding the kappa light chain. The isolated kappa light chain sequence was then directionally ligated into the Sac I and Xba I restriction digested phagemid expression vector prepared above containing Fd-cpIII to form the phagemid expression vector, pCBAK3-2b. The resultant vector contained the nucleotide residue sequence of a dicistronic DNA molecule for the coordinate expression of a Fd-cpIII fusion protein with kappa light chain. The resultant phagemid expression vector consisted of nucleotide residue sequences encoding the following elements: f1 filamentous phage origin of replication; a chloramphenicol acetyl transferase selectable resistance marker gene; an inducible LacZ promoter upstream from the LacZ gene; a multiple cloning site flanked by T3 and T7 polymerase promoters; and the dicistronic molecule (a first cassette consisting of a first ribosome binding site and pelB leader operatively linked to Fd-cpIII operatively linked to a second cassette consisting of a second LacZ, a second ribosome binding site, and a second pelB leader operatively linked to a kappa light chain).

XL1-Blue cells were then transformed with the phagemid expression vector pCBAK3-2b. Transformed colonies containing the chloramphenicol resistant phagemids were selected as described above and analyzed for the correct size insert and expression of Fab as described in Example 2j. Following verification of the insert and expression of Fab in the pCBAK3-2b phagemid vector, XL1-Blue cells were then transformed and induced for the expression of Fab antibodies as described in Examples 3 and 4.

The results of the expression, selection and screening of the Fab-cpIII fusions revealed an advantage of monovalent display provided by Fab-cpIII fusions over multivalent displays provided by Fab-cpVIII fusions as it allowed for the sorting of clones based on affinity as well as specificity, as does the immune system. A 253-fold enrichment of the tight binding clone 10C over the weaker binding clone 7E using the pComb3 system as described in Barbas et al., *Proc. Natl. Acad. Sci. USA*, 88:7978–7982 (1991). Studies with peptide libraries on phage that displayed four to five copies of the peptide on the phage surface have shown that multivalency prevented the separation of phage displaying moderate affinity peptides ($10^{-6}$ M) from those displaying high affinity peptides ($10^{-9}$ M). Cwirla et al., *Proc. Natl. Acad. Sci. USA*, 87:6378–6382 (1990). Multivalency lead to a chelation effect that reduces the ability to discriminate between phage-bearing high affinity Fabs from those bearing low affinity Fabs.

The use of the system was further demonstrated by sorting a previously characterized (one binder per 5000 clones) human combinatorial antitetanus toxoid Fab library as described in Example 6 and by Persson et al., *Proc. Natl. Acad. Sci. USA*, 88:2432–2436 (1991). The library, originally in a lambda phage vector system, was reconstructed in pComb2-3 retaining the original pairings of heavy and light chains. The library size, $10^7$ clones was 10-fold larger than the original lambda phage library. After a single round of panning, 13 or 57 clones picked were determined to be tetanus toxoid binders which represented a $10^3$-fold enrichment. Following the third panning, the phage yield had increased 200-fold, indicating enrichment of specific phage. All the clones were thus antigen-specific binders. Large combinatorial libraries of $10^8$ members are thus accessible using this system. Even larger libraries are achieved by mutagenesis as described in Examples 6–8.

3. Expression of Anti-NPN Heterodimer on Phage Surfaces

For expression of antibody Fab directed against NPN on phage surfaces, XL1-Blue cells were separately transformed with the phagemid vectors, pCBAK8-2b and pCBAK3-2b, prepared in Examples 2j and 2k, respectively. The transformants were selected on LB plates containing 30 μg/ml chloramphenicol. Antibiotic resistant colonies were selected for each phagemid transformation and grown in liquid cultures at 37° C. in super broth (super broth was prepared by admixing the following: 20 g 3 [N-Morpholino] propanesulfonic acid (MOPS); 60 g tryptone; 40 g yeast extract; and 2 liter of water; adjust pH to 7.0 with 10 m NaOH) containing 30 μg/ml chloramphenicol and 12.5 μg/ml tetracycline for the respective antibiotic selection of the phagemid and the F' episome. The antibiotic resistant transformed XL1-Blue cells were diluted to an optical density ($OD_{600nm}$) of 0.4 in super broth. The inducer, isopropyl thiogalactopyranoside (IPTG), was admixed to the bacterial suspension for a final concentration of 1 mM and the admixture was maintained at 37° C. for 1 hour to induce the expression of the fusion protein and kappa light chain from the LacZ promoter. Helper phage, either R408 or VCS M13 (Stratagene), was then admixed to the induced bacterial suspension at a ratio of 10–20 helper phage to 1 transformed bacterial cell to initiate the generation of copies of the sense strand of the phagemid DNA. The admixture containing the helper phage was then maintained for an additional two hours at 37° C. to allow for filamentous bacteriophage assembly wherein the expressed anti-NPN Fab antibodies fused to either bacteriophage membrane anchor domains of cpVIII or cpIII were incorporated into surface of the bacteriophage particles. The bacterial suspension was then centrifuged resulting in a bacterial cell pellet and a supernatant containing phage. The supernatant was removed, collected and assayed as described below for the presence of functional anti-NPN Fab molecules anchored to the phage particles by either cpVIII or cpIII.

4. Assays for Verifying the Presence and Function of Anti-NPN Heterodimer on the Surface of Filamentous Phage a. Electron Microscopy To localize functional Fab molecules, the binding to antigen labelled with colloidal gold was studied. Phage containing supernatants and bacterial cells prepared in Example 3 were spotted on formvar (Polysciences, Inc., Warrington, Pa.) coated grids affixed onto a solid phase. In some experiments grids were coated with cells and infected with phage in situ. Subsequently grids were blocked with 1% bovine serum albumin (BSA) in PBS at pH 7.2, washed and incubated with 2–7 nanometer (nm) colloidal gold particles coated with BSA-NPN hapten conjugate for a time period sufficient to form a labeled immunoreaction complex. The grids were washed to remove excess gold particles and negatively stained in uranylacetate and visualized by electron microscopy.

Examination of filamentous phage and permeablized cells producing phage revealed specific labelling of phage or exposed bacterial membranes. Phage were observed to contain 1 to 24 copies of antigen binding sites per particle. Neither helper phage alone nor intact *E. coli* labelled with antigen. Background nonspecific binding was very low. Filamentous phage particles emerging from the *E. coli* surfaces were labelled with antigen as shown in FIG. 9.

The generation of a related phage surface expression vector utilizing cpIII as a fusion partner with Clone 2b,-pCBAK3-2b, revealed specific antigen labelling to the phage head but not the column. Additionally human anti-tetanus Fab expressed as a cpIII fusion did not bind to BSA-NPN antigen.

b. Phase Elisa

Microtitration plates were coated with NPN-BSA conjugate (0.1 ml, 1 μg/ml in 0.1 M Tris-HCl, pH 9.2), and blocked with 1% BSA in PBS. Serial two fold dilutions of pCBAK8-2b derived phage (0.1 ml), prepared in Example 3, were added to the pre-coated microtitration plate and incubated for 3 hours at ambient temperature or 16 hours at 4° C. The plates were washed with PBS and goat anti-kappa alkaline phosphatase conjugate (Fisher Biotech, Pittsburgh, Pa.) added (0.1 ml diluted 1/1000 in PBS containing 0.1% BSA) and incubated for 2 hours at room temperature. The plates were washed in PBS and substrate added (0.1 ml, 1 mg/ml p-nitrophenylphosphate in 0.1 M Tris-HCl, pH 9.5, containing 50 mM $MgCl_2$). After incubation at 37° C. for signal development, the optical densities at 400 nm were determined. Competition assays were performed with the addition of increasing amounts of free NPN hapten ranging from zero up to 5 mg/well.

The ELISA assays confirmed the presence of functional antibody Fab. In a two site ELISA on NPN antigen coated plates when probed with anti-mouse kappa chain enzyme conjugate, phage supernatant generated from helper phage infection of cells carrying the pCBAK8-2b construct exhibited expected titration curves with serial two fold dilutions of phage containing antibody. The results of the two-site ELISA are shown in FIG. 10. For a signal to be generated in this assay, the phage particle must (i) have functionally associated Fd and kappa chains and (ii) be multivalent. Specificity of the particle was assessed by inhibiting binding to the plate in the presence of increasing concentrations free hapten. The generated phage particles exhibited binding to solid phase of the ELISA and could be inhibited by addition of hapten as shown in FIG. 11. Complete inhibition was achieved when 5 ng of free NPN hapten was used in the assay. Helper phage did not give a signal in the ELISA. These results show the functional assembly of antibody heavy and light chain polypeptides to form an epitope-binding complex that is present on the surface of the phage particle and able to bind the preselected ligand chapter containing an epitope.

c. Antigen Specific Precipitation of Phage

Phage supernatant from XL1-Blue was transformed with the pCBAK8-2b dicistronic expression vector prepared in Example 3 (1 ml) was incubated with BSA-NPN conjugate (10 µl, 2 mg/ml) for 18 hours at 4° C. The mixture was then pelleted by centrifugation at 3000 rpm on a bench top centrifuge and the appearance of precipitate noted. Helper phage was used as a control. The pellet was washed repeatedly in cold PBS (5×3 ml/wash) and then resuspended in LB (0.5 ml). The solubilized precipitates were added to fresh XL1-Blue cells (0.5 ml of overnight culture), incubated for 1 hour at 37° C. and aliquots plated out on LB agar containing chloramphenicol (30 µg/ml). Colonies were selected randomly. Colony lifts on nitrocellulose were treated with lysozyme to digest the cell wall, briefly treated with chloroform to breakdown the outer membrane, blocked in BSA 1% in PBS and incubated with $^{125}$I labelled BSA-NPN antigen. After several washes in PBS (containing 0.05% Tween-20), film was exposed to the washed and dried filter overnight at −70° C. and the autoradiographs were then developed.

Precipitates were obtained with antibody containing phage but not helper phage in the presence of BSA-NPN. In addition, the particles retained infectivity on subsequent incubation with bacterial cells carrying the F' episome and generated 4×10$^5$ colonies from a single solubilized precipitate.

Additionally, DNA restriction analysis was carried out to determine the presence of heavy and light chain inserts. DNA restriction analysis of the clones revealed the presence of a Xho I and Xba I fragment of 1.4 kb as expected for Fd-cpVIII fusion construct and kappa chain insert.

These results give additional evidence for antigen specificity and multivalency. In addition to providing immunological parameters, this precipitation offers possibilities for facile enrichment of antigen specific phage particles. In principle, phage containing specific antibodies can be highly enriched by precipitation with antigens (which may be cell surface markers, viral, bacterial as well as synthetic molecules). The washed antigen-antibody precipitates can be solubilized by the addition of excess antigen and viable phage recovered. For the recovery of rare species an immobilized antigen may be used which opens the way for differential affinity elution.

In order to demonstrate the utility of immobilized antigen for the enrichment of clones of defined binding specificity, a panning experiment was performed. An ampicillin resistant phagemid expressing an anti-tetanus Fab as a cpVIII fusion was constructed. Rescue of this clone with helper phage produced phage encoding the ampicillin resistant a phagemid which displayed the anti-tetanus Fab on their coat. These phage encoding tetanus specificity were admixed with NPN hapten encoding phage (1:100) and allowed to bind to a microtitration plate coated with tetanus toxoid. Following a one hour maintenance period, the plate was washed extensively and phage were then eluted with a low pH buffer. Infection of XL1-Blue cells in log phase growth and subsequent plating of aliquots on ampicillin and chloramphenicol allowed for direct quantitation of enrichment. Examination of over 1,000 colonies showed that ampicillin resistant colonies derived from the eluted phage exceeded chloramphenicol resistant colonies by 27 to 1. Therefore, panning enriched the phage displaying the anti-tetanus Fab by 2700 fold. This result suggests that a clone of defined specificity present at one part per million will dominate over nonspecific clones following two rounds of panning.

5. Advantages of Assembling Combinatorial Antibody Fab Libraries Along Phage Surfaces A powerful technique for generating libraries with $10^{8-9}$ members and selecting from the library of combinatorial Fabs with preselected binding activities, is presented. In the vector described herein, the restriction cloning sites for inserting PCR generated antibody fragments have been retained as previously reported for the lambda vector. The rescue of the genes encoding the antibody Fd and kappa chains is mediated through the utilization of the f1 origin of replication leading to the synthesis and packaging of the positive strand of the vector on co-infection with helper phage. Since the 'mature' virus particle assembles by incorporating the major coat protein around the single stranded DNA as it passes through the inner membrane into the periplasmic space, not only does it capture the genetic information carried on the phagemid vector but also incorporates several copies of functional Fab along the length of the particle. On subsequent infection of hosts cells carrying the F' episome the phagemid confers resistance allowing selection of colonies on the appropriate antibiotic. In essence, the antigen recognition unit has been linked to instructions for its production.

The full power of the earlier combinatorial system could not be fully utilized since screening allowed ready access to only about 0.1–1% of the members. In the phagemid/M13 system similar size libraries are generated and all the members are accessed via affinity selection. Furthermore, unlike the lambda vector which generated monovalent Fabs, this system generates multivalent particles, thus allowing the capture of a wider range of affinities.

The unique phagemid restriction sites permit the recombination of Fd and kappa chains allowing chain replacement or shuffling. The rescue of filamentous single stranded DNA allows rapid sequencing and analysis of the genetic make up of the clone of interest. Indeed it can be envisaged that phage encoding antibody specificity may be enriched by antigen selection prior to DNA sequencing or mutagenesis. The option to further develop an iterative process of mutation followed by selection may allow the rapid generation of high affinity antibodies from germ line sequences. The process may be automated. Setting aside the potential of the system to mimic nature, the phagemid/M13 system would allow a more complete dissection of the antibody response in humans which may yield useful therapeutic and diagnostic reagents.

The membrane anchoring of the heavy chain and the compartmentalization of the kappa chain in the periplasm is the key to expressing this functional dimeric protein. The potential of this system is by no means limited to antibodies and may be extended to any protein recognition system or combination of systems containing multiple members. For example coupling of ligand and effector systems in a high avidity matrix is now possible. In a similar vein a library of ligands can be sorted against a library of receptors.

6. Randomized Mutagenesis of the CDR3 Region of a Heavy Chain Encoding Anti-Tetanus Toxoid a. PCR Mutagenesis with Degenerate Oligonucleotides To obtain a mutagenized heterodimer of this invention of altered specificity that would no longer recognize a tetanus toxoid antigen (TT) but would recognize and specifically bind to a new antigen, a method was developed to randomize only the CDR3 region of a heavy chain fragment encoded by a known nucleotide sequence. This approach is schematically diagrammed in FIG. 12 where a representative heavy chain fragment within a phagemid clone, consisting of alternating framework regions. (1 through 4) shown by white blocks and complementarity determining regions (CDR) (1 through 3) shown by cross-hatched blocks and the first constant region (CH1), is subjected to two separate rounds of PCR. In the first PCR amplification reaction, the 5' end of the heavy chain beginning at framework 1 and extending to the 3' end of framework 3 is amplified. In the second PCR amplification reaction, the CDR3 region is randomly mutagenized shown by the black box. This is accomplished through the use of a pool of oligonucleotide primers synthesized with a degenerate region sandwiched between and contiguous with conserved framework region 3 and 4 sequences. The resulting amplification products from the second amplification, each having a randomized CDR3 region, have their 5' end at the 3' end of framework 3' and the 3' end of the product extends to the 3' end of the CH1 region.

The pool of degenerate oligonucleotide primers have been designed to result in the amplification of products having a 5' end that is complementary to and will overlap with the 3' end of the products of the first PCR reaction product. Thus, the two separate PCR reaction products are pooled and subjected to a third PCR reaction in which the overlapping region between the two products is extended to result in heavy chain having a randomized CDR3 region.

A heavy chain DNA template for use in this invention was available in a clone (a phagemid vector designated 7E containing heavy and light chain fragments) from a human combinatorial anti-tetanus toxoid (TT) Fab library derived from lambda Hc2 and Lc2 libraries as described by Persson et al., *Proc. Natl. Acad. Sci., USA*, 88:2432–2436 (1991). To create a semi-synthetic combinatorial library, clone 7E was constructed in pComb2-3' dicistronic expression vector for the expression of a heavy chain-cpIII membrane anchor fusion protein (Fd-cpIII) and a soluble light chain as described for anti-NPN in Example 2k by Barbas et al., *Proc. Natl. Acad. Sci., USA*, 88:7978–7982 (1991).

The phagemid vector pComb2-3' was prepared as described in Example 1b (ii). The original pairing of the heavy and light chains from the 7E lambda clone was maintained by ligation of the Xho I-Xba I fragment into a Xho I-Xba I digested pComb2-3' vector. To replace the cpIII membrane anchor sequence, LacZ promoter sequence and pel B leader deleted by the Xho I-Xba I digestion, a Spe I-Sac I fragment from pComb3, as prepared in Example 1b (ii), was ligated into the pComb2-3' vector containing the heavy and light chain sequences from clone 7E. The resultant phagemid clone, hereinafter referred to as pC3-TT7E, was first expressed as described for anti-NPN heterodimers on phage surfaces in Example 3 and subsequently screened by panning on TT-coated plates as described for anti-NPN in Example 4c. Clone pC3-TT7E exhibited a $K_d$ towards TT on the order of $10^{-7}$ M and was enriched over nonspecific phage by $10^3$-fold as described by Barbas et al., supra.

Clone pC3-TT7E, having both heavy and light chain sequences, was used as the template DNA for the randomized mutagenesis of the CDR3 region of the heavy chain to alter antigen binding specificity as described herein. The sequence of the heavy chain was determined as described in Example 1a (ii). Two separate PCR reactions were performed as illustrated in FIG. 12.

The first PCR reaction resulted in the amplification of the region of the heavy chain fragment in the pC3-TT7E clone beginning of framework region 1 and extending to the end of framework region 3 which is located 5' to CDR3 which is approximately 400 base pairs in length. To amplify this region, the following primer pairs were used. The 5' anti-sense oligonucleotide primer, FT3X, having the nucleotide sequence 5'-G-CAA-TAA-ACC-CTC-ACT-AAA-GGG-3' (SEQ ID NO 118), hybridized to the non-coding strand of the heavy chain corresponding to the region 5' of and including the beginning of framework 1. The 3' sense oligonucleotide primer, B7EFR3, having the nucleotide sequence 5'-TCT-CGC-ACA-ATA-ATA-CAC-GGC-3' (SEQ ID NO 119), hybridized to the coding strand of the heavy chain corresponding to the 3' end of the framework 3 region. The oligonucleotide primers were synthesized by Research Genetics (Hunstville, Ala.). The PCR reaction was performed in a 100 μl reaction containing one pg of each of oligonucleotide primers FTX3 and B7EFR3, 8 μl 2.5 mM dNTP's (DATP, dCTP, dGTP, dTTP), 1 μl Taq polymerase, 10 ng of template pCE-TT7E, and 10 μl of 10×PCR buffer purchased commercially (Promega Biotech). Two drops of mineral oil were placed on top of the admixture and 35 rounds of PCR amplification in a thermocycler were performed. The amplification cycle consisted of denaturing at 94° C. for one minute, annealing at 50° C. for one minute, followed by extension at 72° C. for two-minutes. The resultant PCR amplification products were then gel purified as described in Example 1d and used in an overlap extension PCR reaction with the products of the second PCR reaction, both as described below, to recombine the two products into reconstructed heavy chains containing mutagenized CDR3 regions as illustrated in FIG. 12. The total yield of DNA from this amplification was approximately 3 μg/100μl.

The second PCR reaction resulted in the amplification of the heavy chain from the 3' end of framework region 3 extending to the end of CH1 region which is approximately 390 base pairs in length. To amplify this region, the following primers were used. The 5' anti-sense oligonucleotide primer pool, designated 7ECDR3, had the nucleotide sequence represented by the formula, 5'-GTG-TAT-TAT-TGT-GCG-AGA-NNS-NNS-NNS-NNS-NNS-NNS-NNS - NNS-NNS-NNS-NNS-NNS-NNS-NNS-NNS-NNS-TGG- GGC-CAA-GGG-A CC-ACG-3' where N can be A, C, G, or T and S is either C or G (SEQ ID NO 120), wherein the 5' end of the liprimer pool was complementary to the 3 end of framework 3 represented by the complementary nucleotide sequence of the oligonucleotide primer B73FR3 and the 3' end of the primer pool was complementary to the 5' end of framework 4. The region between the two specified ends of the primer pool was represented by a 48-mer NNS degeneracy which ultimately encoded a diverse population of mutagenized CDR3 regions of 16 amino acid residues in length. The 3' sense oligonucleotide primer, CG1Z, as described by Persson et al., supra, having the nucleotide sequence 5'-GCATGTACTAGTTTTGTCACAAGATTTGGG-3' (SEQ ID NO 121), hybridized to the coding strand of the heavy chain corresponding to the 3' end of the CH1. The second PCR reaction was performed on the pC3-TT7E in a 100 µl reaction as described above containing one µg of each of oligonucleotide primers 7ECDR3 and CG1Z. The resultant PCR amplification products were then gel purified as described above. The total yield of DNA from this second PCR mutagenesis amplification was approximately 3 µg/100 µl.

One hundred nanograms of gel purified products from the first and second PCR reactions were then admixed with 1 µg each of FTX3 and CG1Z oligonucleotide primers as a primer pair in a final PCR reaction to form a complete heavy chain fragment by overlap extension as illustrated in FIG. 12. The PCR reaction admixture also contained 10 µl 10×PCR buffer, 1 µl Taq polymerase and 8 ul 2.5 mM dNTP's as described above. The PCR reaction was performed as described above. To obtain sufficient quantities of amplification product, 15 identical PCR reactions were performed. The resulting heavy chain fragments beginning at framework 1 and extending to the end of CH1 and having randomly mutagenized CDR3 regions were approximately 790 base pairs in length. The heavy chain fragment amplification products from the 15 reactions were first pooled and then gel purified as described above prior to their incorporation into a phagemid library. The total yield of DNA from each amplification was approximately 3 µg/100 µl thus the total pooled yield contained approximately 45 µg of amplified mutagenized heavy chain.

b. Phagemid Library Construction

The resultant gel purified heavy chain fragments prepared in Example 6a were then digested with the restriction enzymes, Xho I and Spe I, as described in Example 2d. The resultant digested heavy chain fragments were subsequently gel purified prior to insertion into the pC3-TT7E phagemid vector clone which was previously digested with the same restriction enzymes to remove the non-mutagenized heavy chain fragment and form a linear vector. Ligation of 640 ng of the heavy chain Xho I Spe I fragments having mutagenized CDR3 regions into two jug of the linearized pC3-TT7E phagemid vector to form circularized vectors having mutagenized CDR3 regions was performed overnight at room temperature using 10 units of BRL ligase (Gaithersburg, Md.) in BRL ligase buffer in a reaction volume of 150 µl. Five separate ligation reactions were performed to increase the size of the phage library having mutagenized CDR3 regions. Thus, the total amount of amplified mutagenized heavy chain for five ligation reactions was 3.2 µg. Following the ligation reactions, the circularized DNA was precipitated at −20° C. for two hours by the admixture of 2 µl of 20 mg/ml glycogen, 15 µl of 3 M sodium acetate at pH 5.2 and 300 µl of ethanol. DNA was then pelleted by microcentrifugation at 4° C. for 15 minutes. The DNA pellet was washed with cold 70% ethanol and dried under vacuum. The pellet was resuspended in 10 µl of water and transformed by electroporation into 300 82 1 of E. coli XL1-Blue cells as described in Example 2k to form a phage library. The total yield from the mutagenesis and transformation procedure described herein was approximately 5×10$^7$ transformants. XL1-Blue cells from E. coli were selected as the hosts as the single step codon TAG is suppressed.

After transformation, to isolate phage on which heterodimer expression has been induced, for subsequent panning on target antigens such as fluorescein, 3 ml of SOC medium (SOC was prepared by admixture of 20 g bactotryptone, 5 g yeast extract and 0.5 g NaCl in one liter of water, adjusting the pH to 7.5 and admixing 20 ml of glucose just before use to induce the expression of the Fd-cpIII and light chain heterodimer) was admixed and the culture was shaken at 220 rpm for one hour at 37° C., after which time 10 ml of SB (SB was prepared by admixing 30 g tryptone, 20 g yeast extract, and 10 g Mops buffer per liter with pH adjusted to 7) containing 20 µg/ml carbenicillin and 10 µg/ml tetracycline and the admixture was shaken at 300 rpm for an additional hour. This resultant admixture was admixed to 100 ml SB containing 50 µg/ml carbenicillin and 10 µg/ml tetracycline and shaken for one hour, after which time helper phage VCSM13 (10$^{12}$ pfu) were admixed and the admixture was shaken for an additional two hours. After this time, 70 µg/ml kanamycin was admixed and maintained at 30° C. overnight. The lower temperature resulted in better heterodimer incorporation on the surface of the phage. The supernatant was cleared by centrifugation (4000 rpm for 15 minutes in a JA10 rotor at 4° C.). Phage were precipitated by admixture of 4% (w/v) polyethylene glycol 8000 and 3% (w/v) NaCl and maintained on ice for 30 minutes, followed by centrifugation (9000 rpm for 20 minutes in a JA10 rotor at 4° C.). Phage pellets were resuspended in 2 ml of PBS and microcentrifuged for three minutes to pellet debris, transferred to fresh tubes and stored at −20° C. for subsequent screening as described below.

For determining the titering colony forming units (cfu), phage (packaged phagemid) were diluted in SB and 1 µl was used to infect 50 µl of fresh (OD600=1) E. coli XLI-Blue cells grown in SB containing 10 µg/ml tetracycline. Phage and cells were maintained at room temperature for 15 minutes and then directly plated on LB/carbenicillin plates.

c. Selection of Anti-Fluorescein Heterodimers on Phage Surfaces

1) Multiple Pannings of the Phage Library Having Mutagenized CDR3 Regions

The phage library produced in Example 6b having heavy chain fragments with mutagenized CDR3 regions was panned as described herein on a microtiter plate coated with a 50 µg/ml fluorescein-BSA conjugate to screen for anti-fluorescein heterodimers. Fluorescein was conjugated to BSA according to the methods described in "Antibodies: A Laboratory Manual", eds Harlow et al., Cold Spring Harbor Laboratory, 1988.

The panning procedure used was a modification of that originally described by Parmley and Smith (Parmley et al., Gene, 73:30–5–318). Two to four wells of a microliter plate (Costar 3690) were coated overnight at 4° C. with 25 µl of 50 µg/ml TT antigen prepared above in 0.1 M bicarbonate, pH 8.6. The wells were washed twice with water and blocked by completely filling the well with 3% (w/v) BSA in PBS and maintaining the plate at 37° C. for one hour. After the blocking solution was shaken out, 50 µl of the phage library prepared above (typically 10$^{11}$ cfu) were admixed to each well, and the plate was maintained for two hours at 37° C.

Phage were removed and the plate was washed once with water. Each well was then washed ten times with TBS/Tween (50 mM Tris-HCl, pH 7.5, 150 mM NaCl, 0.5% Tween 20) over a period of one hour at room temperature where the washing consisted of pipetting up and down to wash the well, each time allowing the well to remain completely filled with TBS/Tween between washings. The plate was washed once more with distilled water and adherent phage were eluted by the addition of 50 μl of elution buffer (0.1 M HCl, adjusted to pH 2.2 with solid glycine, containing 1 mg/ml BSA) to each well followed by maintenance at room temperature for 10 minutes. The elution buffer was pipetted up and down several times, removed, and neutralized with 3 μl of 2 M Tris base per 50 μl of elution buffer used.

Eluted phage were used to infect 2 ml of fresh ($OD_{600}$=1) E. coli XL1-Blue cells for 15 minutes at room temperature, after which time 10 ml of SB containing 20 μg/ml carbenicillin and 10 μg/ml tetracycline was admixed. Aliquots of 20, 10, and 1/10 μl were removed from the culture for plating to determine the number of phage (packaged phagemids) that were eluted from the plate. The culture was shaken for one hour at 37° C., after which it was added to 100 ml of SB containing 50 μg/ml carbenicillin and 10 μg/ml tetracycline and shaken for one hour. Helper phage VCSM13 ($10^{12}$ pfu) were then added and the culture was shaken for an additional two hours. After this time, 70 μg/ml kanamycin was added and the to culture was incubated at 37° C. overnight. Phage preparation and further panning were repeated as described above.

Following each round of panning, the percentage yield of phage were determined, where % yield—(number of phage eluted/number of phage applied)×100. The initial phage input ratio was determined by titering on selective plates, as described in Example 6b, to be approximately $10^{11}$ cfu for each round of panning. The final phage output ratio was determined by infecting two ml of logarithmic phase XL1-Blue cells as described above and plating aliquots on selective plates.

As an alternative to elution with acid, phage bound to the wells of the microtiter plate were eluted by admixing 50 μl of a solution of $10^{-5}$ M fluorescein diluted in PBS followed by a maintenance period of one hour at 37° C. The solution was then pipetted up and down to wash the wells. The resultant eluate was transferred to 2 ml of fresh E. coli XLI-Blue cells for infection as described above for preparing phage and further panning. In subsequent rounds of panning, phage were eluted with $10^{-6}$ M fluorescein.

The results of the amount of phage that were specifically bound to fluorescein-coated wells over four consecutive rounds of panning and elution with acid or with fluorescein alone are shown below in Table 8. Comparable yields of phage on which heterodimers were expressed that bound specifically to fluorescein were achieved with either elution is protocol. These data confirm that mutagenesis of the CDR3 region as described in this invention resulted in the altering of a heterodimer which initially specifically bound to TT to one that specifically bound fluorescein.

TABLE 8

| | Phage Eluted | |
| --- | --- | --- |
| | Acid Elution | Fluorescein Elution |
| round 1 | 5.6 × $10^5$/well | 4.7 × $10^5$/well |
| round 2 | 4.6 × $10^6$/well | 5.6 × $10^5$/well |
| round 3 | 3.8 × $10^5$/well | 1.4 × $10^6$/well |
| round 4 | 1.3 × $10^6$/well | 4.0 × $10^6$/well |

Nonspecific binding to this surface with control phase varied between $10^4$ and $10^5$ phage per well. Production of soluble Fab and verification of binding to fluorescein by ELISA as described in 2) below revealed 8 reactive clones of 60 randomly selected from the transformed colonies and 38 reactive clones of 40 randomly selected from the transformed colonies for the acid eluted and fluorescein eluted libraries, respectively.

2) Preparation of Soluble Heterodimers for Characterizing Binding Specificity to Fluorescein In order to further characterize the specificity of the mutagenized heterodimers expressed on the surface of phage as described above, soluble Fab heterodimers from both acid eluted and fluorescein eluted phage were prepared and analyzed in ELISA assays on fluorescein-coated plates, by competitive ELISA with increasing concentrations of soluble fluorescein-BSA and also by fluorescence quenching assays. The latter assays were performed as described in "Fluorescein Hapten: An Immunological Probe", ed E. W. Voss, CRC Press, Inc. pp 52–54, 1984.

To prepare soluble heterodimers, phagemid DNA from positive clones was isolated and digested with Spe I and Nhe I. Digestion with these enzymes produced compatible cohesive ends. The 4.7-kb DNA fragment lacking the gene III portion was gel-purified (0.6% agarose) and self-ligated. Transformation of E. coli XL1-Blue afforded the isolation of recombinants lacking the cpIII fragment. Clones were examined for removal of the cpIII fragment by Xho I-Xba I digestion, which should yield an 1.6-kb fragment. Clones were grown in 100 ml SB containing 50 μg/ml carbenicillin and 20 mM $MgCl_2$ at 37° C. until an $OD_{600}$ of 0.2 was achieved. IPTG (1 mM) was added and the culture grown overnight at 30° C. (growth at 37° C. provides only a light reduction in heterodimer yield). Cells were pelleted by centrifugation at 4000 rpm for 15 minutes in a JA10 rotor at 4° C. Cells were resuspended in 4 ml PBS containing 34 μg/ml phenylmethylsulfonyl fluoride (PMSF) and lysed by sonication on ice (2–4 minutes at 50% duty). Debris was pelleted by centrifugation at 14,000 rpm in a JA20 rotor at 4° C. for 15 minutes. The supernatant was used directly for ELISA analysis as described below and was stored at −20° C. For the study of a large number of clones, 10 ml cultures provided sufficient heterodimer for analysis. In this case, sonications were performed in 2 ml of buffer.

The soluble heterodimers prepared above were assayed by ELISA. For this assay, 1 μg/well of fluorescein-BSA solution was admixed to individual wells of a microtliter plate and maintained at 4° C. overnight to allow the protein solution to adhere to the walls of the well. After the maintenance period, the wells were washed one time with PBS and thereafter maintained with a solution of 3% BSA to block nonspecific sites on the wells. The plates were maintained at 37° C. for one hour after which time the plates were inverted and shaken to remove the BSA solution. Soluble heterodimers prepared above were then admixed to each well and maintained at 37° C. for one hour to form immunoreaction products. Following the maintenance period, the wells were washed ten times with PBS to remove unbound soluble antibody and then maintained with a secondary goat anti-human FAB conjugated to alkaline phosphatase diluted in PBS containing 1% BSA. The wells were maintained at 37° C. for one hour after which the wells were washed ten times with PBS followed by development with p-nitrophenyl phosphate (PNPP).

Immunoreactive heterodimers as determined in the above ELISA were then analyzed by competition ELISA to determine the affinity of the mutagenized heterodimers. The ELISA was performed as described above with increasing concentrations of soluble fluorescein-BSA ranging in concentration from $10^{-9}$ M up to $10^{-5}$ M in concentration admixed in the presence of the soluble heterodimers. Maximal inhibition of binding was achieved at a concentration of $10^6$ M free antigen with a half-maximal inhibition obtained with approximately $10^{-7}$ M free antigen. Antibodies expressed from all clones had approximate dissociation constants (Kd) in the range of $10^{-7}$ to $10^{-8}$ M for fluorescein-BSA conjugates for both the fluorescein and acid elutions. True Kd's were determined in fluorescence quenching assays. Antibodies expressed on phage from clones following fluorescein elution had higher affinities for fluorescein, $10^{-7}$ M versus $10^{-6}$ M for the acid eluted antibodies. The parent clone, 7E, showed no quenching within detectable limits of the assay suggesting an affinity for free fluorescein less than $10^{-5}$ M. The affinities of the tightest binders of antibodies to fluorescein ($10^{-7}$ M) approached the average Kd of the secondary response of immunized mice for free fluorescein ($10^{-7}$ M) as shown by Kranz et al., *Mol. Immunol.*, 20:1313–1322 (1983).

Thus, the mutagenized heterodimers of this invention specifically recognized and bound to fluorescein. Additional experiments were performed to confirm that the mutagenized heterodimers no longer recognized the TT to which the nonmutagenized heterodimer originally bound. Fluorescence quenching assays were also performed to confirm the specificity of binding of the mutagenized heterodimers. Soluble heterodimers prepared from phage that were either eluted with acid or with fluorescein alone were equally effective at binding fluorescein by any of the aforementioned approaches. The invention of mutagenesis of the CDR3 region of the heavy chain of a heterodimer described herein thus resulted in the alteration of binding specificity from TT to fluorescein.

d. Sequence Analysis of Selected Anti-Fluorescein Heterodimers

The complete nucleotide sequence of the mutated heavy chain of a representative number of fluorescein-BSA binding clones was determined. No PCR induced mutations outside of the CDR3 region were observed. The predicted amino acid sequences of the heavy chain CDR3 region are shown in FIG. 13 with the corresponding SEQ ID NO shown in parenthesis. Seven clones recovered from the acid elution regimen showed no consensus sequence. The lack of consensus behavior in the acid eluted clones may be contributed by their recognition of a more complex epitope consisting of fluorescein and BSA and is reflected in the more disparate affinities to fluorescein and fluorescein-BSA.

Conversely, the clones isolated by fluorescein elution showed a high selection of consensus sequences. Of ten clones sequenced, only three different sequences were observed. All of the clones had a glycine residue at amino acid residue position 95 and an aspartic acid residue at position 101. The amino acid residue positions are based on the Kabat numbering system as described by Kabat et al., in "Sequences of Proteins of Immunological Interest, U.S. Department of Health and Human Services, (1987). Both possible codons for encoding the glycine residue provided by the synthesis protocol in which all 32 possible codons were produced were used. In natural antibodies, the aspartic acid residue at position 101 usually plays a structural role by forming a salt bridge with an arginine residue at position 94 in framework region 3 (FR3). Thus, the artificial selection process had recapitulated an interaction of structural significance which mirrors that seen in the animal.

In addition, nine of the semi-synthetic antibodies expressed from ten clones contained a serine-arginine-proline triplet sequence near the center of the loop directly adjacent or one residue removed on the amino-terminal side of an arginine residue, though the codon usage for two of these residues was different. Clone F31 lacked this central motif. All sequences were rich in arginine residues which was encoded by three of the 32 possible codons. Comparison of the occurrence within the ten difference CDR3 sequences of arginine with leucine and serine, which were also encoded by three possible codons in the synthesis, revealed a arginine-leucine-serine ratio of 29:16:15. This bias towards selection of arginine may be the result of the dianionic character of fluorescein.

The finding that different codons were used support the proposition that clonal selection occurred at the level of antigen-antibody union and not because of some unexpected bias of nucleotide incorporation into DNA.

7. Randomized Mutagenesis of the CDR3 Region of a Light Chain Encoding Anti-Tetanus Toxoid a. PCR Mutagenesis with Degenerate Oligonucleotides Following a similar procedure to the random mutagenesis of the heavy chain as described in Example 6, the CDR3 region of a light chain fragment of the anti-tetanus toxoid specific phagemid clone pC3-TT7E was randomized to produce antibodies having a specificity for fluorescein. The PCR amplifications were performed as described in Example 6a with the exception of the oligonucleotides primers used in the reactions.

The first PCR reaction resulted in the amplification of the region of the light chain fragment in the pC3-TT7E clone from the 5' EcoR V site of the vector extending into the 5' end of the CDR3 region. To amplify this region, the following primers were used: The 5' anti-sense oligonucleotide primer, KEF, having the nucleotide sequence 5'-GAATTCTAAACTAGCTAGTCG-3' (SEQ ID NO 126), hybridized to the non-coding strand of the light chain corresponding to the EcoR V site in the vector; The 3' sense oligonucleotide primer, KV12B, having the nucleotide sequence 5'-ATACTGCTGACAGTAATACAC-3' (SEQ ID NO 127), hybridized to the coding strand of the heavy chain corresponding to the 5' end of CDR3. The PCR amplification was performed as described in Example 6a. The resultant PCR products were then gel purified as described in Example 1d and used in an overlap extension PCR reaction with the products of the second PCR reaction, both as described below, to recombine the two products into reconstructed heavy chains containing mutagenized CDR3 regions as illustrated in FIG. 12.

The second PCR reaction resulted in the amplification of the light chain from-the 5' end of the CDR3 region extending to the end of the CH1 region. To amplify this region, the following primers were used. The 5' anti-sense oligonucleotide primer pool, designated KV5R, had the nucleotide sequence represented by the formula, 5'-TATTACTGTCAGCAGTATNNKNNKNNKNNKNN KACTTTCGGCGGAGGGAC C-3' (SEQ ID NO 128) where N can be A, C, G or T and where K is either G or T, wherein the 5' end of the primer pool was complementary to the 5' end of CDR3 and the 3' end of the primer pool was complementary to the 3' end of CDR3 and the 5' end of framework 4. The region between the two specified ends of the primer pool was represented by a 15-mer degeneracy which ultimately encoded a diverse population of internal mutagenized CDR3 regions of 5 amino acids in length bordered by non-mutagenized 5' and 3' ends of the CDR3 regions. The 3' sense oligonucleotide primer, T7B, having the nucleotide sequence 5'-AATACGACTCACTATAGGGCG-3" (SEQ ID NO 129), hybridized to the coding strand of the light chain corresponding to the T7 region in the vector. The second PCR reaction was performed on the pC3-TT7E as described in Example 6a with the KV5R and T7B primers. The resultant PCR amplification products were then gel purified as described above.

Five hundred nanograms of gel purified products from the first and second PCR reactions were then admixed with 1 μg each of KEF and T7B oligonucleotide primers as a primer pair in a final PCR reaction to form a complete light chain fragment by overlap extension as illustrated in FIG. 12. The PCR amplification was performed as described in Example 6a. To obtain sufficient quantities of amplification product, 5 identical PCR reactions were performed. The resulting light chain fragments, that began at the 5' EcoR V site and extended to the T7 region, had five internal amino acids randomly mutagenized CDR3.

b. Phagemid Library Construction

The resultant gel purified light chain fragments prepared in Example 7a were then digested with the restriction enzymes, Sac I and Xba I, as described in Example 2d. The resultant light chain fragments were subsequently gel purified prior to ligation into the pC3-TT7E phagemid vector clone which was previously digested with the same restriction enzymes to remove the non-mutagenized light chain fragment and form a linearized vector. Ligation of 450 ng of light chain amplification products into 1.4 μg linearized pC3-TT7E phagemid vector to form circularized vectors having mutagenized CDR3 regions was performed as described in Example 6b. Five separate ligation reactions were performed to increase the size of the phage library having internally mutagenized CDR3 regions. Following the ligation reactions, the circularized DNA was precipitated and transformed into E. coli XL1-Blue as described in Example 6b to form a phage library. The total yield from the mutagenesis and transformation procedure described herein was approximately $2 \times 10^7$ transformants. Phage were isolated as described for the heavy chain mutagenesis transformants.

c. Selection of Anti-Fluorescein Heterodimers on Phage Surfaces and Sequence Analysis of Selected Antibodies The phage library produced in Example 7b having light chain fragments with five internally mutagenized amino acids in the CDR3 region was panned as described in Example 6c. The numbers of phage that were specifically bound to fluorescein-coated wells over three consecutive rounds of panning and hapten elution with a phage input of $10^{11}$ were $0.75 \times 10^6$, $1 \times 10^6$ and $2.4 \times 10^7$ The repeated cycles of transformation, phage preparation, panning and elution thus resulted in a significant enrichment of heterodimers that specifically bound to fluorescein. Soluble Fabs were prepared as described in Example 6b2) for characterizing binding specificity to fluorescein. Seven clones were selected for sequence analysis as described in Example 6d. The results of the sequence analysis are shown in FIG. 14. The mutated region of the light chain CDR3 spans Kabat amino acid immunoglobulin light chain positions from 92 to 96. The sequence of this region from the starting clone, pC3-TT7E, was Gly-Ser-Ser-Leu-Trp (SEQ ID NO 148). Of the seven antibodies mutated and selected on fluorescein, five of them from clones P2, P21, P23, P28 and P19 had the amino acid sequence Thr-Arg-Pro-Gly-Val (SEQ ID NO 149) but each were the result of translations from unique nucleotide sequences. The two remaining antibodies from P15 and P11 clones, derived from unique nucleotide sequences, also had unique amino acid sequences. Thus, since most of the mutagenized light chains had the same amino acid sequence encoded by the possible codons in the synthesis, the artificial selection process has recapitulated an interaction of structural significance which in the animal resulted from the process of natural selection.

Mutagenesis of the CDR regions is not limited to the CDR3 region as primers can be designed to result in the random mutagenesis of CDR1 and CDR2 of both the heavy and the light chain. Mutating all six CDR regions would result in an-exceptionally diverse library beyond that which can be obtained in the animal. To obtain randomization in all the CDRs, the heavy chain CDRs could first be randomized from a starting clone followed by selection of the best antibody binders. A second mutagenesis step on the CDRs of the light chain could be performed and the resultant library can be mixed with the selected heavy chain binders. Alternatively, all CDRs could be simultaneously randomized resulting in heavy and light chain libraries which are then combined and subjected to selection against a preselected antigen.

Thus, the Examples 6 and 7 illustrate a method according to the present invention for mutagenizing the heavy and light complementarity determining regions (CDR) of an immunoglobulin gene, and also illustrates oligonucleotides useful therefor.

8. In Vitro Selection and Affinity Maturation of Antibodies from a Naive Combinatorial Immunoglobulin Library A combinatorial immunoglobulin library approach has been used to obtain monoclonal antibodies from non-immune adult mice, thereby establishing the principles of (i) accessing naive combinatorial antibody libraries for predetermined specificities and (ii) increasing the affinity of the selected antibody binding sites by random mutagenesis. A combinatorial Fab library expressing Igμ and k light chain fragments on the surface of filamentous phage was prepared from bone marrow of non-immunized, adult Balb/c mice with the multivalent display vector pComb8 prepared in Example 1b(i). Phage displaying low affinity Fab's having binding constants of approximately $10^4$ to $10^5$ $M^{-1}$ specific for progesterone were isolated from the library by their ability to bind the hapten. Random mutagenesis of the heavy and light chain variable regions expressed in the monovalent phage display vector pComb3 was performed by error-prone PCR. Clones with improved affinity for progesterone were subsequently selected. Thus, as described herein, antibodies with desirable characteristics from a non-immune source were selected and affinity maturation achieved by using the twin vectors pComb8 and pComb3, thus opening the route to obtaining specific antibodies from a generic library and bypassing immunization.

The invention described herein has three essential features: (i) the ability to initially access low affinity Fabs from a naive library by the use of multivalent phage expression systems, (ii) subsequent affinity maturation by error-prone PCR and (iii) the use of a single chain construct during the maturation process to avoid a high background of artifactual binding due to loss of the light chain. When used in concert, these methods allowed for the selection and affinity maturation of antibodies from a naive library.

a. RNA Isolation and cDNA Synthesis

Three non-immunized adult male (6 months) Balb/cByJ mice (Scripps breeding colony) were used to prepare $5 \times 10^7$ bone marrow cells in 4% fetal calf serum in PBS. To deplete for surface IgG positive cells, the preparation was maintained with rat-anti mouse $IgG_{2b}$ (0.1 ml), goat anti-mouse IgG (0.1 ml), and rabbit anti-mouse $IgG_{2b}$ (0.1 ml) for 30 minutes at ambient temperature. The cells were pelleted, washed with PBS and resuspended in 9 ml PBS. Rabbit complement was added (1 ml) and maintained at 37° C. for 30 minutes. The cells were pelleted and total RNA isolated as described in Example 2b. The total RNA was used as a template for the cDNA synthesis for μ-and k-chains with the following primers: Igμ, 5'-ATTGGG ACTAGTTTCTGCGACAGCTGGAAT-3' (SEQ ID NO 152) (the Spe I restriction site sequence is underlined) and k, 5'-GCGCCG TCTAGAATTAACACTCATTCCTGTTGAA-3' (SEQ ID NO 153) (the Xba I restriction site is underlined) respectively, using SuperScript Kit (BRL).

Briefly, 7 μg of total RNA was admixed with 60 pmol of primer, heated to 70° C. for 10 minutes and immediately cooled on ice. Two μl of RNase inhibitor, 10 μl of 5×synthesis buffer, 8 μl of DNTP mix (to give final concentration of 200 μM of each NTP), 5 μl of 0.1 M DTT, and 1 μl of BRL SuperScript RT (200 U/μl) were admixed, and the reaction was made up to 50 μl with DEPC treated water. The reaction was allowed to proceed at room temperature for 10 minutes and then at 42° C. for 50 minutes. The reaction was terminated by maintaining at 90° C. for 5 minutes and then placing on ice for 10 minutes followed by admixing 1 μl of RNase H and maintaining at 37° C. for 20 minutes. PCR amplification was performed in a 100 μl reaction mixture as described in Example 2, using $V_H$ 1–9 and the μ chain primer for the heavy chains and $V^L$3–7 and the k chain primers for the light chains as shown in Table 5.

b. Naive Immunoglobulin μ/k Library Construction

The PCR amplified μ-chain and k-chain DNA were cleaved with Xho I-Spe I and Sac I-Xba I, respectively. The resulting μ chain Xho I-Spe I fragments were inserted into the pComb8 phagemid vector prepared in Example 1b(i) to generate a μ chain-cp VIII fusion library. Transformation into E. coli XL1-Blue and phage production was carried out essentially as described in Example 6. Subsequently, the k light chain Sac I-Xba I fragments were cloned into the heavy chain $F_d$ μ-cpVIII fusion library.

A combinatorial library of $5 \times 10^6$ members was established by subsequently cloning the Igμ $F_d$ and k light chain fragments into the pComb8 vector which allowed the fusion of the heavy chain $F_d$ fragment to cpVIII. Since the Fab antibody fragments were displayed at a high copy number on the phage surface, this vector was selected for accessing low affinity antibodies which are expected to be found in an unselected and unprimed repertoire.

c. Selection of Low Affinity Antibodies Specific for Progesterone

The recombinant phagemids prepared above were packaged into M13 phage particles and five rounds of panning on progesterone-3-(O-Carboxymethyl)-oxime-BSA coated ELISA wells was performed as described in Example 6. Briefly, wells of a microtitration plate were coated at 4° C. with 50 μl of 100 μg/ml progesterone-3-(O-Carboxymethyl)-oxime BSA conjugate (Sigma #P4778) in PBS. The wells were washed twice with water and blocked by completely filling with 1% w/v BSA in PBS and maintaining the plates at 37° C. for one hour. Blocking solution was flicked out and 50 μl of the phage library (typically $10^{11}$ cfu) in PBS-BSA (0.1% w/v) were admixed to each well and the plates maintained for two hours at 37° C. The washing steps, elution, and multiplication of the phage were done essentially as described in Example 6a1).

Phage eluted after the first and third round were analyzed for expression of anti-progesterone Fab's by bacterial colony lifts as described in Example 2f. The colonies were probed for progesterone binding with a progesterone-3-(O-Carboxymethyl) -oxime HRP conjugate. The filters were developed using 4-chloronaphthol. Care was taken to exclude artifacts caused by phagemids expressing the Igμ $F_d$ cpVIII fusion without a corresponding light chain. These heavy chain-only phages reacted nonspecifically to unrelated antigens such as BSA, HRP, hen egg lysozyme, presumably due to the hydrophobic patch displayed on an unpaired heavy chain.

Those colonies producing the strongest signal in the western blot were further examined, and three Its clones, PgA11, PgB6, and PgF1, were isolated for subsequent analysis. The first two emerged from the first round of panning, and the latter was isolated after the third round of selection. All three Fab's, produced in their soluble form as described in Example 6c2) bound specifically to progesterone-3-(O-Carboxymethyl)-oxime-BSA and progesterone-11α-hemisuccinyl-BSA. Additionally, all three Fab's displayed a significant crossreactivity against an epitope on cytochrome C. Their apparent binding constants for progesterone-3-(O-carboxymethyl)-oxime-BSA were determined as $10^4$ $M^{-1}$ for PgA11, and $3 \times 10^4$ $M^{-1}$ and $10^5$ $M^{-1}$ for PgF1 and PgB6, respectively. These binding constants were much below that reported for anti-progesterone monoclonal antibodies with affinities of 2 to $5 \times 10^8$ $M^{-1}$. Clones PgB6 and PgF1 utilized the same combination of closely related $V_H$ and $V_L$ genes. Both of their $V_H$ genes were identical to two closely related but distinct germline genes with no evidence of somatic mutation, as one would expect for a naive repertoire. The true germline gene(s) for their closely related $V_L$ genes are not yet known. Since both the $V_H$ genes have joined to different D and J segments, the clones PgB6 and PgF1 cannot be of the same origin, but must have been selected from two independent cloning events, pointing towards a possible importance of this particular combination for progesterone binding. The $V_L$ and $V_H$ genes used by PgA11 are not closely related to the other two clones.

Thus, this demonstrated that by using a multivalent display vector, Fab's can be isolated from naive combinatorial libraries with affinities comparable to those observed for the primary immune response to haptens, such as phosphorylcholine and nitrophenol. Further, the combinatorial library approach can yield V genes or V gene combinations which would not have been selected in vivo.

d. Affinity Maturation by PCR Directed Mutagenesis

To mimic the process of somatic mutation which leads to the selection of antibodies with a higher affinity, random mutations were created in both the $V_L$ and $V_H$ regions and antibodies were subsequently selected with an increased affinity to the hapten progesterone. In order to target the mutations by error-prone PCR specifically and only to the V regions, a single chain fusion plasmid Fv-cpIII was constructed in a pComb2-3 phagemid vector which contained in frame fusions of the following elements: the pelB leader sequence for secretion, the $V_H$ and $V_L$ reading frames linked with a synthetic oligonucleotide coding for a flexible peptide as discussed in Example 6a, and the cpIII moiety. The use of a single chain vector further overcomes the difficulties due to unwanted selection for nonspecific binding by phage which express Ig heavy chains only.

For preparing a single-chain heavy and light chain (designated $F_V$) fusion with the membrane anchor cpIII, the plasmid pComb2-3 prepared in Example 1b(ii) having only one Spe I restriction site, was digested with the restriction endonucleases Xba I and Nhe I and religated, thus eliminating the light chain cloning cassette. A synthetic DNA linker which encodes a 15 amino acid linker sequence consisting of two oligonucleotides, a 5' anti-sense primer having the nucleotide sequence 5'-TCGAGAAAGTC TCTAGAGGTAAATCTTCTGGTTCTGGTTCCGAA TCTAAATCTA CTGAGCTCAAAGTCA-3' (SEQ ID NO 154) and a 3' sense primer having the nucleotide sequence 5'-CTAGTGACTTT GAGCTCAGTAGATTTAGATTCGGAACCAGAAC CAGAAGATTTA CCTCTAGAGACTTTC-3 (SEQ ID NO 155) was inserted into the Xho I-Spe I digested, truncated pComb2-3 vector forming the phagemid ScpComb2-3. The internal recognition sequence for restriction endonucleases Xba I (TCTAGA) and Sac I (GAGCTC) are underlined. The $V_H$ and $V_L$ segments of the progesterone binders were then amplified by PCR as described in Example 2g in two separate reactions.

In the first PCR amplification, the primer corresponding to SEQ ID NO 154 listed above and the oligonucleotide having the nucleotide sequence 5-'ATTTGGGAAGGACTG TCTAGATGMRGAGAC-3', (SEQ ID NO 156), where M is either A or C and R is either A or G, were used to amplify the heavy chain fragment. The light chain fragment was separately amplified with the primer corresponding SEQ ID NO 154 listed above and the oligonucleotide having the nucleotide sequence 5'-GAGG ACTAGTTACAGTTGGTGCAGCATCAG-3' (SEQ ID NO 157. The internal recognition sequences for Xba I (TCTAGA) and Spe I (ACTAGT) are underlined. The $V_H$ and $V_L$ PCR fragments were digested with Xho I-Xba I and Sac I-Spe I, respectively, and subsequently inserted into Scp-Comb2-3.

e. Expression and Detection of Soluble Fabs and Single Chain Fusion Antibodies Specific for Progesterone For Fab production, the gene VIII moiety in the phagemids encoding the progesterone binders PgA11, PgB6, and PgF1 was excised with restriction endonucleases Spe I and EcoR I and subsequently replaced by a synthetic linker encoding a TAA stop codon (underlined). The linker was formed by the oligonucleotides 5'-CTAGT TAACTGAGTAAG-3' (SEQ ID NO 158) and 5' AATTCT-TACTCAGTTAA-3' (SEQ ID NO 159'). The production and detection of antibody Fab fragment was performed essentially as described in Example 6c2), except that the E. coli cells were disrupted by three freeze thaw cycles. For producing soluble antibody fragments, the $V_H$-linker-$V_L$ fusions were excised from the ScpComb2-3 phagemid with Xho I and Spe I and subcloned into the expression vector pTAC01 (Pharmacia) which is a derivative of pF1260. The pTAC01 vector has the inducible tac promoter, the pe1B leader sequence for secretion and allowed for in-frame fusion of the inserted single chain fusion construct with a decapeptide sequence as described in Example 1a as a tag for immunochemical detection. Expression and detection of the single chain fusion antibody fragments was as described above, except that an anti-decapeptide antibody conjugated to alkaline phosphatase was used for the ELISA.

Three single chain fusion clones were selected by the screening protocol and designated ScpComb2-3-PgF1, -PgB6 and -PgA11. These resultant plasmids were subjected to error-prone PCR mutagenesis as described below.

f. Targeted Mutagenesis of the Heavy and Light Chains by Error-Prone PCR

Equal amounts of undigested PgF1, PgB6, and PgA11 ScpComb2-3 plasmids prepared above were admixed and serially diluted. Aliquots of 100 ng, 10 ng, 1 ng, 0.1 ng, and 0.01 ng of the admixtures were subjected separately to 35 cycles (1 minute at 94° C., 2 minutes at 50° C., 1 minute at 72° C.) of amplification under the following reaction conditions: 50 mM KCl, 10 mM Tris-Hcl (pH 9.0), 6.5 mM $MgCl_2$, 0.5 mM $MnCl_2$, 0.01% gelatin, 0.1% Triton X-100, 1 mM each dCTP, dGTP, dTTP, 0.2 mM DATP, 0.1 mM dITP, using the M 13 reverse sequencing primer, 5'-AACAGCTATGACCATG-3' (SEQ ID NO -160), and a backward primer complementary to the cpIII moiety, 5'-GACAGGAGGTTGAGGCAGGT-3' (SEQ ID NO 161) at 100 $\mu$M. The basic method of error-prone PCR was as originally described by Leung et al., J. Methods Cell. Mol. Biol., 1:11–15 (1989) which is to incorporated herein by reference. The DNA region to be mutagenized was PCR amplified under conditions that reduced the fidelity of DNA synthesis by Taq DNA polymerase. As shown by Leung et al., supra, the concentrations of the reagents $MuCl_2$ and dATP used in the PCR amplifications resulted in 1.0% and 1.4% mutation frequency, respectively. Thus, the frequency of mutation increased as the DATP concentration decreased.

The PCR reactions of all template dilutions were pooled and treated with phenol prior to digestion with Xho I and Spe I. The gel purified and digested PCR fragments were ligated back into the Xho I-Spe I digested ScpComb2-3 plasmid. The ligation products were electroporated into E. coli XL1-Blue giving rise to $10^6$ transformants. Subsequent steps of phage production and panning were carried out as described in Example 6, except that the phage were panned in the absence of BSA.

Thus, a library of mutated anti-progesterone single chain phagemid antibodies was established and panned on progesterone-3-(O-Carboxymethyl)-oxime-BSA and the number of eluted cfu was taken as a measure for the relative affinity of the displayed single chain antibodies to the hapten. After the third round of panning a 50 to 100-fold increase in the yield of eluted phagemids relative to the non-mutated population was noted. Individual mutants showed a 10 to 300-fold increase in yield after panning as compared to the parent clones, indicating that the mutants encoded antibody binding sites with an increased affinity. The four best mutants, designated ScPgB6-1, -2, -3 and -4, were chosen for determination of their affinity for the hapten-conjugate and sequence analysis.

g. Determination of Affinity of Mutagenized Single Chain Fusion Anti-Progesterone Antibodies The binding constants of the soluble antibody fragments prepared form the four best mutants, ScPgB6-1, -2, -3 and -4 chosen above were determined by competitive ELISA as described in Example 6c2). Briefly, wells of a microtitration plate were coated at 4° C. with 50 $\mu$l of 100 $\mu$g/ml progesterone-3-(O-Carboxymethyl)-oxime-BSA conjugate in PBS. The wells were washed twice with water and blocked with 1% w/v BSA in PBS at 37° C. for one hour. Fab or single chain fusion supernatants were mixed with progesterone-3-(O-Carboxymethyl)-oxime-BSA in PBS-BSA (0.1% w/v), and maintained in the wells at 37° C. for two hours. The plates were washed with PBS-Tween (0.05% v/v), and goat anti-mouse k-chain alkaline phosphatase conjugate (Southern Biotech) or mouse anti-decapeptide monoclonal antibodies conjugated to alkaline phosphatase was admixed and maintained for one hour at 37° C. The plates were washed as before and substrate was admixed (0.1 ml, p-nitrophenyl phosphate at 1 mg/ml in 0.1 M Tris, pH 9.4 containing 50 mM $MgCl_2$). After maintenance at 25° C. for 60–180 minutes, the absorbance was read at 405 nm. Apparent affinities were determined as the reciprocal of the hapten concentration required to inhibit 50% of the maximal binding in a competitive ELISA. This was a close approximation to the affinity and permitted the ranking of the binding activities.

The affinity of the mutated Sc antibodies to progesterone-3-(O-carboxymethyl)-oxime-BSA as determined by competitive ELISA had increased over the parent ScPg6 antibody by 30-fold for ScPgB6-1, and approximately 13-fold for both ScPgB6-3 and ScPgB6-4. Interestingly, the clone with the least mutations exhibited the highest affinity. The crossreactivity pattern for the mutant Sc antibodies did not change, except that ScPgB6-1 had lost most of its reactivity to cytochrome C. In extensively studies immune responses to haptens, an increase in affinity by one order of magnitude could be assigned to specific single amino acid substitutions, which implies that only one or two amino acid exchanges in the combining site of the Sc anti-progesterone antibodies may have accounted for their increased affinity to the hapten-conjugate. Since a mutant with only a single amino acid exchange was not recovered, the critical residue(s) could not be identified that caused the enhanced affinity to the hapten-conjugate. Further, amino acid substitutions common to all three of the mutants were not observed which suggested that changing different residues can account for the increased affinity to 3-(O-carboxymethyl)-progesterone. A $Ser_{64}$ to $Pro_{64}$ substitution in the $V_H$ CDR2 is common to the mutants ScPgB6-3 and ScPgB6-4. Although both mutants showed a similar affinity to the hapten-conjugate, assessing the importance of that residue for antigen binding cannot unequivocally be done, since multiple amino acid exchanges occurred in the $V_L$ and $V_H$ regions of the two mutants.

h. Nucleic Acid Sequencing

The complete nucleotide sequences of the variable regions of the heavy and light chains were determined from double stranded DNA using Sequenase 2.0 (United States Biochemical). DNA sequencing revealed that all four mutant clones, ScPgB6-1, -2, -3 and -4, had arisen from ScPgB6, with ScPgB6-1 and ScPgB6-2 being identical. The predominant type of mutation obtained by this PCR protocol was an A-G/T-C nucleotide exchange (68%), while T-G/A-C, G-A/C-T, T-A/A-T, G-C/C-G, or C-A/G-T exchanges occurred at approximately the same frequency. DNA sequences with a higher than average mutation frequency, i.e. mutational hot spots, were observed. In addition, the three mutant clones differed in the number of basepair changes. The mutation frequencies for both the $V_H$ and $V_L$ regions were found to be 1.5% for ScPgB6-1, 2.1% for ScPgB6-3, and 4.1% for ScPgB6-4, which led to multiple amino acid substitutions in the CDR's and framework regions of the mutants.

In summary, this invention contemplates the principle of selection and affinity maturation of specific antibodies to a hapten from a naive library. Although in vitro selection and mutagenesis system is quite simple compared to the complexity of the immune system, some common features exist: (i) The affinity of antibodies selected from a naive combinatorial library can reach the same order of magnitude as antibodies from a primary immune response to haptens; (ii) Although the mechanisms generating mutations in vivo or in vitro were different, mutational hot spots were observed; (iii) The increase in affinity after one round of mutation and selection in vitro is in the same order of magnitude as observed for the transition from primary to secondary immune responses to haptens; and (iv) A mutated antibody combining site with an altered crossreactivity was recovered as is occasionally observed in vivo.

When the combinatorial antibody approach was first described, whether it could be used to efficiently tap into the vast antibody-repertoire in vivo was questionable. The present invention shows that antibody chain combinations can be accessed and evolved which may never be selected in vivo. Thus, it now seems as if it is possible to exceed the diversity of the antibody response in vivo by molecular cloning techniques.

The foregoing is intended as illustrative of the present invention but not limiting. Numerous variations and modifications can be effected without departing from the true spirit and scope of the invention.

What is claimed is:

1. A method for maturing the affinity of a heterodimeric antibody encoded by a filamentous phage encapsulating a genome encoding said heterodimer antibody comprising first and second polypeptides wherein said first polypeptide is fused to a filamentous phage membrane cpVIII anchor domain, said method comprising the steps of:
   a) providing the genome of said filamentous phage;
   b) mutating the immunoglobulin variable domain-coding nucleotide sequence present in the provided genome to form a library of phage particles containing a mutated immunoglobulin variable domain nucleotide sequence;
   c) contacting the library formed in step (b) with a preselected ligand under conditions sufficient for members of the library to bind to the ligand and form a ligand-phage particle complex; and
   d) isolating phage particles in said complex away from non-bound library members to form a ligand-enriched library comprising phage particles having binding specificity for said preselected ligand.

2. The method of claim 1 wherein said mutating comprises subjecting said immunoglobulin variable domain-coding nucleotide sequence to an error-prone polymerase chain reaction.

3. The method of claim 1 wherein said immunoglobulin variable domain is $V_H$.

4. A method for changing the diversity of a library of filamentous phage particles comprising the steps of:
   a) providing a library of filamentous phage particles wherein each phage particle contains at least one ligand-binding heterodimeric antibody comprising first and second polypeptides expressed from a dicistronic expression vector wherein said first polypeptide is fused to a filamentous phage membrane cpVIII anchor domain;
   b) contacting the provided library with a preselected ligand under conditions sufficient for members of the library to bind to the ligand and form a ligand-phage particle complex; and
   c) isolating phage particles in said complex away from non-bound library members to form a ligand-enriched library comprising phage particles having binding specificity for said preselected ligand.

5. The method of claim 4 wherein said preselected ligand is affixed to a solid support, said complex is in the solid phase and said isolating comprises the steps of:
   i) washing the solid support to rinse non-bound library members from the solid support; and
   ii) eluting solid-phase bound phage particles to form said isolated phage particles.

6. The method of claim 5 wherein said eluting comprises contacting said solid-phase bound phage particles with an elution buffer having a pH of from pH 2 to pH 6.

7. The method of claim 5 wherein said elution comprises contacting said solid-phase bound phage particles with an elution buffer containing said preselected ligand.

8. The method of claim 5 wherein said first and second polypeptides are immunoglobulin heavy and light chain variable domains.

9. The method of claim 5 wherein said dicistronic expression vector is pCOMB8.

10. The method of claim 5 wherein said filamentous phage membrane cpVIII anchor has an amino acid residue sequence represented by the formula in SEQ ID NO 17.

11. A method for increasing the diversity of a library of filamentous phage particles comprising the steps of:
    a) providing a library of filamentous phage particles wherein each phage particle contains a dicistronic vector for expressing first and second polypeptides comprising an immunoglobulin variable domain, wherein said first polypeptide is fused to a filamentous phage membrane cpVIII anchor domain;
    b) mutating the immunoglobulin variable domain-coding nucleotide sequence present in each DNA expression vector in the library to form a library of phage particles each containing a mutated immunoglobulin variable domain nucleotide sequence.

12. The method of claim 11 wherein said mutating comprises subjecting said immunoglobulin variable domain-coding nucleotide sequence to an error-prone polymerase chain reaction.

13. The method of claim 11 wherein said immunoglobulin variable domain is $V_H$.

14. The method of claim 11 wherein said dicistronic expression vector is pCOMB8.

15. The method of claim 11 wherein said filamentous phage membrane cpVIII anchor has an amino acid residue sequence represented by the formula in SEQ ID NO 17.

* * * * *